United States Patent
Chun et al.

(10) Patent No.: US 11,859,243 B2
(45) Date of Patent: *Jan. 2, 2024

(54) DIFFERENTIATION OF SIGNALS FOR TARGET NUCLEIC ACID SEQUENCES

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 384 days.

This patent is subject to a terminal disclaimer.

(21) Appl. No.: 17/130,887

(22) Filed: Dec. 22, 2020

(65) Prior Publication Data

US 2021/0108260 A1  Apr. 15, 2021

Related U.S. Application Data

(63) Continuation of application No. 15/534,643, filed as application No. PCT/KR2015/013461 on Dec. 9, 2015, now Pat. No. 10,876,155.

(60) Provisional application No. 62/154,319, filed on Apr. 29, 2015.

(51) Int. Cl.
*C12Q 1/6851* (2018.01)
*G16B 40/00* (2019.01)
*G16B 40/10* (2019.01)

(52) U.S. Cl.
CPC .......... *C12Q 1/6851* (2013.01); *G16B 40/00* (2019.02); *G16B 40/10* (2019.02)

(58) Field of Classification Search
CPC ....... C12Q 1/6886; G16B 40/00; G16B 40/10
See application file for complete search history.

(56) References Cited

U.S. PATENT DOCUMENTS

| | | | |
|---|---|---|---|
| 5,538,848 A | 7/1996 | Livak et al. | |
| 9,284,607 B2 | 3/2016 | Fu | |
| 9,540,681 B2 | 1/2017 | Chun et al. | |
| 2005/0053950 A1 | 3/2005 | Zudaire Ubani et al. | |
| 2011/0151461 A1 | 6/2011 | Link et al. | |
| 2012/0116686 A1 | 5/2012 | Palais et al. | |
| 2012/0202203 A1 | 8/2012 | Reis, Jr. et al. | |
| 2017/0027750 A1 | 2/2017 | Wiley | |
| 2017/0362646 A1 | 12/2017 | Chun et al. | |

FOREIGN PATENT DOCUMENTS

| | | |
|---|---|---|
| JP | 2004533801 A | 11/2004 |
| JP | 2012513215 A | 6/2012 |
| JP | 2013540449 | 7/2013 |
| JP | 2013538041 | 10/2013 |
| KR | 10-1032750 B1 | 5/2011 |
| WO | 2001066799 A2 | 9/2001 |
| WO | 2006044994 A2 | 4/2006 |
| WO | 2010013017 A1 | 2/2010 |
| WO | 2010068576 A1 | 6/2010 |
| WO | 2010075413 A1 | 7/2010 |
| WO | 2010104768 A1 | 9/2010 |
| WO | 2011019837 A1 | 2/2011 |
| WO | 2012048207 A2 | 4/2012 |
| WO | 2012096523 A2 | 7/2012 |
| WO | 2013115442 A1 | 8/2013 |
| WO | 2013133561 A1 | 9/2013 |
| WO | 2014022827 A1 | 2/2014 |
| WO | 2015147370 A1 | 10/2015 |

OTHER PUBLICATIONS

Sanchez, J. Aquiles, et al., Two-temperature LATE-PCR endpoint genotyping, BMC Biotechnology 2006, vol. 6, No. 44, pp. 1-14.
Chakravorty, Soumitesh, et al., Rapid Detection of Fluoroquinolone-Resistant and Heteroresistant Mycobacterium tuberculosis by Use of Sloppy Molecular Beacons and Dual Melting-Temperature Codes in a Real-Time PCR Assay, Journal of Clinical Microbiology, Mar. 2011, vol. 49, No. 3, pp. 932-940.
Gundry, Cameron N., et al., Amplicon Melting Analysis with Labeled Primers: A Closed-Tube Method for Differentiating Homozygotes and Heterozygotes, Clinical Chemistry, 2003, vol. 49, No. 3, pp. 396-406.
Huang, Qiuying, et al., Multiplex Fluorescence Melting Curve Analysis for Mutation Detection with Dual-Labeled, Self- Quenched Probes, PLoS One, Apr. 2001, vol. 6, Issue 4, pp. 1-9.
International Search Report and Written Opinion, issued in PCT/KR2015/013460, dated Feb. 29, 2016.
International Search Report and Written Opinion, issued in PCT/KR2015/013461, dated Mar. 21, 2016.
Liu, Q., et al., Triplex real-time PCR melting curve analysis for detecting Mucobacterium tuberculosis mutations associated with resistance to second-line drugs in a single reaction; Journal of Antimicrobial Chemotherapy, 2013, vol. 68, pp. 1097-1103.
Pierce, K., et al., Rapid detection and identification of hepatitis C virus (HCV) sequences using mismatch-tolerant hybridization probes; A general method for analysis of sequence variation; Reports, 2013, vol. 55, No. 3, pp. 125-132.
Alvandi, E., et al., Zip nucleic acid: a new reliable method to increase the melting temperature of real-time PCR probes; Journal of Diabetes & Metabolic Disorders, 2014, vol. 13, pp. 1-4.

*Primary Examiner* — Jerry Lin
(74) *Attorney, Agent, or Firm* — Gianna Julian Arnold; Saul Ewing LLP

(57) ABSTRACT

The present invention relates to differentiating signals of interest for target nucleic acid sequences. The present invention permits to obtain an individual signal value (i.e., variable) contained in a total signal detected at detection temperatures by using mathematical equations. The present invention based on equation-solving approach enables to obtain the individual signal value in a systematical manner, thereby providing analysis results in much more accurate and convenient manner.

26 Claims, 21 Drawing Sheets

Specification includes a Sequence Listing.

[1] Template is genomic DNA of *Neisseria gonorrhoeae* (NG) and *Chlamydia trachomatis* (CT). NTC is No Template Control.

Fig. 1B

| Template[1] | End-RFU[2] | | Reference value[3] |
|---|---|---|---|
| | 60°C | 72°C | |
| NG | 997 | 547 | 1.8 |
| CT | 2177 | 375 | 5.8 |

[1] Template is genomic DNA of *Neisseria gonorrhoeae* (NG) and *Chlamydia trachomatis* (CT).
[2] End-RFU represents relative fluorescence units at 50th cycle.
[3] Reference value represents the ratio of End-RFU at 60°C to End-RFU at 72°C.

1) Template is genomic DNA of *Neisseria gonorrhoeae* (NG) and *Chlamydia trachomatis* (CT). NTC is No Template Control.
2) Equation set 1 and Simultaneous equation 1 were used to solve signals.
3) $S_{T1D1}$ is a variable representing a signal provided by NG (T1) at 60°C (D1).
4) $S_{T2D1}$ is a variable representing a signal provided by CT (T2) at 60°C (D1).

[1] Template is genomic DNA of *Neisseria gonorrhoeae* (NG) and *Chlamydia trachomatis* (CT). NTC is No Template Control.
[2] Equation set 1 and Simultaneous equation 2 were used to solve signals.
[3] $S_{T1D2}$ is a variable representing a signal provided by NG (T1) at 72°C (D2).
[4] $S_{T2D2}$ is a variable representing a signal provided by CT (T2) at 72°C (D2).

[1] Template is genomic DNA of *Neisseria gonorrhoeae* (NG) and *Chlamydia trachomatis* (CT). NTC is No Template Control.

Fig. 2B

| Template[1] | End-RFU[2] | | Reference value[3] |
|---|---|---|---|
| | 60°C | 72°C | |
| NG | 1787 | 48.7 | 36.7 |
| CT | 1839 | 1595 | 1.2 |

[1] Template is genomic DNA of *Neisseria gonorrhoeae* (NG) and *Chlamydia trachomatis* (CT).
[2] End-RFU represents relative fluorescence units at 50th cycle.
[3] Reference value represents the ratio of End-RFU at 60°C to End-RFU at 72°C.

1) Template is genomic DNA of *Neisseria gonorrhoeae* (NG) and *Chlamydia trachomatis* (CT). NTC is No Template Control.
2) Equation set 2 was used to solve signals.
3) $S_{T1D1}$ is a variable representing a signal provided by NG (T1) at 60°C (D1).
4) $S_{T2D1}$ is a variable representing a signal provided by CT (T2) at 60°C (D1).

[1] Template is genomic DNA of *Neisseria gonorrhoeae* (NG) and *Chlamydia trachomatis* (CT). NTC is No Template Control.
[2] Equation set 2 was used to solve signals.
[3] $S_{T1D2}$ is a variable representing a signal provided by NG (T1) at 72°C (D2).
[4] $S_{T2D2}$ is a variable representing a signal provided by CT (T2) at 72°C (D2).

[1] Template is genomic DNA of *Neisseria gonorrhoeae* (NG) and *Chlamydia trachomatis* (CT). NTC is No Template Control.
[2] Equation set 3 was used to solve signals.
[3] $S_{T1D1}$ is a variable representing a signal provided by NG (T1) at 60°C (D1).
[4] $S_{T2D1}$ is a variable representing a signal provided by CT (T2) at 60°C (D1).

1) Template is genomic DNA of *Neisseria gonorrhoeae* (NG) and *Chlamydia trachomatis* (CT). NTC is No Template Control.
2) Equation set 3 was used to solve signals.
3) $S_{T1D2}$ is a variable representing a signal provided by NG (T1) at 72°C (D2).
4) $S_{T2D2}$ is a variable representing a signal provided by CT (T2) at 72°C (D2).

1) Template is genomic DNA of *Neisseria gonorrhoeae* (NG) and *Chlamydia trachomatis* (CT). NTC is No Template Control.
2) Equation set 4 was used to solve signals.
3) $S_{T1D1}$ is a variable representing a signal provided by NG (T1) at 60°C (D1).
4) $S_{T2D1}$ is a variable representing a signal provided by CT (T2) at 60°C (D1).

1) Template is genomic DNA of *Neisseria gonorrhoeae* (NG) and *Chlamydia trachomatis* (CT). NTC is No Template Control.
2) Equation set 4 was used to solve signals.
3) $S_{T1D2}$ is a variable representing a signal provided by NG (T1) at 72°C (D2).
4) $S_{T2D2}$ is a variable representing a signal provided by CT (T2) at 72°C (D2).

[1] Template is genomic DNA of *Neisseria gonorrhoeae* (NG), *Chlamydia trachomatis* (CT) and *Mycoplasma genitalium* (MG).

Fig. 3C

| Template[1] | End-RFU[2] | | Reference value[3] |
|---|---|---|---|
| | 60°C | 72°C | |
| NG | 1926 | 9.29 | 207.3 |
| CT | 1738 | 1403 | 1.2 |
| MG | 5107 | 4333 | 1.2 |

| Template | End-RFU | | Reference value[4] |
|---|---|---|---|
| | 60°C | 95°C | |
| NG | 1926 | -9.38 | -205.3 |
| CT | 1738 | 6.82 | 254.8 |
| MG | 5107 | 3816 | 1.3 |

| Template | End-RFU | | Reference value[5] |
|---|---|---|---|
| | 72°C | 95°C | |
| NG | 9.29 | -9.38 | -1.0 |
| CT | 1403 | 6.82 | 205.7 |
| MG | 4333 | 3816 | 1.1 |

[1] Template is genomic DNA of *Neisseria gonorrhoeae* (NG), *Chlamydia trachomatis* (CT) and *Mycoplasma genitalium* (MG).
[2] End-RFU represents relative fluorescence units at 50th cycle.
[3] Reference value represents the ratio of End-RFU at 60°C to End-RFU at 72°C.
[4] Reference value represents the ratio of End-RFU at 60°C to End-RFU at 95°C.
[5] Reference value represents the ratio of End-RFU at 72°C to End-RFU at 95°C.

Fig. 3D

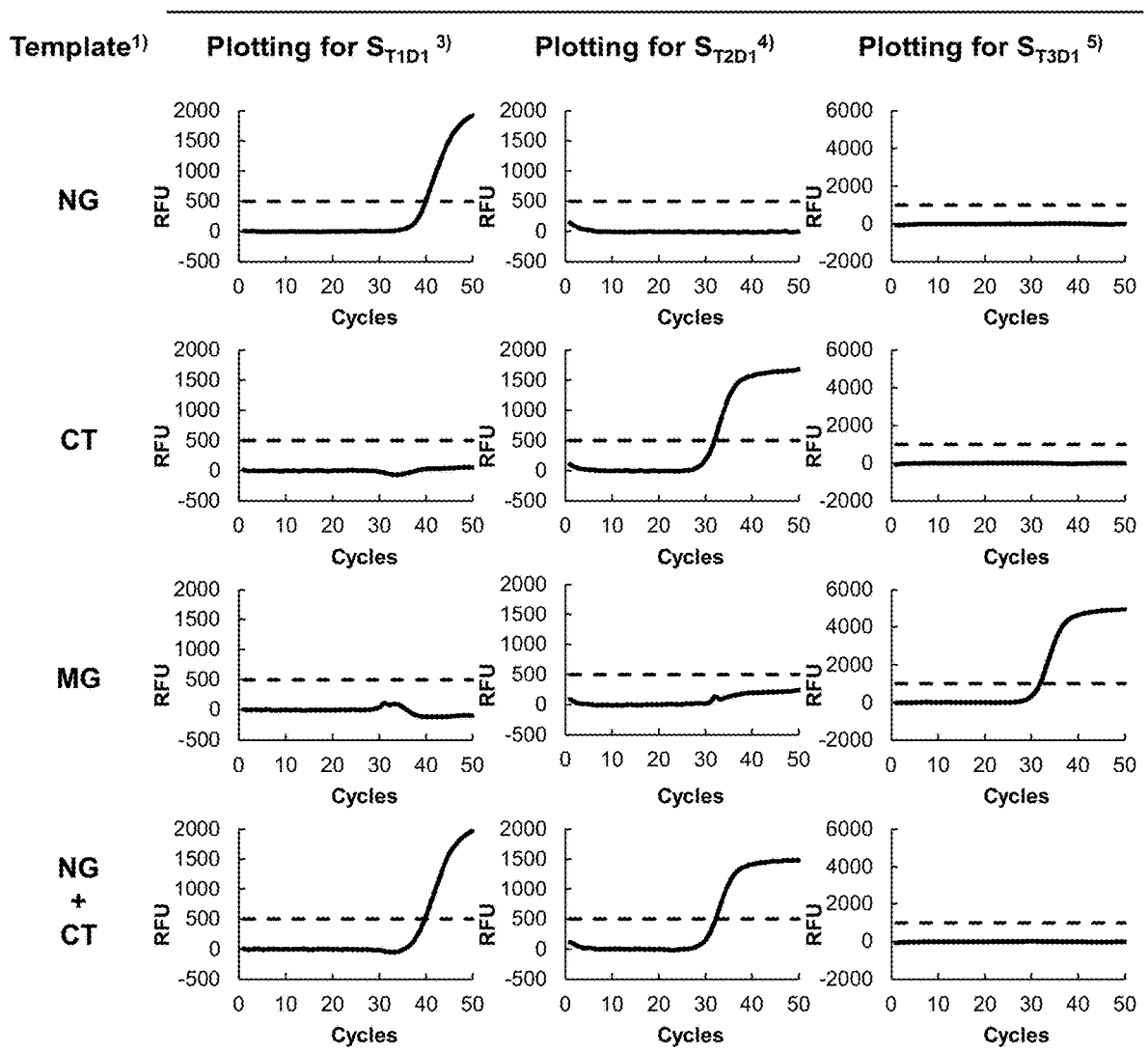

[1] Template is genomic DNA of *Neisseria gonorrhoeae* (NG), *Chlamydia trachomatis* (CT) and *Mycoplasma genitalium* (MG).
[2] Equation set 5 and Simultaneous equation 5 were used to solve signals.
[3] $S_{T1D1}$ is a variable representing a signal provided by NG (T1) at 60°C (D1).
[4] $S_{T2D1}$ is a variable representing a signal provided by CT (T2) at 60°C (D1).
[5] $S_{T3D1}$ is a variable representing a signal provided by MG (T3) at 60°C (D1).

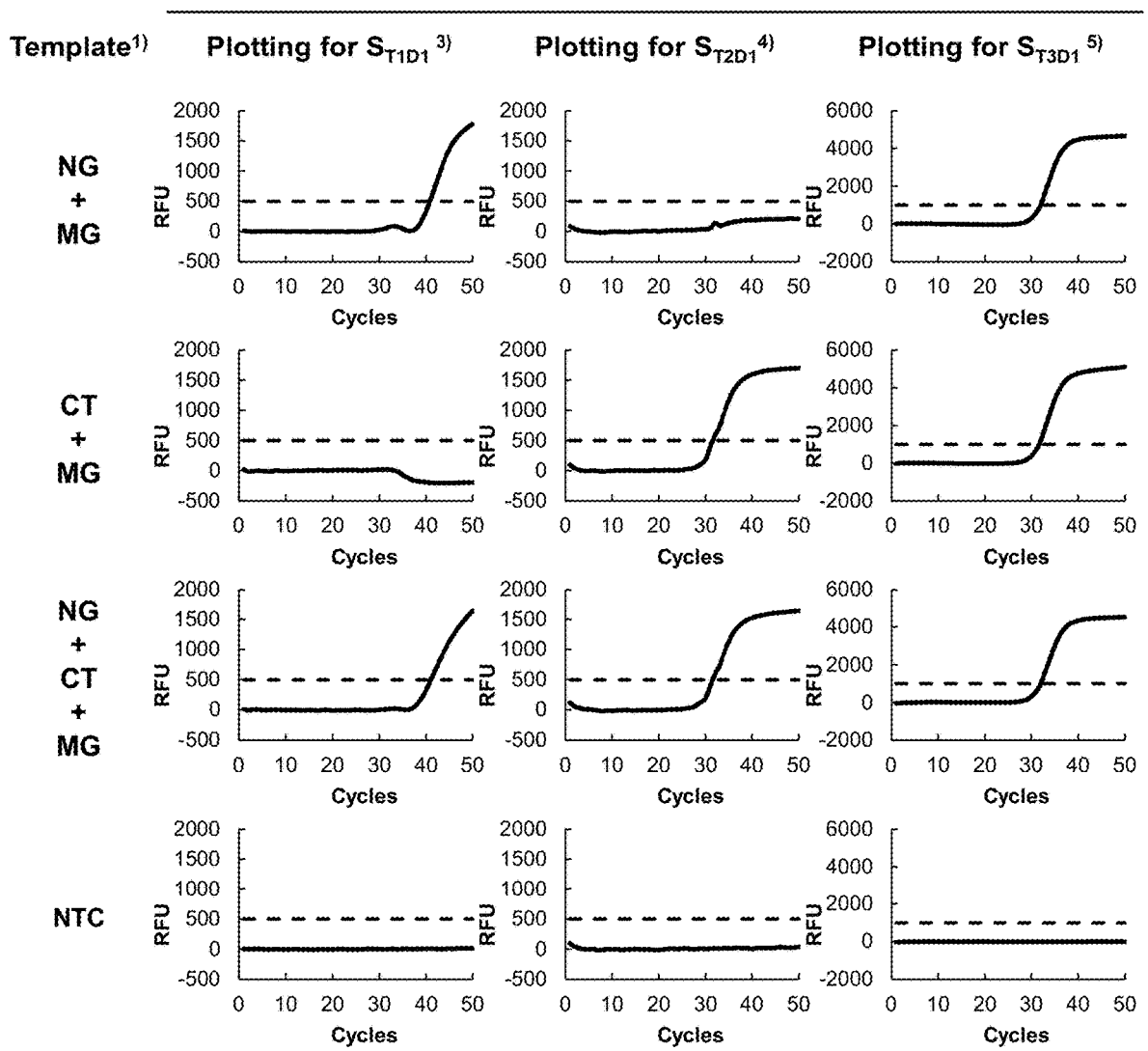

Fig. 3E

Differentiation of signals detected at 60°C[2]

1) Template is genomic DNA of *Neisseria gonorrhoeae* (NG), *Chlamydia trachomatis* (CT) and *Mycoplasma genitalium* (MG). NTC is No Template Control.
2) Equation set 5 and Simultaneous equation 5 were used to solve signals.
3) $S_{T1D1}$ is a variable representing a signal provided by NG (T1) at 60°C (D1).
4) $S_{T2D1}$ is a variable representing a signal provided by CT (T2) at 60°C (D1).
5) $S_{T3D1}$ is a variable representing a signal provided by MG (T3) at 60°C (D1).

Fig. 3F

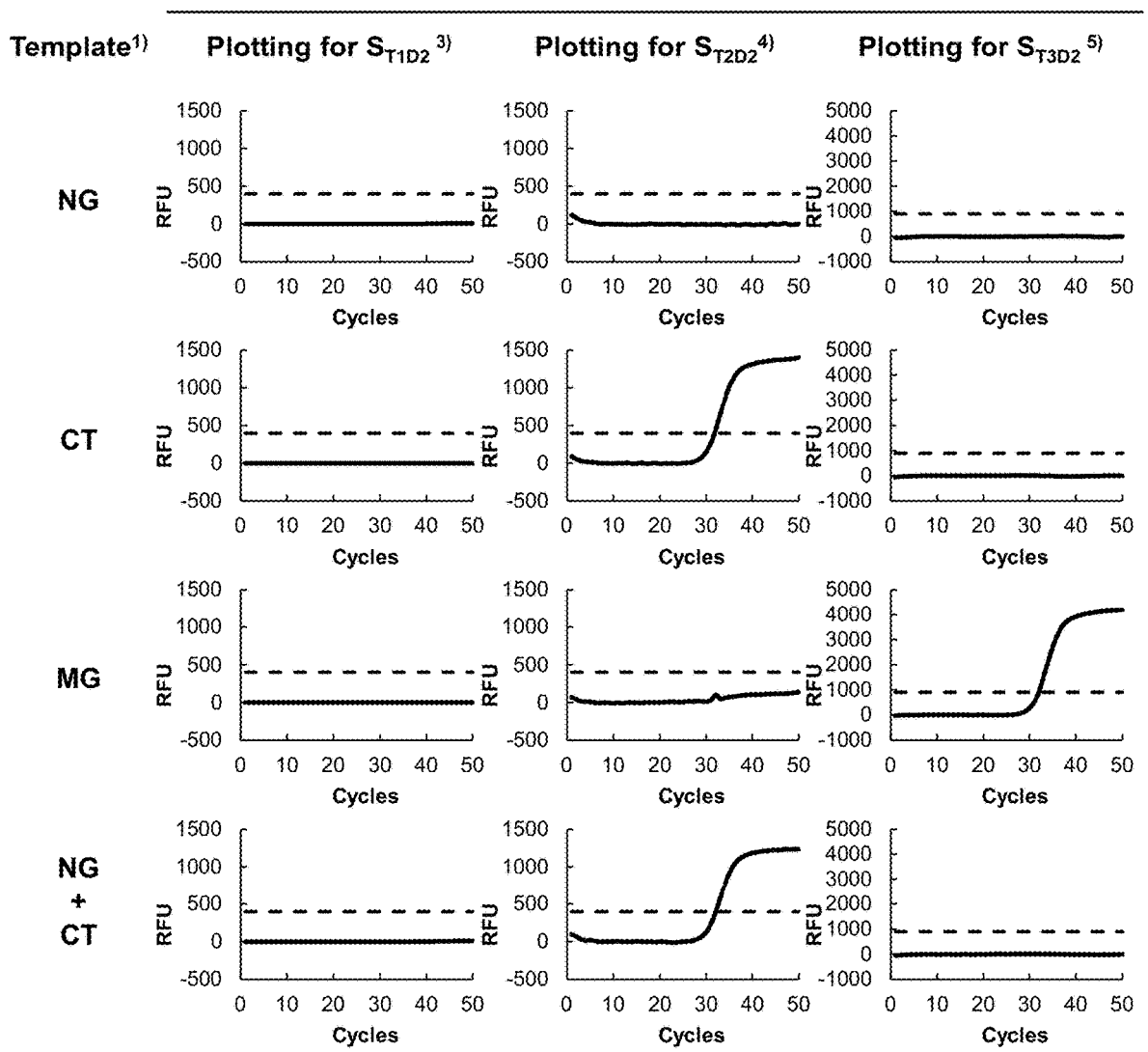

1) Template is genomic DNA of *Neisseria gonorrhoeae* (NG), *Chlamydia trachomatis* (CT) and *Mycoplasma genitalium* (MG).
2) Equation set 5 and Simultaneous equation 6 were used to solve signals.
3) $S_{T1D2}$ is a variable representing a signal provided by NG (T1) at 72°C (D2).
4) $S_{T2D2}$ is a variable representing a signal provided by CT (T2) at 72°C (D2).
5) $S_{T3D2}$ is a variable representing a signal provided by MG (T3) at 72°C (D2).

Fig. 3G

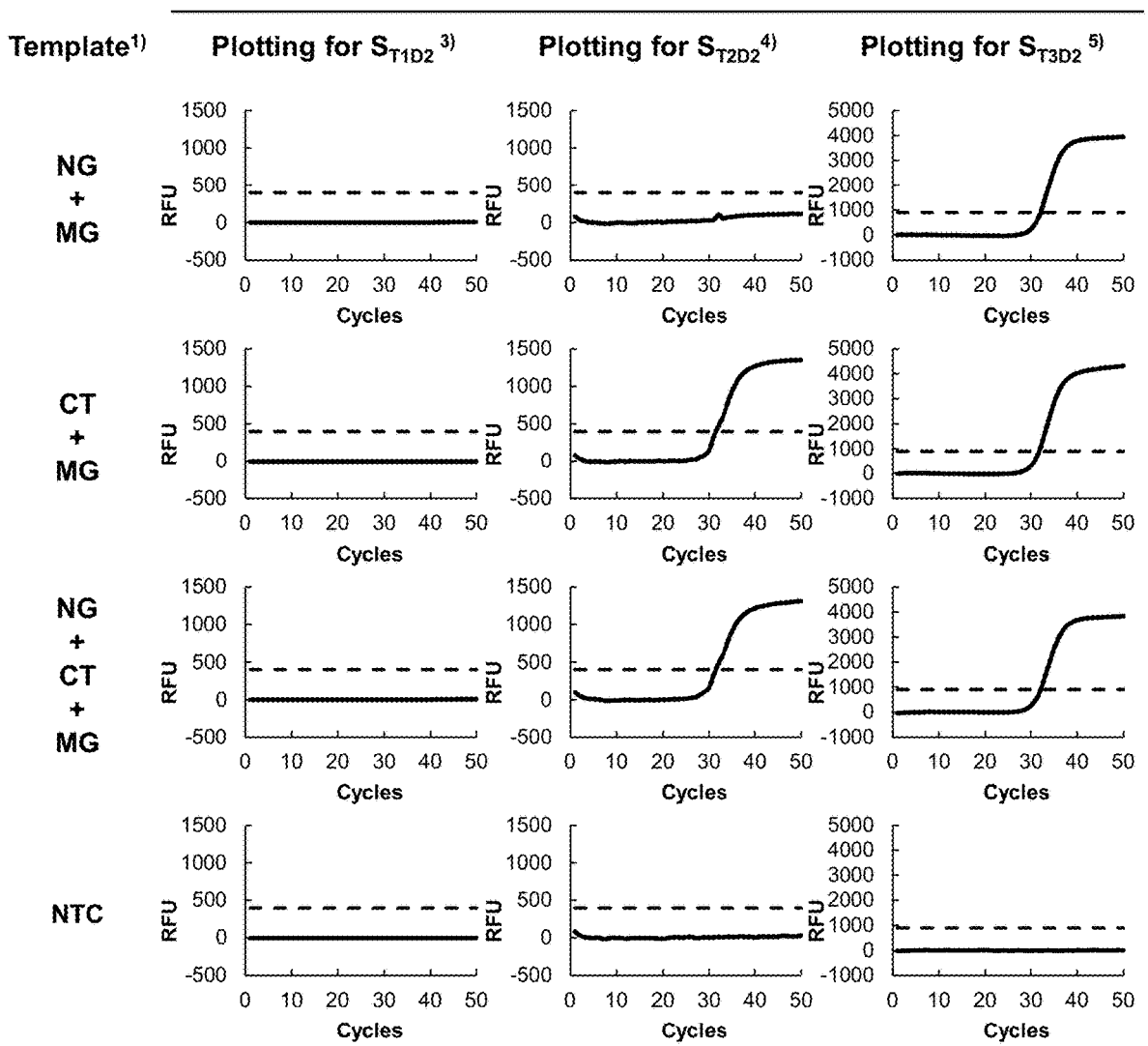

Differentiation of signals detected at 72°C[2]

1) Template is genomic DNA of *Neisseria gonorrhoeae* (NG), *Chlamydia trachomatis* (CT) and *Mycoplasma genitalium* (MG). NTC is No Template Control.
2) Equation set 5 and Simultaneous equation 6 were used to solve signals.
3) $S_{T1D2}$ is a variable representing a signal provided by NG (T1) at 72°C (D2).
4) $S_{T2D2}$ is a variable representing a signal provided by CT (T2) at 72°C (D2).
5) $S_{T3D2}$ is a variable representing a signal provided by MG (T3) at 72°C (D2).

Fig. 3H

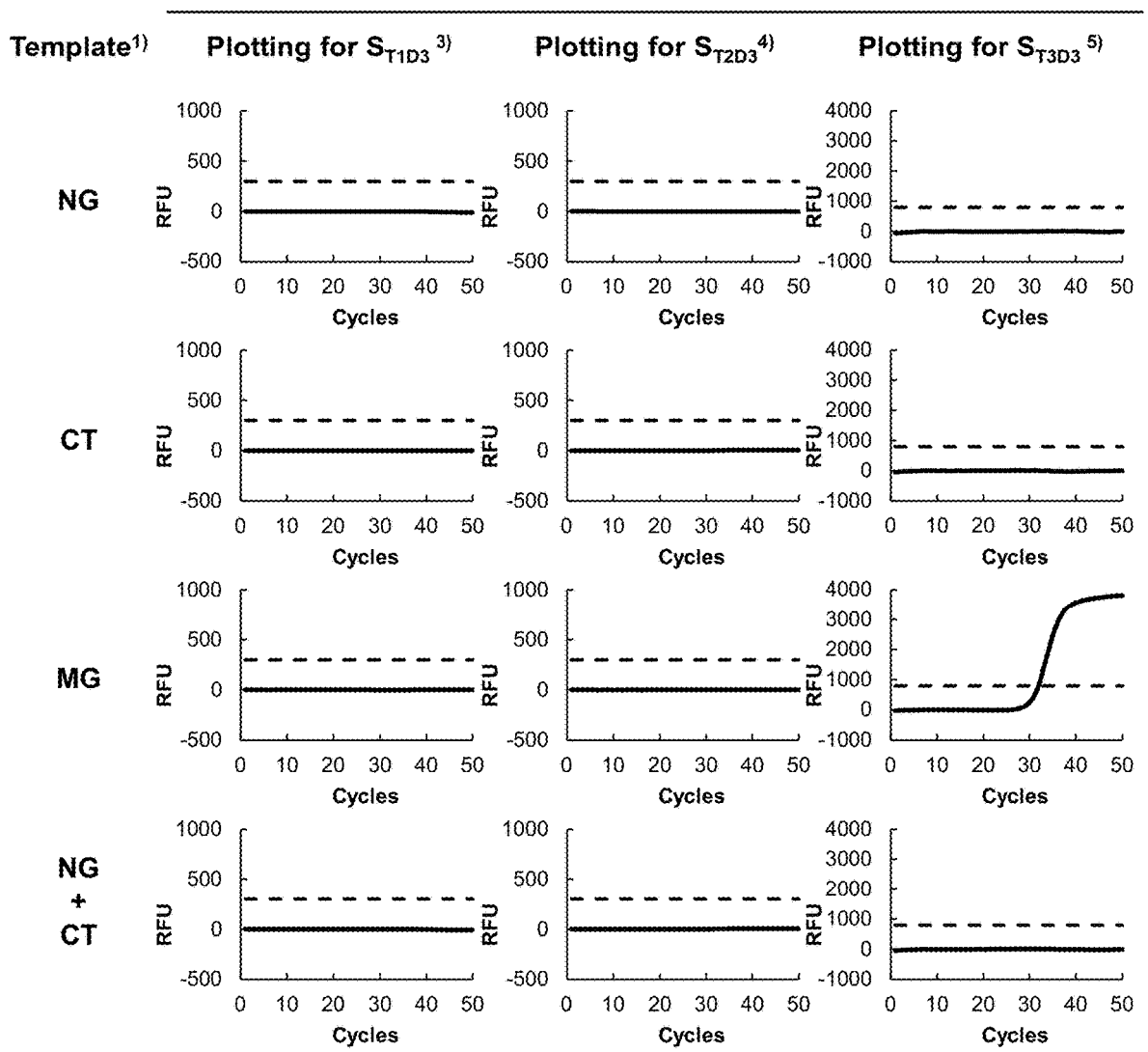

1) Template is genomic DNA of *Neisseria gonorrhoeae* (NG), *Chlamydia trachomatis* (CT) and *Mycoplasma genitalium* (MG).
2) Equation set 5 and Simultaneous equation 7 were used to solve signals.
3) $S_{T1D3}$ is a variable representing a signal provided by NG (T1) at 95°C (D3).
4) $S_{T2D3}$ is a variable representing a signal provided by CT (T2) at 95°C (D3).
5) $S_{T3D3}$ is a variable representing a signal provided by MG (T3) at 95°C (D3).

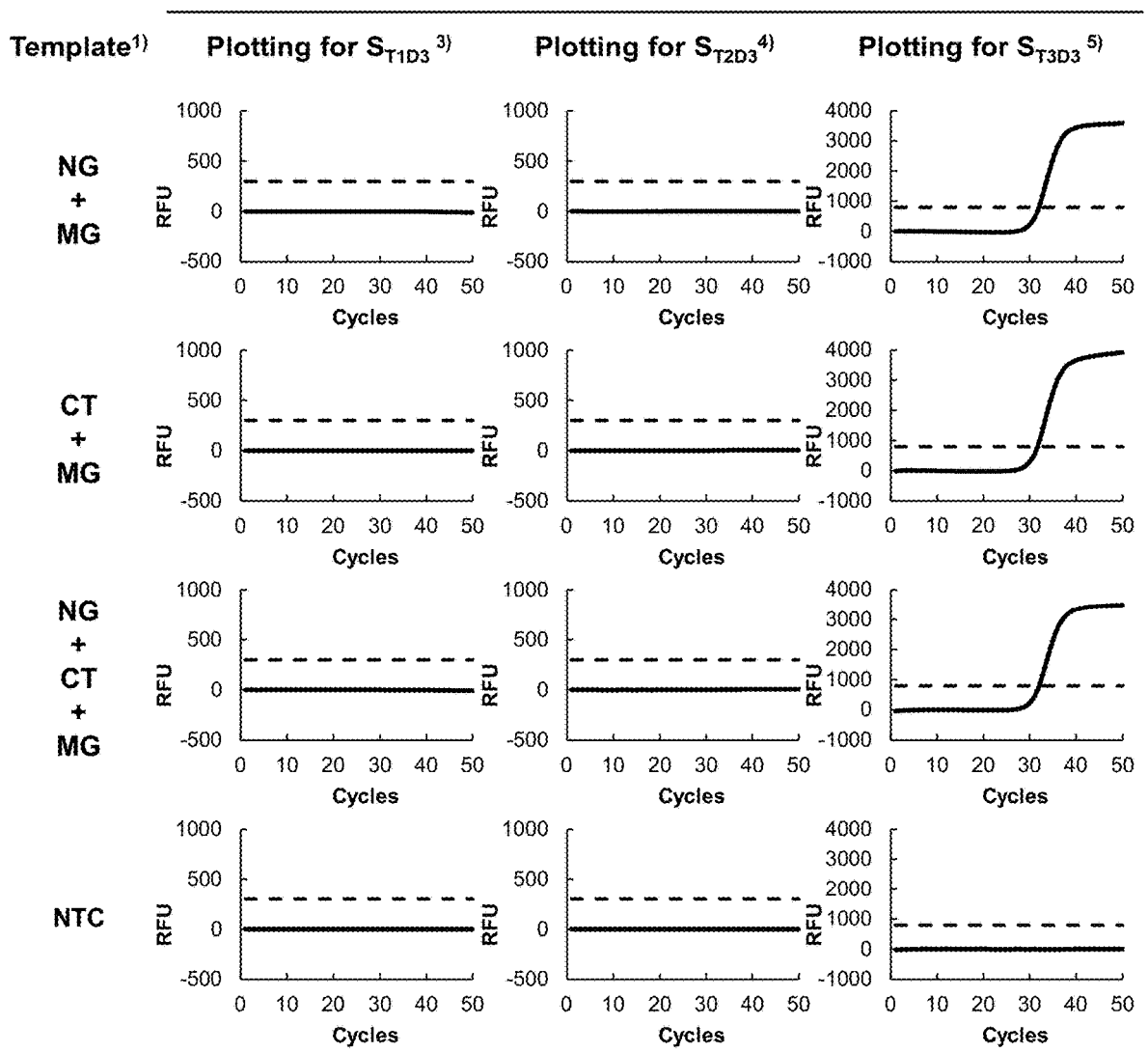

Fig. 3I

Differentiation of signals detected at 95°C [2]

1) Template is genomic DNA of *Neisseria gonorrhoeae* (NG), *Chlamydia trachomatis* (CT) and *Mycoplasma genitalium* (MG). NTC is No Template Control.
2) Equation set 5 and Simultaneous equation 7 were used to solve signals.
3) $S_{T1D3}$ is a variable representing a signal provided by NG (T1) at 95°C (D3).
4) $S_{T2D3}$ is a variable representing a signal provided by CT (T2) at 95°C (D3).
5) $S_{T3D3}$ is a variable representing a signal provided by MG (T3) at 95°C (D3).

SEQUENCE LISTING

<160> NUMBER OF SEQ ID NOS: 15

<210> SEQ ID NO 1
<211> LENGTH: 37
<212> TYPE: DNA
<213> ORGANISM: Artificial Sequence
<220> FEATURE:
<223> OTHER INFORMATION: NG-F
<220> FEATURE:
<221> NAME/KEY: misc_feature
<222> LOCATION: (22)..(26)
<223> OTHER INFORMATION: n denotes deoxyinosine

<400> SEQUENCE: 1
tacgcctgct actttcacgc tnnnnngtaa tcagatg                              37

<210> SEQ ID NO 2
<211> LENGTH: 37
<212> TYPE: DNA
<213> ORGANISM: Artificial Sequence
<220> FEATURE:
<223> OTHER INFORMATION: NG-R
<220> FEATURE:
<221> NAME/KEY: misc_feature
<222> LOCATION: (22)..(26)
<223> OTHER INFORMATION: n denotes deoxyinosine

<400> SEQUENCE: 2
caatggatcg gtatcactcg cnnnnncgag caagaac                              37

<210> SEQ ID NO 3
<211> LENGTH: 22
<212> TYPE: DNA
<213> ORGANISM: Artificial Sequence
<220> FEATURE:
<223> OTHER INFORMATION: NG-P

<400> SEQUENCE: 3
tgcccctcat tggcgtgttt cg                                              22

<210> SEQ ID NO 4
<211> LENGTH: 36
<212> TYPE: DNA
<213> ORGANISM: Artificial Sequence
<220> FEATURE:
<223> OTHER INFORMATION: CT-F1
<220> FEATURE:
<221> NAME/KEY: misc_feature
<222> LOCATION: (22)..(26)
<223> OTHER INFORMATION: n denotes deoxyinosine

<400> SEQUENCE: 4
tccgaatgga taaagcgtga cnnnnnatga actcac                               36

<210> SEQ ID NO 5
<211> LENGTH: 37
<212> TYPE: DNA
<213> ORGANISM: Artificial Sequence
<220> FEATURE:
<223> OTHER INFORMATION: CT-R1
<220> FEATURE:
<221> NAME/KEY: misc_feature
<222> LOCATION: (23)..(27)
<223> OTHER INFORMATION: n denotes deoxyinosine

<400> SEQUENCE: 5
aacaatgaat cctgagcaaa ggnnnnncgt tagagtc                              37

```
<210> SEQ ID NO 6
<211> LENGTH: 29
<212> TYPE: DNA
<213> ORGANISM: Artificial Sequence
<220> FEATURE:
<223> OTHER INFORMATION: CT-P

<400> SEQUENCE: 6
cattgtaaag atatggtctg cttcgaccg                                    29

<210> SEQ ID NO 7
<211> LENGTH: 34
<212> TYPE: DNA
<213> ORGANISM: Artificial Sequence
<220> FEATURE:
<223> OTHER INFORMATION: NG-PTO

<400> SEQUENCE: 7
gtacgcgata cgggcccctc attggcgtgt ttcg                              34

<210> SEQ ID NO 8
<211> LENGTH: 39
<212> TYPE: DNA
<213> ORGANISM: Artificial Sequence
<220> FEATURE:
<223> OTHER INFORMATION: NG-CTO

<400> SEQUENCE: 8
tttttttttt ttttttttttg tactgcccgt atcgcgtac                        39

<210> SEQ ID NO 9
<211> LENGTH: 40
<212> TYPE: DNA
<213> ORGANISM: Artificial Sequence
<220> FEATURE:
<223> OTHER INFORMATION: CT-F2
<220> FEATURE:
<221> NAME/KEY: misc_feature
<222> LOCATION: (26)..(30)
<223> OTHER INFORMATION: n denotes deoxyinosine

<400> SEQUENCE: 9
gagttttaaa atgggaaatt ctggtnnnnn tttgtataac                        40

<210> SEQ ID NO 10
<211> LENGTH: 40
<212> TYPE: DNA
<213> ORGANISM: Artificial Sequence
<220> FEATURE:
<223> OTHER INFORMATION: CT-R2
<220> FEATURE:
<221> NAME/KEY: misc_feature
<222> LOCATION: (26)..(30)
<223> OTHER INFORMATION: n denotes deoxyinosine

<400> SEQUENCE: 10
ccaattgtaa tagaagcatt ggttgnnnnn ttattggaga                        40

<210> SEQ ID NO 11
<211> LENGTH: 39
<212> TYPE: DNA
<213> ORGANISM: Artificial Sequence
<220> FEATURE:
<223> OTHER INFORMATION: CT-PTO

<400> SEQUENCE: 11
gattacgcga ccgcatcaga agctgtcatt ttggctgcg                         39
```

```
<210> SEQ ID NO 12
<211> LENGTH: 39
<212> TYPE: DNA
<213> ORGANISM: Artificial Sequence
<220> FEATURE:
<223> OTHER INFORMATION: CT-CTO

<400> SEQUENCE: 12
gcgctggata ccctggacga tatgtgcggt cgcgtaatc                              39

<210> SEQ ID NO 13
<211> LENGTH: 38
<212> TYPE: DNA
<213> ORGANISM: Artificial Sequence
<220> FEATURE:
<223> OTHER INFORMATION: MG-F
<220> FEATURE:
<221> NAME/KEY: misc_feature
<222> LOCATION: (23)..(27)
<223> OTHER INFORMATION: n denotes deoxyinosine

<400> SEQUENCE: 13
aaaacccacg gaaatgatga gannnnnatt ggttctac                               38

<210> SEQ ID NO 14
<211> LENGTH: 41
<212> TYPE: DNA
<213> ORGANISM: Artificial Sequence
<220> FEATURE:
<223> OTHER INFORMATION: MG-R
<220> FEATURE:
<221> NAME/KEY: misc_feature
<222> LOCATION: (27)..(31)
<223> OTHER INFORMATION: n denotes deoxyinosine

<400> SEQUENCE: 14
ctcgttaatt tacctattcc attttgnnnn nctgataaaa g                           41

<210> SEQ ID NO 15
<211> LENGTH: 28
<212> TYPE: DNA
<213> ORGANISM: Artificial Sequence
<220> FEATURE:
<223> OTHER INFORMATION: MG-P

<400> SEQUENCE: 15
gagttctttc aagaacagca agaggtgt                                          28
```

DIFFERENTIATION OF SIGNALS FOR TARGET NUCLEIC ACID SEQUENCES

CROSS-REFERENCE TO RELATED APPLICATIONS

This application is a continuation of and claims priority to U.S. application Ser. No. 15/534,643, filed Jun. 9, 2017, which claims the priority of PCT/KR2015/013461, filed on Dec. 9, 2015, which claims priority to U.S. Patent Application No. 62/154,319, filed on Apr. 29, 2015, which claims priority to U.S. Patent Application No. 62/089,723, filed on Dec. 9, 2014, the entire contents of each of which are hereby incorporated in total by reference.

SEQUENCE

This application incorporates by reference the Sequence Listing contained in an ASCII text file named "361406 00048 SeqList.txt" submitted via EFS-Web. The text file was created on Dec. 22, 2020, and is 3.64 kb in size.

BACKGROUND OF THE INVENTION

Field of the Invention

The present invention relates to differentiating signals of interest for target nucleic acid sequences.

Description of the Related Art

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v.14 MARCH 1996), HyBeacon method (French D J et al., Mol. Cell Probes, 15(6):363-374 (2001)), Hybridization probe method using two probes labeled each of donor and acceptor (Bernad et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v.25 no. 12, and U.S. Pat. No. 6,117,635), Scorpion primer method (Whitcombe et al, 804-807, Nature Biotechnology v.17 Aug. 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH(PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312).

The conventional real-time detection technologies described above detect signals generated from fluorescent labels at a selected detection temperature in signal amplification process associated with or with no target amplification. When a plurality of target nucleic acid sequences using a single type of label in a single reaction tube are detected in accordance with the conventional real-time detection technologies, generated signals for target nucleic acid sequences are not differentiated from each other. Therefore, the conventional real-time detection technologies generally employ different types of labels for detecting a plurality of target nucleic acid sequences. The melting analysis using $T_m$ difference permits to detect a plurality of target nucleic acid sequences even a single type of label. However, the melting analysis has serious shortcomings in that its performance time is longer than real-time technologies and design of probes with different $T_m$ values becomes more difficult upon increasing target sequences.

Accordingly, where novel methods or approaches being not dependent on melting analysis for detecting a plurality of target nucleic acid sequences using a single type of label in a single reaction vessel and a single type of detector are developed, they enable to detect a plurality of target nucleic acid sequences with dramatically enhanced convenience, cost-effectiveness and efficiency. In addition, the combination of the novel methods with other detection methods (e.g., melting analysis) would result in detection of a plurality of target nucleic acid sequences using a single type of label in a single reaction vessel with dramatically enhanced efficiency.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel methods for qualitatively or quantitatively detecting a target nucleic acid sequence, particularly a plurality of target nucleic acid sequences in more accurate and convenient manner. As a result, we have found that signals for target nucleic acid sequences are obtained at detection temperatures and then detection results are processed by using suitable equations, thereby enabling to detect a plurality of target nucleic acid sequences even using a single type of label in a single reaction vessel and a single type of detector with dramatically enhanced convenience, cost-effectiveness and efficiency.

Accordingly, it is an object of this invention to provide a method and a kit for differentiating signals of interest for each of two target nucleic acid sequences comprising a first target nucleic acid sequence (T1) and a second target nucleic acid sequence (T2) in a sample, which are not differentiable by a single type of detector.

It is another object of this invention to provide a method and a kit for differentiating signals of interest for each of target nucleic acid sequences in the number of N in a sample, which are not differentiable by a single type of detector.

It is still another object of this invention to provide a computer readable storage medium containing instructions to configure a processor to perform a method for differentiating signals of interest for each of two target nucleic acid sequences comprising a first target nucleic acid sequence (T1) and a second target nucleic acid sequence (T2) in a sample, which are not differentiable by a single type of detector.

It is further object of this invention to provide a computer readable storage medium containing instructions to configure a processor to perform a method for differentiating signals of interest for each of target nucleic acid sequences in the number of N in a sample, which are not differentiable by a single type of detector.

It is still further object of this invention to provide a device for differentiating signals of interest for each of two target nucleic acid sequences comprising a first target nucleic acid sequence (T1) and a second target nucleic acid sequence (T2) in a sample, which are not differentiable by a single type of detector.

It is another object of this invention to provide a device for differentiating signals of interest for each of target nucleic acid sequences in the number of N in a sample, which are not differentiable by a single type of detector.

It is still another object of this invention to provide a computer program to be stored on a computer readable storage medium to configure a processor to perform a method for differentiating signals of interest for each of two target nucleic acid sequences comprising a first target nucleic acid sequence (T1) and a second target nucleic acid sequence (T2) in a sample, which are not differentiable by a single type of detector.

It is further object of this invention to provide a computer program to be stored on a computer readable storage medium to configure a processor to perform a method for differentiating signals of interest for each of target nucleic acid sequences in the number of N in a sample, which are not differentiable by a single type of detector.

Other objects and advantages of the present invention will become apparent from the detailed description to follow taken in conjugation with the appended claims and drawings.

BRIEF DESCRIPTION OF THE DRAWINGS

FIG. 1B represents obtaining reference values based on the detection results of FIG. 1A. The ratio of the signal at the first detection temperature to the signal at the second detection temperature is one of exemplified reference values.

FIG. 2B represents obtaining reference values based on the detection results of FIG. 2A. The ratio of the signal at the first detection temperature to the signal at the second detection temperature is one of exemplified reference values.

FIG. 3C represents obtaining reference values based on the detection results of FIG. 3A. The ratio of the signal between detection temperatures is one of exemplified reference values.

FIGS. 3D and 3E represents plotting results for $S_{T1D1}$, $S_{T2D1}$ and $S_{T3D1}$ obtained by solving the simultaneous equation 5. Experimentally obtained reference values were used. The dotted line represents a threshold which was determined with referring to the result of NG only sample, CT only sample and MG only sample in FIG. 3A to verify the significance of the obtained amplification curves.

FIGS. 3F and 3G represents plotting results for $S_{T1D2}$, $S_{T2D2}$ and $S_{T3D2}$ obtained by solving the simultaneous equation 6. Experimentally obtained reference values were used. The dotted line represents a threshold.

FIGS. 3H and 3I represents plotting results for $S_{T1D3}$, $S_{T2D3}$ and $S_{T3D3}$ obtained by solving the simultaneous equation 7. Experimentally obtained reference values were used. The dotted line represents a threshold.

DETAILED DESCRIPTION OF THIS INVENTION

Figure 1A:
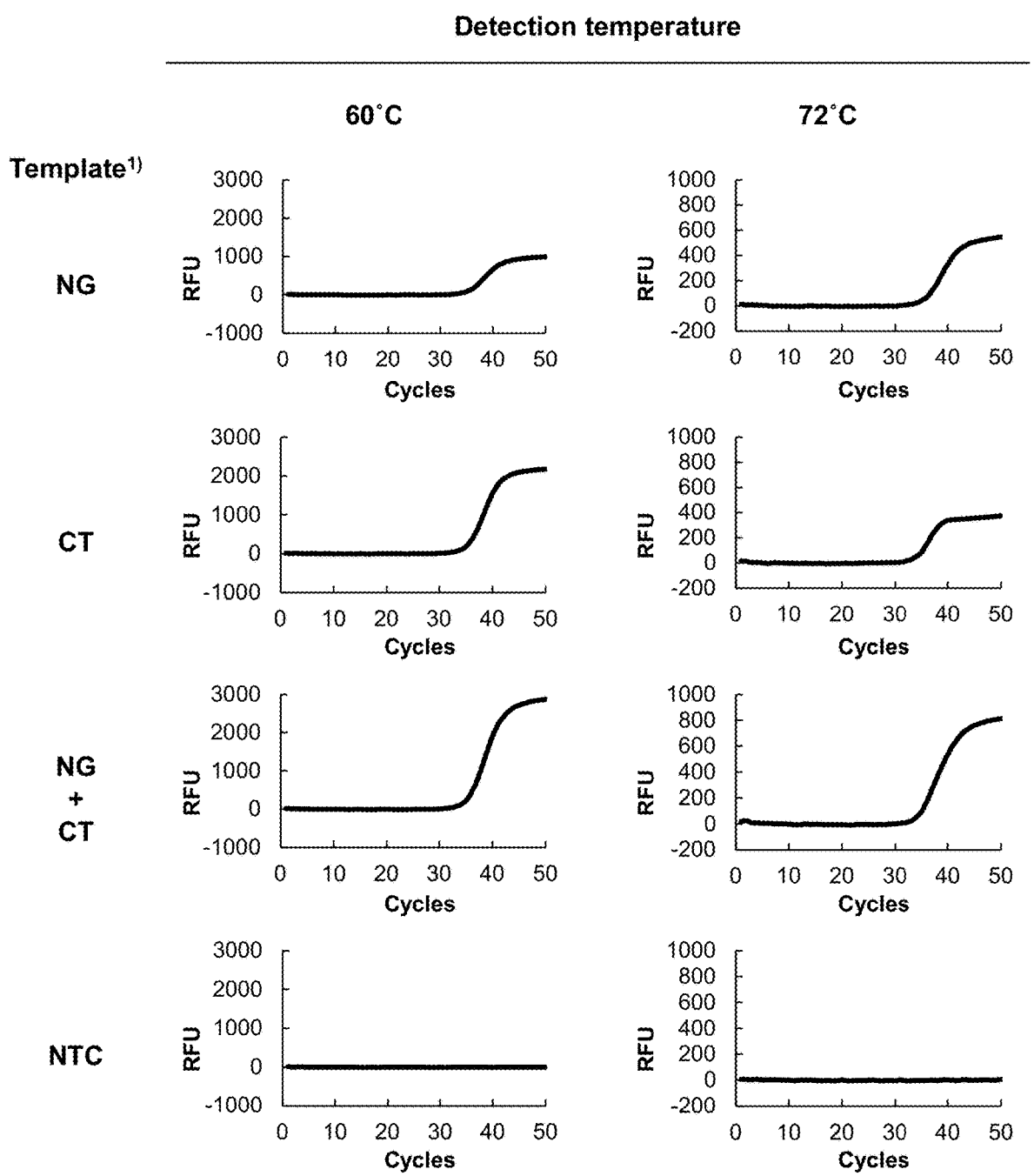
FIG. 1A represents the detection results of a first target nucleic acid sequence (genome DNA of *Neisseria gonorrhoeae*, NG), a second target nucleic acid sequence (genome DNA of *Chlamydia trachomatis*, CT) and their combination at a first detection temperature (60° C.) and a second detection temperature (72° C.). The signals for NG and CT were generated by the TaqMan probe method. NTC denotes no template control.

The most prominent feature of the present invention is detect a plurality of target nucleic acid sequences even using a single type of label and a single type of detector in a signal reaction vessel. The present invention employing different detection temperatures and mathematical equations for solving variables enables to detect a plurality of target nucleic acid sequences even with a single type of label in a single reaction vessel. The elements of the present invention are selected in compliance with the feature of the present invention and fabricated into a surprising process for detect target nucleic acid sequences.

Conventional real-time PCR methods require two types of fluorescent labels or melting analysis for detection of two target nucleic acid sequences in a single reaction vessel.

The present invention permits real-time PCR protocols to detect two target nucleic acid sequences even using a single type of fluorescent label in a single reaction vessel.

I. Differentiation of Signals of Interest for Two Target Nucleic Acid Sequences

In one aspect of this invention, there is provided a method for differentiating signals of interest for each of two target nucleic acid sequences comprising a first target nucleic acid sequence (T1) and a second target nucleic acid sequence (T2) in a sample, which are not differentiable by a single type of detector, comprising:

(a) incubating the sample with a first signal-generating means for detection of the first target nucleic acid sequence (T1) and a second signal-generating means for detection of the second target nucleic acid sequence (T2) and detecting signals at a first detection temperature (D1) and a second detection temperature (D2); wherein the signals of interest to be generated by the two signal-generating means are not differentiated for each target nucleic acid sequence by a single type of detector;

(b) providing the following two equations each of which comprises variables representing the signals of interest generated at each detection temperature for the two target nucleic acid sequences;

$$S_{T1D1} + S_{T2D1} = S_{D1} \quad (I)$$

$$S_{T1D2} + S_{T2D2} = S_{D2} \quad (II)$$

wherein ($S_{D1}$) is a signal detected at the first detection temperature, ($S_{D2}$) is a signal detected at the second detection temperature; ($S_{T1D1}$) is a variable representing a signal of interest generated by the first signal-generating means at the first detection temperature, ($S_{T2D1}$) is a variable representing a signal of interest generated by the second signal-generating means at the first detection temperature, ($S_{T1D2}$) is a variable representing a signal of interest generated by the first signal-generating means at the second detection temperature, ($S_{T2D2}$) is a variable representing a signal of interest generated by the second signal-generating means at the second detection temperature; and the total number of variables is four;

(c) providing two additional equations each of which comprises at least one variable selected from the group consisting of the four variables, ($S_{T1D1}$), ($S_{T2D1}$), ($S_{T1D2}$) and ($S_{T2D2}$); and (d) obtaining solutions to at least one of the variables by the four equations provided in the steps (b) and (c) for differentiating at least one of the signals of interest to be assigned to at least one of the two target nucleic acid sequences.

According to conventional real-time PCR methods using amplification curves, it is common knowledge in the art that a plurality of target nucleic acid sequences cannot be differentially detected by use of signal-generating means providing undistinguishable identical signals.

The present invention overcomes limitations associated with the common knowledge in the art and leads to unexpected results to detect target nucleic acid sequences in greatly improved manner.

The present method is expressed herein as a method for differentiating signals of interest for each of two target nucleic acid sequences in a sample and alternatively may be expressed as a method for detecting at least one of two target nucleic acid sequences in a sample or a method for determining the presence of at least one of two target nucleic acid sequences in a sample by assigning at least one of signals of interest to at least one of the two target nucleic acid sequences.

The term used herein "signal of interest" refers to a signal to be differentiated by the present invention. The signal finally detected may be a sum of a plurality of signals. For example, the signal finally detected at a detection temperature may include (i) a signal from a first signal-generating means for a first target nucleic acid sequence (T1) and (ii) a signal from a second signal-generating means for a second target nucleic acid sequence (T2). Each of (i) the signal and (ii) the signal is the signal of interest to be differentiated by the present invention. For example, the present invention aims to differentiating (i) the signal and/or (ii) the signal from the detected signal. Such differentiation of the signal of interest permits to assign the signal of interest to at least one of the two target nucleic acid sequences. As a result, the differentiation of the signal of interest allows for determination whether the target nucleic acid sequences are present or absent in the sample.

According to conventional technologies, the signals of interest to be generated by the two signal-generating means are not differentiated for each target nucleic acid sequence. Interestingly, the present invention enables to differentiate the signals of interest to be generated by the two signal-generating means such that the signals of interest are assigned to the two target nucleic acid sequences even using a single type of detector.

Furthermore, the present invention permits to differentiate the signals of interest by using mathematical equations in much more systematical, reliable, convenient manner.

The present invention will be described in more detail as follows:

Step (a): Incubating Samples with Signal-Generating Means and Signal Detection

The sample to be analyzed is incubated with a first signal-generating means for detection of the first target nucleic acid sequence (T1) and a second signal-generating means for detection of the second target nucleic acid sequence (T2) and then signals from the two signal-generating means are detected at a first detection temperature (D1) and a second detection temperature (D2); wherein the signals of interest to be generated by the two signal-generating means are not differentiated for each target nucleic acid sequence by a single type of detector.

The present invention utilizes signal-generating means for providing signals for target nucleic acid sequences. Each of the target nucleic acid sequences is detected by a corresponding signal-generating means.

The term used herein "signal-generating means" refers to any material used in generation of signals indicating the presence of target nucleic acid sequences, for example including oligonucleotides, labels and enzymes. Alternatively, the term used herein "signal-generating means" can be used to refer to any methods using the materials for signal generation.

According to an embodiment of this invention, the incubation is preformed under conditions allowing a signal generation by the signal-generation means. Such conditions include temperatures, salt concentrations and pH of solutions.

Examples of the oligonucleotides serving as signal-generating means include oligonucleotides to be specifically hybridized with target nucleic acid sequences (e.g., probes and primers); where probes or primers hybridized with target nucleic acid sequences are cleaved to release a fragment, the oligonucleotides serving as signal-generating means include capture oligonucleotides to be specifically hybridized with the fragment; where the fragment hybridized with the capture oligonucleotide is extended to form an extended strand, the oligonucleotides serving as signal-generating means include oligonucleotides to be specifically hybridized with the extended strand; the oligonucleotides serving as signal-generating means include oligonucleotides to be specifically hybridized with the capture oligonucleotide; and the oligonucleotides serving as signal-generating means include combinations thereof.

While a signal generation principle is the same, the signal generating means comprising different sequences of oligonucleotides used may be considered different from each other.

The label may be linked to oligonucleotides or may be in the free form. The label may be incorporated into extended products during an extension reaction.

Where the cleavage of oligonucleotides is used in signal generation, examples of the enzyme include 5'-nuclease and 3'-nuclease, particularly nucleic acid polymerase having 5'-nuclease activity, nucleic acid polymerase having 3'-nuclease activity or FEN nuclease.

In the present invention, signals may be generated by using various materials in various fashions.

According to an embodiment, at least one of the two signal-generating means is a signal-generating means to generate a signal in a dependent manner on the formation of a duplex.

According to an embodiment, the signal-generating means for each of the target nucleic acid sequences are signal-generating means to generate a signal in a dependent manner on the formation of a duplex.

According to an embodiment, the duplex includes a double stranded target nucleic acid sequence.

The expression used herein "generate a signal in a dependent manner on the formation of a duplex" in conjunction with signal-generating means refers to that signal to be detected is provided being dependent on association or dissociation of two nucleic acid molecules. The expression includes that a signal is provided by a duplex (e.g. a detection oligonucleotide with a label and a nucleic acid sequence) formed being dependent on the presence of a target nucleic acid sequence. In addition, the expression includes that a signal is provided by inhibition of hybridization of a duplex (e.g. a detection oligonucleotide with a label and a nucleic acid sequence) wherein the inhibition is caused by the formation of another duplex.

Particularly, the signal is generated by the formation of a duplex between a target nucleic acid sequence and a detection oligonucleotide specifically hybridized with the target nucleic acid sequence.

The term used herein "detection oligonucleotide" is an oligonucleotide which is involved in generation of signal to be detected. According to an embodiment of the present invention, the detection oligonucleotide includes an oligonucleotide which is involved in an actual signal generation. For example, the hybridization or non-hybridization of a detection oligonucleotide to another oligonucleotide (e.g. a target nucleic acid sequence or an oligonucleotide comprising a nucleotide sequence complementary to the detection oligonucleotide) determines the signal generation.

According to an embodiment of the present invention, the detection oligonucleotide comprises at least one label.

The signal by the formation of a duplex between a target nucleic acid sequence and the detection oligonucleotide may be generated by various methods, including Scorpion method (Whitcombe et al, Nature Biotechnology 17:804-807 (1999)), Sunrise (or Amplifluor) method (Nazarenko et al, Nucleic Acids Research, 25(12):2516-2521 (1997), and U.S. Pat. No. 6,117,635), Lux method (U.S. Pat. No. 7,537,886), Plexor method (Sherrill C B, et al., Journal of the American Chemical Society, 126:4550-45569 (2004)), Molecular Beacon method (Tyagi et al, Nature Biotechnology v.14 Mar. 1996), HyBeacon method (French D J et al., Mol. Cell Probes, 15(6):363-374(2001)), adjacent hybridization probe method (Bernard, P. S. et al., Anal. Biochem., 273:221(1999)) and LNA method (U.S. Pat. No. 6,977,295).

Particularly, the signal is generated by a duplex formed in a dependent manner on cleavage of a mediation oligonucleotide specifically hybridized with the target nucleic acid sequence.

The term used herein "mediation oligonucleotide" is an oligonucleotide which mediates production of a duplex not containing a target nucleic acid sequence.

According to an embodiment of the present invention, the cleavage of the mediation oligonucleotide per se does not generate signal and a fragment formed by the cleavage is involved in successive reactions for signal generation following hybridization and cleavage of the mediation oligonucleotide.

According to an embodiment, the hybridization or cleavage of the mediation oligonucleotide per se does not generate signal.

According to an embodiment of the present invention, the mediation oligonucleotide includes an oligonucleotide which is hybridized with a target nucleic acid sequence and cleaved to release a fragment, leading to mediate the production of a duplex. Particularly, the fragment mediates a production of a duplex by an extension of the fragment on a capture oligonucleotide.

According to an embodiment of the present invention, the mediation oligonucleotide comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence.

According to an embodiment of the present invention, the cleavage of a mediation oligonucleotide release a fragment and the fragment is specifically hybridized with a capture oligonucleotide and extended on the capture oligonucleotide.

According to an embodiment of the present invention, a mediation oligonucleotide hybridized with target nucleic acid sequences is cleaved to release a fragment and the fragment is specifically hybridized with a capture oligonucleotide and the fragment is extended to form an extended strand, resulting in formation of a extended duplex between the extended stand and the capture oligonucleotide providing a signal indicating the presence of the target nucleic acid sequence.

According to an embodiment of the present invention, where a third oligonucleotide comprising a hybridizing nucleotide sequence complementary to the extended strand is used, the hybridization of the third oligonucleotide and the extended strand forms other type of a duplex providing a signal indicating the presence of the target nucleic acid sequence.

According to an embodiment of the present invention, where a third oligonucleotide comprising a hybridizing nucleotide sequence complementary to the capture oligonucleotide is used, the formation of a duplex between the third oligonucleotide and the capture oligonucleotide is inhibited by the formation of the duplex between the extended strand and the capturing oligonucleotide, leading to provide a signal indicating the presence of the target nucleic acid sequence.

According to an embodiment of the present invention, the fragment, the extended strand, the capture oligonucleotide, the third oligonucleotide or combination of them can work as the detection oligonucleotide.

The signal by the duplex formed in a dependent manner on cleavage of the mediation oligonucleotide may be generated by various methods, including PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312).

With referring to terms disclosed in the above references, the corresponding examples of the oligonucleotides are as follows: a mediation oligonucleotide is corresponding to a PTO (Probing and Tagging Oligonucleotide), a capture oligonucleotide to a CTO (Capturing and Templating Oligonucleotide), and a third oligonucleotide to SO (Signaling Oligonucleotide) or HO (Hybridization Oligonucleotide), respectively. SO, HO, CTO, extended strand or their combination can take a role as a detection oligonucleotide.

The signal by the duplex formed in a dependent manner on cleavage of the mediation oligonucleotide includes the signal provided by inhibition of the formation of other duplex by the duplex formed in a dependent manner on cleavage of the mediation oligonucleotide (e.g. PCE-NH).

For example, where the signal by the duplex formed in a dependent manner on cleavage of the mediation oligonucleotide is generated by PTOCE method, the signal-generating means comprises an upstream oligonucleotide and a PTO (Probing and Tagging Oligonucleotide) comprising a hybridizing nucleotide sequence complementary to the target nucleic acid sequence, a CTO (Capturing and Templating Oligonucleotide), suitable label and a template-dependent nucleic acid polymerase having 5' nuclease activity. The PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence. The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The particular example of the signal generation by PTOCE method comprises the steps of:

(a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; and (d) performing an extension reaction using the resultant of the step (c) and a template-dependent nucleic acid polymerase; wherein the fragment hybridized with the capturing portion of the CTO is extended and an extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO; wherein the extended duplex provides a target signal by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label; and (e) detecting the extended duplex by measuring the target signal at a predetermined temperature that the extended duplex maintains its double-stranded form, whereby the presence of the extended duplex indicates the presence of the target nucleic acid sequence. In this case, the method further comprises repeating all or some of the steps (a)-(e) with denaturation between repeating cycles.

In the phrase "denaturation between repeating cycles", the term "denaturation" means to separate a double-stranded nucleic acid molecule to a single-stranded nucleic acid molecule.

In the step (a) of PTOCE method, a primer set for amplification of the target nucleic acid sequence may be used instead of the upstream oligonucleotide. In this case, the method further comprises repeating all or some of the steps (a)-(e) with denaturation between repeating cycles.

The PTOCE method can be classified as a process in which the PTO fragment hybridized with the CTO is extended to form an extended strand and the extended strand is then detected. The PTOCE method is characterized that the formation of the extended strand is detected by using the duplex between the extended strand and the CTO.

There is another approach to detect the formation of the extended strand. For example, the formation of the extended strand may be detected by using an oligonucleotide specifically hybridized with the extended strand (e.g., PCE-SH method). In this method, the signal may be provided from (i) a label linked to the oligonucleotide specifically hybridized with the extended strand, (ii) a label linked to the oligonucleotide specifically hybridized with the extended strand and a label linked to the PTO fragment, (iii) a label linked to the oligonucleotide specifically hybridized with the extended strand and a label incorporated into the extended strand during the extension reaction, or (iv) a label linked to the oligonucleotide specifically hybridized with the extended strand and an intercalating dye. Alternatively, the signal may be provided from (i) a label linked to the extended strand or (ii) an intercalating dye.

Alternatively, the detection of the formation of the extended strand is performed by another method in which inhibition of the hybridization between the CTO and an oligonucleotide being specifically hybridizable with the CTO is detected (e.g. PCE-NH method). Such inhibition is considered to be indicative of the presence of a target nucleic acid sequence. The signal may be provided from (i) a label linked to the oligonucleotide being hybridizable with the CTO, (ii) a label linked to the CTO, (iii) a label linked to the oligonucleotide being hybridizable with the CTO and a label linked to the CTO, or (iv) an intercalating label.

According to an embodiment, the oligonucleotide being specifically hybridizable with the CTO has an overlapping sequence with the PTO fragment.

According to an embodiment, the detection oligonucleotide includes the oligonucleotide being specifically hybridizable with the extended strand (e.g., PCE-SH method) and oligonucleotide being specifically hybridizable with the CTO (e.g. PCE-NH method). According to an embodiment, the detection oligonucleotide includes the extended strand produced during a reaction or CTO.

The PTOCE-based methods commonly involve the formation of the extended strand depending on the presence of a target nucleic acid sequence. The term "PTOCE-based method" is used herein to intend to encompass various methods for providing signals comprising the formation of an extended strand through cleavage and extension of PTO.

The example of signal generation by the PTOCE-based methods comprises the steps of: (a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; (d) performing an extension reaction using the resultant of the step (c) and a template-dependent nucleic acid polymerase; wherein the fragment hybridized with the capturing portion of the CTO is extended to form an extended strand; and (e) detecting the formation of the extended strand by detecting signal generated dependent on the presence of the extended strand. In the step (a), a primer set for amplification of the target nucleic acid sequence may be used instead of the upstream oligonucleotide. In this case, the method further comprises repeating all or some of the steps (a)-(e) with denaturation between repeating cycles.

According to an embodiment, the signal generated by the formation of a duplex includes signals induced by hybridization of the duplex (e.g., hybridization of the duplex per se, or hybridization of a third oligonucleotide) or by inhibition of hybridization of a third oligonucleotide due to the formation of a duplex.

According to an embodiment, the signal-generating means for at least one of the target nucleic acid sequences is a signal-generating means by formation of a duplex in a dependent manner on cleavage of a mediation oligonucleotide specifically hybridized with the target nucleic acid sequence.

According to an embodiment, the signal-generating means for each of the target nucleic acid sequences are a signal-generating means by formation of a duplex in a dependent manner on cleavage of a mediation oligonucleotide specifically hybridized with the target nucleic acid sequence.

According to an embodiment, at least one of the two signal-generating means is a signal-generating means to generate a signal in a dependent manner on cleavage of a detection oligonucleotide.

According to an embodiment, the signal-generating means for each of the target nucleic acid sequences are signal-generating means to generate a signal in a dependent manner on cleavage of a detection oligonucleotide.

Particularly, the signal is generated by hybridization of the detection oligonucleotide with a target nucleic acid sequence and then cleavage of the detection oligonucleotide.

The signal by hybridization of the detection oligonucleotide with a target nucleic acid sequence and then cleavage of the detection oligonucleotide may be generated by various methods, including TaqMan probe method (U.S. Pat. Nos. 5,210,015 and 5,538,848).

Where the signal is generated by TaqMan probe method, the signal-generating means includes a primer set for amplification of a target nucleic acid sequence, TaqMan probe having a suitable label (e.g., interactive dual label) and nucleic acid polymerase having 5'-nuclease activity. The TaqMan probe hybridized with a target nucleic acid sequence is cleaved during target amplification and generates signal indicating the presence of the target nucleic acid sequence.

The particular example generating signal by TaqMan probe method comprises the step of: (a) hybridizing the primer set and TaqMan probe having a suitable label (e.g., interactive dual label) with the target nucleic acid sequence; (b) amplifying the target nucleic acid sequence by using the resultant of the step (a) and nucleic acid polymerase having 5'-nuclease activity, wherein the TaqMan probe is cleaved to release the label; and (c) detecting a signal generation from the released label.

Particularly, the signal is generated by cleavage of the detection oligonucleotide in a dependent manner on cleavage of a mediation oligonucleotide specifically hybridized with the target nucleic acid sequence.

According to an embodiment, the signal-generating means for at least one of the target nucleic acid sequences is a signal-generating means to generate a signal by cleavage of the detection oligonucleotide in a dependent manner on cleavage of a mediation oligonucleotide specifically hybridized with the target nucleic acid sequence.

According to an embodiment, the signal-generating means for each of the target nucleic acid sequences are signal-generating means to generate to generate a signal by cleavage of the detection oligonucleotide in a dependent manner on cleavage of a mediation oligonucleotide specifically hybridized with the target nucleic acid sequence.

According to an embodiment of the present invention, where a mediation oligonucleotide hybridized with target nucleic acid sequences is cleaved to release a fragment, the fragment is specifically hybridized with a detection oligonucleotide and the fragment induces the cleavage of the detection oligonucleotide.

According to an embodiment of the present invention, where a mediation oligonucleotide hybridized with target nucleic acid sequences is cleaved to release a fragment, the fragment is extended to cleave a detection oligonucleotide comprising a hybridizing nucleotide sequence complementary to the capture oligonucleotide.

The signal by cleavage of the detection oligonucleotide in a dependent manner on cleavage of the mediation oligonucleotide may be generated by various methods, including Invader assay (U.S. Pat. No. 5,691,142), PCEC (PTO Cleavage and Extension-Dependent Cleavage) method (WO 2012/134195) and a method described in U.S. Pat. No. 7,309,573. In particular, the method described in U.S. Pat. No. 7,309,573 may be considered as one of PTOCE-based methods using signal generation by cleavage, and in the method, the formation of the extended strand may be detected by detecting cleavage of an oligonucleotide specifically hybridized with the CTO by the formation of the extended strand. Invader assay forms a fragment by cleavage of a mediation oligonucleotide and induces successive cleavage reactions with no extension of the fragment.

According to an embodiment of the present invention, where the signal is generated in a dependent manner on cleavage of a detection oligonucleotide, the cleavage of the detection oligonucleotide induces signal changes or releases a labeled fragment to be detected.

Where a signal-generating means generates a signal by cleavage of a detection oligonucleotide as well as by the formation of a duplex, the signal-generating means may be considered as a signal generating means providing signal by cleavage, so long as it is used to generate signal by cleavage.

Where the signal is generated by cleavage of the detection oligonucleotide, a released label by the cleavage may be detected at any temperatures.

According to the embodiment of this invention, the signal-generating means for the target nucleic acid sequences are combination of a signal-generating means by cleavage of a detection oligonucleotide, and a signal-generating means by the formation of a duplex.

According to an embodiment, the detection oligonucleotide comprises at least one label.

According to an embodiment of the present invention, the detection oligonucleotide may be composed of at least one oligonucleotide. According to an embodiment of the present invention, where the detection oligonucleotide is composed of a plurality of oligonucleotides, it may have a label in various manners. For instance, one oligonucleotide among a plurality of oligonucleotides may have at least one label, a plurality of oligonucleotides all may have at least one label, or one portion of oligonucleotides may have at least one label and the other portion may not have a label.

The signals generated by the two signal-generating means are not differentiated by a single type of detector. The term "signals not differentiated by a single type of detector" means that signals are not differentiated from each other by a single type of detector due to their identical or substantially identical signal properties (e.g., optical properties, emission wavelength and electrical signal). For example, where the same label (e.g., FAM) is used for two target nucleic acid sequences and a single type of detector for detection of emission wavelength from FAM is used, signals are not differentially detected.

The term used herein "a single type of signal" means signals providing identical or substantially identical signal properties (e.g., optical properties, emission wavelength and electrical signal). For example, FAM and CAL Fluor 610 provide different types of signals.

The term used herein "a single type of detector" means a detection means for a singly type of signal. In a detector comprising several channels (e.g., photodiodes) for several different types of signals, each channel (e.g., a photodiode) corresponds to "a single type of detector".

According to an embodiment of this invention, the two signal-generating means comprise an identical label and signals from the label are not differentiated by the single type of detector.

The label useful in the present invention includes various labels known in the art. For example, the label useful in the present invention includes a single label, an interactive dual label, an intercalating dye and an incorporating label.

The single label includes, for example, a fluorescent label, a luminescent label, a chemiluminescent label, an electrochemical label and a metal label. According to an embodiment, the single label provides a different signal (e.g., different signal intensities) depending on its presence on a double strand or single strand. According to an embodiment, the single label is a fluorescent label. The preferable types and binding sites of single fluorescent labels used in this invention are disclosed U.S. Pat. Nos. 7,537,886 and 7,348,141, the teachings of which are incorporated herein by reference in their entity. For example, the single fluorescent label includes JOE, FAM, TAMRA, ROX and fluorescein-based label. The single label may be linked to oligonucleotides by various methods. For instance, the label is linked to probes through a spacer containing carbon atoms (e.g., 3-carbon spacer, 6-carbon spacer or 12-carbon spacer).

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention.

In the signaling system comprising the reporter and quencher molecules, the reporter encompasses a donor of FRET and the quencher encompasses the other partner (acceptor) of FRET. For example, a fluorescein dye is used as the reporter and a rhodamine dye as the quencher.

The interactive dual label may be linked to one strand of a duplex. Where the strand containing the interactive dual label leaves in a single stranded state, it forms a hairpin or random coil structure to induce quenching between the interactive dual label. Where the strand forms a duplex, the quenching is relieved. Alternatively, where the interactive dual label is linked to nucleotides adjacently positioned on the strand, the quenching between the interactive dual label occurs. Where the strand forms a duplex and then is cleaved, the quenching becomes relieved.

Each of the interactive dual label may be linked to each of two strands of the duplex. The formation of the duplex induces quenching and denaturation of the duplex induces unquenching. Alternatively, where one of the two stands is cleaved, the unquenching may be induced.

Exemplified intercalating dyes useful in this invention include SYBR™ Green I, PO-PRO™-1, BO-PRO™-1, SYTO™43, SYTO™44, SYTO™45, SYTOX™ Blue, POPO™-1, POPO™-3, BOBO™-1, BOBO™-3, LO-PRO™-1, JO-PRO™-1, YO-PRO™1, TO-PRO™1, SYTO™11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

The incorporating label may be used in a process to generate signals by incorporating a label during primer extension (e.g., Plexor method, Sherrill C B, et al., Journal of the American Chemical Society, 126:4550-45569(2004)). The incorporating label may be also used in a signal generation by a duplex formed in a dependent manner on cleavage of a mediation oligonucleotide hybridized with the target nucleic acid sequence.

The incorporating label may be generally linked to nucleotides. The nucleotide having a non-natural base may be also used.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432, 272, 5,965,364, 6,001,983, and 6,037,120. The base pairing between non-natural bases involves two or three hydrogen bonds as natural bases. The base pairing between non-natural bases is also formed in a specific manner. Specific examples of non-natural bases include the following bases in base pair combinations: iso-C/iso-G, iso-dC/iso-dG, K/X, H/J, and MN (see U.S. Pat. No. 7,422,850).

Where the signal is generated by the PTOCE method, a nucleotide incorporated during the extension reaction may have a first non-natural base and the CTO may have a nucleotide having a second non-natural base with a specific binding affinity to the first non-natural base.

The term used herein "target nucleic acid", "target nucleic acid sequence" or "target sequence" refers to a nucleic acid sequence of interest for detection or quantification. The target nucleic acid sequence comprises a sequence in a single strand as well as in a double strand. The target nucleic acid sequence comprises a sequence initially present in a nucleic acid sample as well as a sequence newly generated in reactions.

The target nucleic acid sequence may include any DNA (gDNA and cDNA), RNA molecules their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA, random primers or target-specific primers may be used.

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature. The target nucleic acid sequence may include known or unknown sequences.

The term used herein "sample" refers to any cell, tissue, or fluid from a biological source, or any other medium that can advantageously be evaluated according to this invention, including virus, bacteria, tissue, cell, blood, serum, plasma, lymph, milk, urine, faeces, ocular fluid, saliva, semen, brain extracts, spinal cord fluid (SCF), appendix, spleen and tonsillar tissue extracts, amniotic fluid, ascitic fluid and non-biological samples (e.g., food and water). In addition, the sample includes natural-occurring nucleic acid molecules isolated from biological sources and synthetic nucleic acid molecules.

Signals include various signal characteristics from the signal detection, e.g., signal intensity [e.g., RFU (relative fluorescence unit) value or in the case of performing amplification, RFU values at a certain cycle, at selected cycles or at end-point], signal change shape (or pattern) or $C_t$ value, or values obtained by mathematically processing the characteristics.

According to an embodiment, the term "signal" with conjunction with reference value or sample analysis includes not only signals per se obtained at detection temperatures but also a modified signal provided by mathematically processing the signals.

According to an embodiment of this invention, when an amplification curve is obtained by real-time PCR, various signal values (or characteristics) from the amplification curve may be selected used for differentiation of signal values (or characteristics) at each detection temperature and detection of the target nucleic acid sequence (intensity, $C_t$ value or amplification curve data).

According to an embodiment of this invention, the step (a) is performed in a signal amplification process concomitantly with a nucleic acid amplification. According to an embodiment of this invention, wherein the step (a) is performed in a signal amplification process without a nucleic acid amplification.

In the present invention, the signal generated by signal-generating means may be amplified simultaneously with target amplification. Alternatively, the signal may be amplified with no target amplification.

According to an embodiment of this invention, the signal generation is performed in a process involving signal amplification together with target amplification.

According to an embodiment of this invention, the target amplification is performed in accordance with PCR (polymerase chain reaction). PCR is widely employed for target amplification in the art, including cycles of denaturation of a target sequence, annealing (hybridization) between the target sequence and primers and primer extension (Mullis et al. U.S. Pat. Nos. 4,683,195, 4,683,202 and 4,800,159; Saiki et al., (1985) Science 230, 1350-1354). The signal may be amplified by applying the signal generation methods described above (e.g., TaqMan method and PTOCE-based methods) to the PCR process. According to an embodiment, the present invention provides signals by real-time PCR method. According to an embodiment, the amplification of the target nucleic acid sequence is performed by PCR (polymerase chain reaction), LCR (ligase chain reaction, see Wiedmann M, et al., "Ligase chain reaction (LCR)—overview and applications." PCR Methods and Applications 1994 February; 3(4):551-64), GLCR (gap filling LCR, see WO 90/01069, EP 439182 and WO 93/00447), Q-beta (Q-beta replicase amplification, see Cahill P, et al., Clin Chem., 37(9):1482-5(1991), U.S. Pat. No. 5,556,751), SDA (strand displacement amplification, see G T Walker et al., Nucleic Acids Res. 20(7):16911696(1992), EP 497272), NASBA (nucleic acid sequence-based amplification, see Compton, J. Nature 350(6313):912(1991)), TMA (Transcription-Mediated Amplification, see Hofmann W P et al., J Clin Virol. 32(4):289-93(2005); U.S. Pat. No. 5,888,779).) or RCA (Rolling Circle Amplification, see Hutchison C. A. et al., Proc. Natl Acad. Sci. USA. 102:1733217336(2005)).

The amplification methods described above may amplify target sequences through repeating a series of reactions with or without changing temperatures. The unit of amplification comprising the repetition of a series of reactions is expressed as a "cycle". The unit of cycles may be expressed as the number of the repetition or time being dependent on amplification methods.

For example, the detection of signals may be performed at each cycle of amplification, selected several cycles or end-point of reactions. According to an embodiment, where signals are detected at at least two cycles, the detection of signal in an individual cycle may be performed at all detection temperatures or some selected detection temperatures. According to an embodiment of this invention, the detection is performed at the relatively high detection temperature in odd numbered cycles and at the relatively high detection temperature in even numbered cycles.

According to an embodiment of this invention, the incubation is preformed in the conditions allowing target amplification well as signal generation by the signal-generation means.

The amplification of the target nucleic acid sequence is accomplished by target amplification means including a primer set for amplification and nucleic acid polymerase.

According to an embodiment of the present invention, a nucleic acid polymerase having a nuclease activity (e.g. 5' nuclease activity or 3' nuclease activity) may be used. According to an embodiment of the present invention, a nucleic acid polymerase having a no nuclease activity may be used.

The nucleic acid polymerase useful in the present invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosipho africanus*, *Pyrococcus woesei*, *Pyrococcus horikoshii*, *Pyrococcus abyssi*, *Pyrodictium occultum*, *Aquifex pyrophilus* and *Aquifex aeolieus*. Particularly, the thermostable DNA polymerase is Taq polymerase.

According to an embodiment of the present invention, the amplification of the target nucleic acid sequence is accomplished by an asymmetric PCR. The ratio of primers may be selected in consideration of cleavage or hybridization of downstream oligonucleotides.

According to an embodiment of this invention, the step (a) is performed in a signal amplification process without a nucleic acid amplification.

Where the signal is generated by methods including cleavage of an oligonucleotide, the signal may be amplified with no target amplification. For example, the step (a) may be performed with amplification of signals but with no amplification of target sequences in accordance with CPT method (Duck P, et al., Biotechniques, 9:142-148 (1990)), Invader assay (U.S. Pat. Nos. 6,358,691 and 6,194,149), PTOCE-based methods (e.g., PCE-SH method, PCE-NH method and PCEC method) or CER method (WO 2011/037306).

The signal amplification methods described above may amplify signals through repeating a series of reactions with or without changing temperatures. The unit of signal amplification comprising the repetition of a series of reactions is expressed as a "cycle". The unit of cycles may be expressed as the number of the repetition or time being dependent on amplification methods.

For example, the generation and detection of signals may be performed at each cycle of amplification, selected several cycles or end-point of reactions.

During or after the incubation (reaction) of the sample with two signal-generating means to provide signals, the signals are detected by using a detector such as a single type of detector.

The present invention may be performed by using any type of signal-generating means in view of detection temperatures for detection of a plurality of target nucleic acid sequence. The signal-generating means may be designed to provide signals at both of the two detection temperatures or at only one of the two detection temperatures in the presence of a target nucleic acid sequence. Where the signal-generating means is designed to provide signals at only one of the two detection temperatures, it is advantageous that it provide signals only at lower detection temperature.

According to an embodiment, each of two target nucleic acid sequence is detected by a signal-generating means capable of generating signals at all detection temperatures.

According to an embodiment, $1^{st}$ target nucleic acid sequence among two target nucleic acid sequences is detected by a signal-generating means capable of generating signals at one detection temperatures and a $2^{nd}$ target nucleic acid sequence of two target nucleic acid sequences is detected by a signal-generating means capable of generating signals at two detection temperatures.

According to an embodiment, the detection temperatures are predetermined in considering a temperature range to allow signal generation by the signal-generating means.

The present invention uses that there is a certain temperature range to allow signal generation in a dependent manner on signal-generating means.

For example, when a signal-generating means generates a signal upon hybridization (or association) between two nucleic acid molecules and do not generate a signal upon non-hybridization (or dissociation) between them, a signal is generated at temperatures allowing hybridization between two nucleic acid molecules, however, no signal is generated at temperatures failing to hybridize between two nucleic acid molecules. As such, there is a certain temperature range to allow signal generation (i.e., signal detection) and other temperature range not to allow signal generation. The temperature ranges are affected by the $T_m$ value of the hybrid of the two nucleic acid molecules employed in the signal-generation means.

Where the signal generation method using a released fragment with a label after cleavage is employed, the signal may be theoretically detected at any temperature (e.g., 30-99° C.).

A detection temperature is selected from the temperature range to allow signal generation by the signal generation mean.

According to an embodiment, the signal-generating means for detecting a target nucleic acid sequence may be signal-generating means to provide different signals (e.g. signal intensity) or different signal change pattern (e.g. change extent of signal intensities) from each other at the two detection temperatures.

According to an embodiment, when the signal-generating means to generate signals in a dependent manner on cleavage of a detection oligonucleotide (e.g. TaqMan probe method) is employed, signals from the signal-generating means may be different depending on detection temperatures in the sense that signal generation by hybridization of detection oligonucleotides with target nucleic acid sequences and/or signal generation from dyes may be affected by temperatures. For instance, a probe labeled with a fluorescent reporter molecule and/or a quencher molecule may generate different signals depending on detection temperatures in which the probe may generate higher signals at the relatively low detection temperature than those at the relatively high detection temperature.

According to an embodiment, signal-generating means for the two target nucleic acid sequences are firstly constructed and then detection temperatures for the two target nucleic acid sequences are allocated, followed by performing the step (a).

According to an embodiment of this invention, when the signal-generating means generates a signal in a dependent manner on the formation of a duplex, the detection temperature is selected based on a $T_m$ value of the duplex.

According to an embodiment of this invention, when the signal-generating means generates a signal in a dependent manner on the formation of a duplex, the detection temperature is controllable by adjusting a $T_m$ value of the duplex.

For example, where the signal is generated by a detection oligonucleotide specifically hybridized with the target nucleic acid sequence (e.g., Lux probe, Molecular Beacon probe, HyBeacon probe and adjacent hybridization probe), the detection of the signal is successfully done at the predetermined temperature by adjusting the $T_m$ value of the oligonucleotide. Where Scorpion primer is used, the detection of the signal is successfully done at the predetermined temperature by adjusting the $T_m$ value of a portion to be hybridized with extended strand.

Where the signal is generated by the duplex formed dependent on the presence of the target nucleic acid sequence, the detection of the signal is successfully done at the predetermined temperature by adjusting the $T_m$ value of the duplex. For example, where the signal is generated by the PTOCE method, the detection of the signal is successfully done at the predetermined temperature by adjusting the $T_m$ value of the extended duplex formed by the extension of the PTO fragment on the CTO.

The PTOCE-based methods have advantages to readily adjust $T_m$ values of the duplex or a third hybrid whose hybridization is affected by the duplex.

According to an embodiment of this invention, when the signal-generating means generates a signal in a dependent manner on cleavage of a detection oligonucleotide, the detection temperature is arbitrarily selected. In other words, any temperature can be selected so long as the signal generated by cleavage of a detection oligonucleotide may be detected. As described above, where the signal is generated being dependent manner on cleavage of the detection oligonucleotide, the label released by the cleavage may be detected at various temperatures.

Both of signal-generating means for the two target nucleic acid sequences may be designed to provide signals at both of the two detection temperatures. According to an embodiment, TaqMan probe method, PTOCE-based methods or their combination may be selected as signal-generating means to provide signals at both of the two detection temperatures.

Alternatively, the signal-generating means for one of the two target nucleic acid sequences may be designed to provide signals at both of the two detection temperatures and the signal-generating means for the other target nucleic acid sequence may be designed to provide a signal at one detection temperature (particularly, at relatively lower detection temperature). According to an embodiment, TaqMan probe method or PTOCE-based methods may be selected to provide signals at both of the two detection temperatures and PTOCE-based methods may be selected to provide a signal at one detection temperature.

The detector used in the present invention includes any means capable of detecting signals. For example, where fluorescent signals are used, photodiodes suitable in detection of the fluorescent signals may be employed as detectors. The detection using a single type of detector means that the detection is performed by using a detector capable of detecting a single type of signal or using each channel (i.e., photodiode) of a detector carrying several channels (i.e., photodiodes).

According to an embodiment, the generation of signals includes "signal generation or extinguishment" and "signal increase or decrease" from labels.

Step (b): Establishing Equations Comprising Variables Representing Signals of Interest Provided are the following two equations each of which comprises variables representing the signals of interest generated at each detection temperature for the two target nucleic acid sequences:

$$S_{T1D1} + S_{T2D1} = S_{D1} \quad (I)$$

$$S_{T1D2} + S_{T2D2} = S_{D2} \quad (II)$$

wherein ($S_{D1}$) is a signal detected at the first detection temperature, ($S_{D2}$) is a signal detected at the second detection temperature, ($S_{T1D1}$) is a variable representing a signal of interest generated by the first signal-generating means at the first detection temperature, ($S_{T2D1}$) is a variable representing a signal of interest generated by the second signal-generating means at the first detection temperature, ($S_{T1D2}$) is a variable representing a signal of interest generated by the first signal-generating means at the second detection temperature, ($S_{T2D2}$) is a variable representing a signal of interest generated by the second signal-generating means at the second detection temperature; and the total number of variables is four.

($S_{D1}$), the signal detected at the first detection temperature (D1) consists of ($S_{T1D1}$), the signal of interest generated by the first signal-generating means at the first detection temperature (D1) and ($S_{T2D1}$), the signal of interest generated by the second signal-generating means at the first detection temperature (D1). ($S_{D2}$), the signal detected at the second detection temperature (D2) consists of ($S_{T1D2}$), the signal of interest generated by the first signal-generating means at the second detection temperature (D2) and ($S_{T2D2}$), the signal of interest generated by the second signal-generating means at the second detection temperature (D2).

($S_{D1}$) and ($S_{D2}$) may be a measured signal by detectors, i.e., a constant value. ($S_{T1D1}$), ($S_{T2D1}$), ($S_{T1D2}$) and ($S_{T2D2}$) are unknown variables to be obtained. The present invention is drawn to methods for obtaining solutions to at least one of the variables ($S_{T1D1}$), ($S_{T2D1}$), ($S_{T1D2}$) and ($S_{T2D2}$) by using measured signals ($S_{D1}$) and ($S_{D2}$).

Step (c): Establishing Additional Equations

Afterwards, provided are two additional equations each of which comprises at least one variable selected from the group consisting of the four variables, ($S_{T1D1}$), ($S_{T2D1}$), ($S_{T1D2}$) and ($S_{T2D2}$).

Following setting up the two equations (I) and (II), two additional equations are established such that a total of the four equations are provided for obtaining solutions to at least one of the variables (particularly at least two of the variables, more particularly all of the variables) in the equations (I) and (II) by a mathematical processing.

For instance, where the two additional equations enable that the equations (I) and (II) have the same variable set (i.e., the equations (I) and (II) are converted to a simultaneous equation), the solution to at least one of the variables in the equations (I) and (II) can be obtained by solving the simultaneous equation (particularly, linear simultaneous equation with two variables). Alternatively, the solution to at least one of the variables in the equations (I) and (II) may be obtained in a different manner from the simultaneous equation-solving approach.

According to an embodiment, the two additional equations are selected from the group consisting of the following equations:

$$f(S_{T1D1}, S_{T1D2}) = RV_{T1(D1D2)} \quad (III),$$

$$f(S_{T2D1}, S_{T2D2}) = RV_{T2(D1D2)} \quad (IV), \text{ and}$$

$$S_{T1D2} = \text{an arbitrarily selected value} \quad (V)$$

wherein, $RV_{T1(D1D2)}$ is a reference value (RV) of the first target nucleic acid sequence (T1) representing a relationship of change in signals provided by the first signal-generating means at the first detection temperature and the second detection temperature, $RV_{T2(D1D2)}$ is a reference value (RV) of the second target nucleic acid sequence (T2) representing a relationship of change in signals provided by the second signal-generating means at the first detection temperature and the second detection temperature; $f(S_{T1D1}, S_{T1D2})$ represents a function of $S_{T1D1}$ and $S_{T1D2}$; $f(S_{T2D1}, S_{T2D2})$ represents a function of $S_{T2D1}$ and $S_{T2D2}$;

wherein $S_{T1D2}$=an arbitrarily selected value in the equation (V) may be selected with a proviso that the first signal-generating means is prepared to generate no signal in the presence of the first target nucleic acid sequence at the second detection temperature.

According to an embodiment of the present invention, when the equation (V) is selected, the equation (III) is not selected as an additional equation.

The above-described embodiment describes two approaches to obtain the solution to at least one of the variables in the equations (I) and (II).

The first approach is to use the equations (III) and (IV) as the two additional equations.

Interestingly, the present inventors have found that when signals indicating the presence of a target nucleic acid sequence are detected in a single reaction vessel at predetermined two detection temperatures, there is a signal change in a certain relationship (pattern or rule). For example, a signal change between a signal detected at the relatively high detection temperature and a signal detected at the relatively low detection temperature for a target nucleic acid sequence shows a certain relationship (pattern or rule). For example, the intensities of the signals may be identical or substantially identical to each other or the intensities of the signals may be different from each other but in a certain range at the two detection temperatures.

The present invention is to adopt such findings to obtaining reference values and differentiating signals of interest for target nucleic acid sequences. Because signals for a target nucleic acid sequence are detected with differing only detection temperatures (e.g. no change of amount of the target or no variation of buffer conditions), there is a certain relationship (pattern or rule) in a signal change between the two detection temperatures. According to an embodiment, the present method is performed under conditions that permit a certain relationship (pattern or rule) in a signal change for a target nucleic acid sequence between the two detection temperatures.

"Reference value (RV)" of a target nucleic acid sequence represents a relationship of change in signals provided by a signal-generating means for detection of the target nucleic acid sequence means at two detection temperature.

According to an embodiment, where the RV value is used, a signal at one of detection temperatures may be expressed in terms of a signal at the other detection temperature.

In the equations (III) and (IV), $RV_{T1(D1D2)}$ and $RV_{T2(D1D2)}$ as a reference value are a predetermined value. According to an embodiment, the reference value may be obtained by using a standard material corresponding to a target nucleic acid sequence. For instance, the standard material corresponding to a target nucleic acid sequence is incubated with a corresponding signal-generating means and then signals are detected at the first detection temperature and the second detection temperature, followed by obtaining a relationship of change in the signals at the first detection temperature and the second detection temperature. The relationship of change in signals may be expressed as difference between signals detected at the first detection temperature and the second detection temperature.

The reference value is obtained through a mathematical processing of signals provided by the signal-generating means at the first detection temperature and the second detection temperature. Such mathematical processing is a function of the signals. The function used in obtaining reference values include any function so long as it gives a relationship of change in signals provided by the signal-generating means at the first detection temperature and the second detection temperature. For instance, the function may be presented as a mathematical processing such as addition, multiplication, subtraction and division of signals.

The characteristics of the signals provided at the first detection temperature and the second detection temperature per se may be used to obtain a relationship of change in signals at the first detection temperature and the second detection temperature. Alternatively, the signals at the first detection temperature and the second detection temperature may be modified by mathematically processing the characteristics of the signals and used to obtain the relationship of change in signals at the first detection temperature and the second detection temperature.

Alternatively, the initially obtained reference value may be modified and used a reference value.

According to an embodiment, the term "signal" with conjunction with the reference value includes not only signals per se obtained at detection temperatures but also a modified signal provided by mathematically processing the signals.

As described above, because $RV_{T1(D1D2)}$ and $RV_{T2(D1D2)}$ as a reference value are a predetermined value, $RV_{T1(D1D2)}$ and $RV_{T2(D1D2)}$ may serve as a convertor for (i) converting the two variables ($S_{T1D1}$) and ($S_{T1D2}$) in the equations (I) and (II) into a variable selected from the two variables and (ii) converting the two variables ($S_{T2D1}$) and ($S_{T2D2}$) in the equations (I) and (II) into a variable selected from the two variables.

According to an embodiment, the equation (III) is used to convert the two variables ($S_{T1D1}$) and ($S_{T1D2}$) in the equations (I) and (II) into a variable selected from the two variables, and the equation (IV) is used to convert the two variables ($S_{T2D1}$) and ($S_{T2D2}$) in the equations (I) and (II) into a variable selected from the two variables.

According to an embodiment, one of the two additional equations is selected from the equation (III) and the other is selected from the equation (IV).

The reference value used in this invention may be obtained in various manners. For instance, the reference value may be given as an anticipated value. In considering a target sequence, a signal-generating means and detection temperatures, the reference value representing a relationship of change in signals at the first detection temperature and the second detection temperature may be anticipated. Alternatively, the reference value may be given as an experimental or practical value by performing experiments for obtaining the reference value.

According to an embodiment, (i) $RV_{T1(D1D2)}$ is obtained by (i-1) incubating the first target nucleic acid sequence with the first signal-generating means for detection of the first target nucleic acid sequence, (i-2) detecting signals at the first detection temperature and the second detection temperature, and (i-3) then obtaining a difference between the signals detected at the first detection temperature and the second detection temperature, and (ii) $RV_{T2(D1D2)}$ is obtained by (ii-1) incubating the second target nucleic acid sequence with the second signal-generating means for detection of the second target nucleic acid sequence, (ii-2) detecting signals at the first detection temperature and the second detection temperature, and (ii-3) then obtaining a difference between the signals detected at the first detection temperature and the second detection temperature; wherein $RV_{T1(D1D2)}$ is different from $RV_{T2(D1D2)}$.

The term "difference between signals detected at the first detection temperature and the second detection temperature" in obtaining a reference value is an embodiment of a relationship of change in signals at the first detection temperature and the second detection temperature.

According to an embodiment, the difference between the signals detected at the first detection temperature and the second detection temperature comprises a difference to be obtained by mathematically processing the signal detected at the first detection temperature and the signal detected at the second detection temperature.

According to an embodiment, where the mathematical processing is done, the characteristics of the signal should be vulnerable to the mathematical processing. In certain embodiment, the mathematical processing includes calculation (e.g., addition, multiplication, subtraction and division) using signals or obtaining other values derived from signals.

The difference between the signals at the first detection temperature and the second detection temperature may be expressed in various aspects. For example, the difference may be expressed as numerical values, the presence/absence of signal or plot with signal characteristics.

The mathematical processing of the signals for obtaining the difference may be carried out by various calculation methods and their modifications.

In particular, the mathematical processing of the signals for obtaining the difference may be carried out by calculating a ratio between signals at the first detection temperature and the second detection temperature.

For instance, the ratio of the end-point intensity of the signal detected at the second detection temperature to the end-point intensity of the signal detected at the first detection temperature may be used as reference values.

According to an embodiment of this invention, the mathematical processing of the signals to obtain the difference between the signals is a calculation of a ratio of the signal detected at the relatively low detection temperature to the signal detected at the relatively high detection temperature. According to an embodiment of this invention, the mathematical processing of the signals to obtain the difference between the signals is a calculation of a ratio of the signal detected at the relatively high detection temperature to the signal detected at the relatively low detection temperature.

According to an embodiment, a reference value may be obtained by calculating the subtraction between the signal detected at the relatively high detection temperature and the signal detected at the relatively low detection temperature.

The mathematical processing for obtaining the difference may be carried out in various fashions. The mathematical processing may be carried out by use of a machine. For example, the signals may be undergone a mathematical processing by a processor in a detector or real-time PCR device. Alternatively, the signals may be manually undergone a mathematical processing particularly according to a predetermined algorithm.

According to an embodiment of the present invention, $RV_{T1(D1D2)}$ is different from $RV_{T2(D1D2)}$. According to an embodiment of the present invention, the first signal-generating means and the second signal-generating means are designed such that $RV_{T1(D1D2)}$ is different from $RV_{T2(D1D2)}$.

Where the RV values are different from each other, a quantitative expression describing a difference extent may be varied depending on approaches for calculating the RV values.

According to an embodiment, signals for obtaining reference values may be processed by a common calculation method to provide a reference value for comparison, and then a difference extent between two reference values may be obtained by using the reference value for comparison. According to an embodiment, the common calculation method is division of two signals.

For instance, while two signals are processed by subtraction for obtaining reference values used to analyze signals according to the present method, the two signals may be processed by division for obtaining a reference value for comparison.

According to an embodiment, $RV_{T1(D1D2)}$ is at least 1.1-fold, 1.2-fold, 1.3-fold, 1.5-fold, 1.7-fold, 2-fold, 2.5-fold, 3-fold, 3.5-fold, 4-fold, 5-fold or 10-fold larger than $RV_{T2(D1D2)}$. Alternatively, $RV_{T2(D1D2)}$ is at least 1.1-fold, 1.2-fold, 1.3-fold, 1.5-fold, 1.7-fold, 2-fold, 2.5-fold, 3-fold, 3.5-fold, 4-fold, 5-fold or 10-fold larger than $RV_{T1(D1D2)}$.

According to an embodiment, where the comparison is performed to determine whether the first reference value is different from the second reference, the reference values are calculated by division of the signals. According to an embodiment, the method of calculating the reference value for determining whether the first reference value is different from the second reference may be the same or different from the method of calculating the reference value for detecting the target nucleic acid sequence.

According to an embodiment of this invention, the signal-generating means for the reference value may be the same as that for the detection of the target nucleic acid sequence.

According to an embodiment, the incubation conditions for obtaining the reference values are the same as those for analysis of the sample.

For a target nucleic acid sequence, the reference values may be obtained in various reaction conditions including the amounts of components (e.g. the target nucleic acid sequence, signal-generating means, enzymes and dNTPs), buffer pH or reaction time. According to an embodiment of this invention, the reference value may be obtained under reaction conditions sufficient to provide a saturated signal at the reaction completion. According to an embodiment of this invention, the difference between the signals obtained in obtaining the reference value has a certain range and the reference value is selected within the certain range or with referring to the certain range. According to an embodiment of this invention, the reference value may be selected with maximum or minimum value of the certain range or with referring to maximum or minimum value of the certain range. Particularly, the reference value may be modified in considering standard variation of the reference values obtained in various conditions, acceptable error ranges, specificity or sensitivity.

$f(S_{T1D1}, S_{T1D2})$ or $f(S_{T2D1}, S_{T2D2})$ in "$f(S_{T1D1}, S_{T1D2})=RV_{T1(D1D2)}$ or $f(S_{T2D1}, S_{T2D2})=RV_{T2(D1D2)}$" may be presented by a mathematical expression for calculating $RV_{T1(D1D2)}$ or $RV_{T2(D1D2)}$.

According to an embodiment, $f(S_{T1D1}, S_{T1D2})=RV_{T1(D1D2)}$ comprises $S_{T1D1}/S_{T1D2}=RV_{T1D1/D2}$ (VI) or $S_{T1D2}/S_{T1D1}=RV_{T1D2/D1}$ (VII); and $f(S_{T2D1}, S_{T2D2})=RV_{T2(D1D2)}$ comprises $S_{T2D1}/S_{T2D2}=RV_{T2D1/D2}$ (VIII) or $S_{T2D2}/S_{T2D1}=RV_{T2D2/D1}$ (IX).

Where RV is obtained by using a ratio between signals at the first detection temperature (D1) and the second detection temperature (D2), $f(S_{T1D1}, S_{T1D2})$ or $f(S_{T2D1}, S_{T2D2})$ may be presented by a mathematical expression for calculating ratio between signals. In the term "$RV_{T1(D1D2)}$", T1(D1D2) indicates that a calculated RV corresponds to the reference value for the first target nucleic acid sequence (T1) obtained by calculating a difference between signals at the first detection temperature (D1) and the second detection temperature (D2). Upon determining a method for calculation RV, the term "T1(D1D2)" may be specifically expressed in considering the calculation method.

For example, the term "$RV_{T1D1/D2}$" means a reference value for the first target nucleic acid sequence (T1) obtained by calculating a ratio of a signal detected at the first detection temperature (D1) to a signal detected at the second detection temperature (D2). Alternatively, the term "$RV_{T1D2/D1}$" means a reference value for the first target nucleic acid sequence (T1) obtained by calculating a ratio of a signal detected at the second detection temperature (D2) to a signal detected at the first detection temperature (D1).

According to an embodiment, $RV_{T1D1/D2}$ is obtained by (i-1) incubating the first target nucleic acid sequence with the first signal-generating means for detection of the first target nucleic acid sequence, (i-2) detecting signals at the first detection temperature and the second detection temperature, and (i-3) then calculating a ratio of a signal detected at the first detection temperature to a signal detected at the second detection temperature; $RV_{T1D2/D1}$ is obtained by performing the steps (i-1) and (i-2) and then calculating a ratio of the signal detected at the second detection temperature to the signal detected at the first detection temperature; $RV_{T2D1/D2}$ is obtained by (ii-1) incubating the second target nucleic acid sequence with the second signal-generating means for detection of the second target nucleic acid sequence, (ii-2) detecting signals at the first detection temperature and the second detection temperature, and then (ii-3) calculating a ratio of the signal detected at the first detection temperature to the signal detected at the second detection temperature; and $RV_{T2D2/D1}$ is obtained by performing the steps (ii-1) and (ii-2) and then calculating a ratio of the signal detected at the second detection temperature to the signal detected at the first detection temperature.

According to an embodiment, the two additional equations for obtaining $(S_{T1D1})$, $(S_{T1D2})$, $(S_{T2D1})$ and $(S_{T2D2})$ comprises one of the following equations (VI) and (VII) and one of the following equations (VIII) and (IX):

$$S_{T1D1}/S_{T1D2}=RV_{T1D1/D2} \tag{VI}$$

$$S_{T1D2}/S_{T1D1}=RV_{T1D2/D1} \tag{VII}$$

$$S_{T2D1}/S_{T2D2} = RV_{T2D1/D2} \quad \text{(VIII)}$$

$$S_{T2D2}/S_{T2D1} = RV_{T2D2/D1} \quad \text{(IX)}.$$

According to an embodiment, a plurality of equations for calculating RV for a certain target nucleic acid sequence at selected two detection temperatures may be presented (e.g. the equation (VI) and (VII) for the first target nucleic acid sequence (T1) at the first detection temperature (D1) and the second detection temperature (D2)). According to an embodiment, in such case, only one equation among a plurality of equations is selected as one of the additional equations.

The equations (III) and (IV) together with the equations (I) and (II) are used for obtaining solutions to at least one of the variables. As exemplified in Example 1 and FIGS. 1A-1D, where $f(S_{T1D1}, S_{T1D2})$ is $S_{T1D1}/S_{T1D2}$ and $f(S_{T2D1}, S_{T2D2})$ is $S_{T2D1}/S_{T2D2}$, the equation set for obtaining solutions to variables includes the following:

$$S_{T1D1} + S_{T2D1} = S_{D1}$$

$$S_{T1D2} + S_{T2D2} = S_{D2}$$

$$S_{T1D1}/S_{T1D2} = RV_{T1D1/D2}$$

$$S_{T2D1}/S_{T2D2} = RV_{T2D1/D2}$$

Because $RV_{T1D1/D2}$ and $RV_{T2D1/D2}$ are an experimentally predetermined value, the solutions to the variables, $(S_{T1D1})$, $(S_{T2D1})$, $(S_{T1D2})$ and $(S_{T2D2})$ may be obtained by the four equations.

Alternatively, a reference value may be obtained by calculating the subtraction between the signal detected at the first detection temperature and the signal detected at the second detection temperature.

2

The second approach to obtain the solution to at least one of the variables in the equations (I) and (II) is to use the equations [(III) and (V)] or [(IV) and (V)] as the two additional equations. $S_{T1D2}$=an arbitrarily selected value in the equation (V) may be selected with a proviso that the first signal-generating means is prepared to generate substantially no signal in the presence of the first target nucleic acid sequence at the second detection temperature.

Where the equation (V) is applied, an arbitrarily selected value may be used as $S_{T1D2}$. According to an embodiment, it is convenient in terms of performance of the present invention that zero (0) may be used as $S_{T1D2}$ ($S_{T1D2}$=0). Alternatively, either negative numeric constant or positive numeric constant may be used as $S_{T1D2}$ ($S_{T1D2}$=negative numeric constant or $S_{T1D2}$=positive numeric constant).

The numeric values of solutions to the variables except for $(S_{T1D2})$ may be varied depending on values of the constants used in the equation (V). However, it is noteworthy that the numeric values of the solutions to the variables have values calculated by using numeric values of the constants selected as $S_{T1D2}$. Alternatively, such approach for solving the variables may be expressed in that the numeric values of the solutions to the variables except for $(S_{T1D2})$ are results obtained by using the constants selected as a value of $S_{T1D2}$ used for signal extraction.

Therefore, a signal differentiation for each target nucleic acid sequence is enabled at each detection temperature even when any constant is applied in the equation (V), while calculated variables become different depending on the constants.

In particular, when signals are detected at a plurality of cycles for obtaining a data set, a signal differentiation at each cycle is performed and then the results of signal differentiation are plotted over all cycles, absolute signal values may be altered depending on the constants in the equation (V). However, occurrence or non-occurrence of signal change (e.g., signal change pattern) over all cycles remains unchanged such that the signal differentiation for target detection may be successfully accomplished.

According to an embodiment, the solutions to the variables calculated by using the equation (V) may be mathematically modified in a defined manner. In such modification, the solutions to the variables may be modified to have values calculated by using other constants (e.g., $S_{T1D2}$=0).

The numeric values of the constants in the equation (V) used for obtaining solutions to variables are not considerable when the presence or absence of a target nucleic acid sequence of interest is determined.

When the presence or absence of a target nucleic acid sequence of interest is determined by using solutions to variables calculated by using the equation (V) as an additional equation, (i) the solutions to the variables calculated per se or (ii) the solutions mathematically modified in a defined manner may be used. Additionally, a threshold for determining significance of the calculated solutions or their mathematical modifications may be established in considering the numeric values of the constants in equation (V), thereby finally determining the presence or absence of a target nucleic acid sequence of interest.

According to an embodiment, when the equation (V) is selected, the equation (III) is not selected but the equation (IV) is selected.

It would be understood by one of skill in the art that the descriptions for the second approach in the Specification and Claims encompass embodiments in which $S_{T1D1}$=an arbitrarily selected value, $S_{T2D1}$=an arbitrarily selected value, or $S_{T2D2}$=an arbitrarily selected value is selected. For example, $S_{T2D2}$=an arbitrarily selected value may be selected with a proviso that the second signal-generating means is prepared to generate substantially no signal in the presence of the second target nucleic acid sequence at the second detection temperature. When the equation $S_{T2D2}$=an arbitrarily selected value is selected, the equation (IV) is not selected but the equation (III) is selected. Such various embodiments may be claimed and covered by the description of an embodiment ($S_{T1D2}$=an arbitrarily selected value) with avoiding undue complexity of the Specification by unnecessary redundancy.

The term "generate no signal" includes not only "no generation of signal" but also "signal generation with no significance" such as a background signal.

In particular, when signals are detected at a plurality of cycles for obtaining a data set, the term "generate no signal" means that there is no signal change or no significant signal change between cycles.

The case in which signals are detected at a plurality of cycles for obtaining a data set may include, but not limited to, obtaining a signal amplification curve by amplification reaction such as real-time PCR.

According to an embodiment, the two additional equations for obtaining $(S_{T1D1})$, $(S_{T1D2})$, $(S_{T2D1})$ and $(S_{T2D2})$ comprises one of the following equations (VIII) and (IX) and the following equation (V):

$$S_{T2D1}/S_{T2D2} = RV_{T2D1/D2} \quad \text{(VIII)}$$

$$S_{T2D2}/S_{T2D1} = RV_{T2D2/D1} \quad \text{(IX)}$$

$$S_{T1D2} = \text{an arbitrarily selected value} \quad \text{(V)}.$$

Figure 2A:
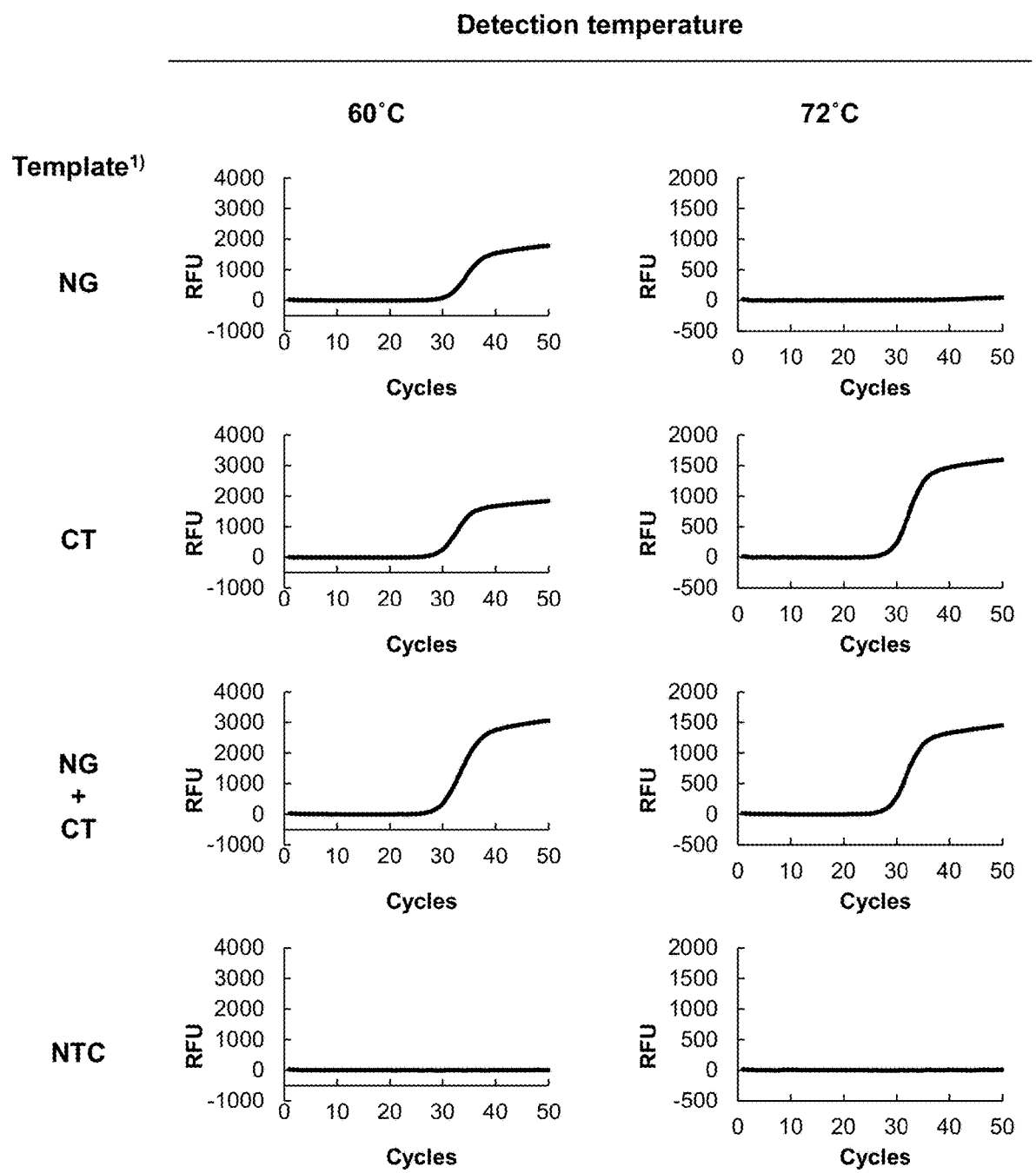
FIG. 2A represents the detection results of a first target nucleic acid sequence (genome DNA of *Neisseria gonorrhoeae*, NG), a second target nucleic acid sequence (genome DNA of *Chlamydia trachomatis*, CT) and their combination at a first detection temperature (60° C.) and a second detection temperature (72° C.). The signals for NG and CT were generated by the PTOCE method. The signal generating means for CT was designed to provide a signal of interest at 60° C. and 72° C. and those for NG was designed to provide a signal of interest at only 60° C.
Figure 2C:
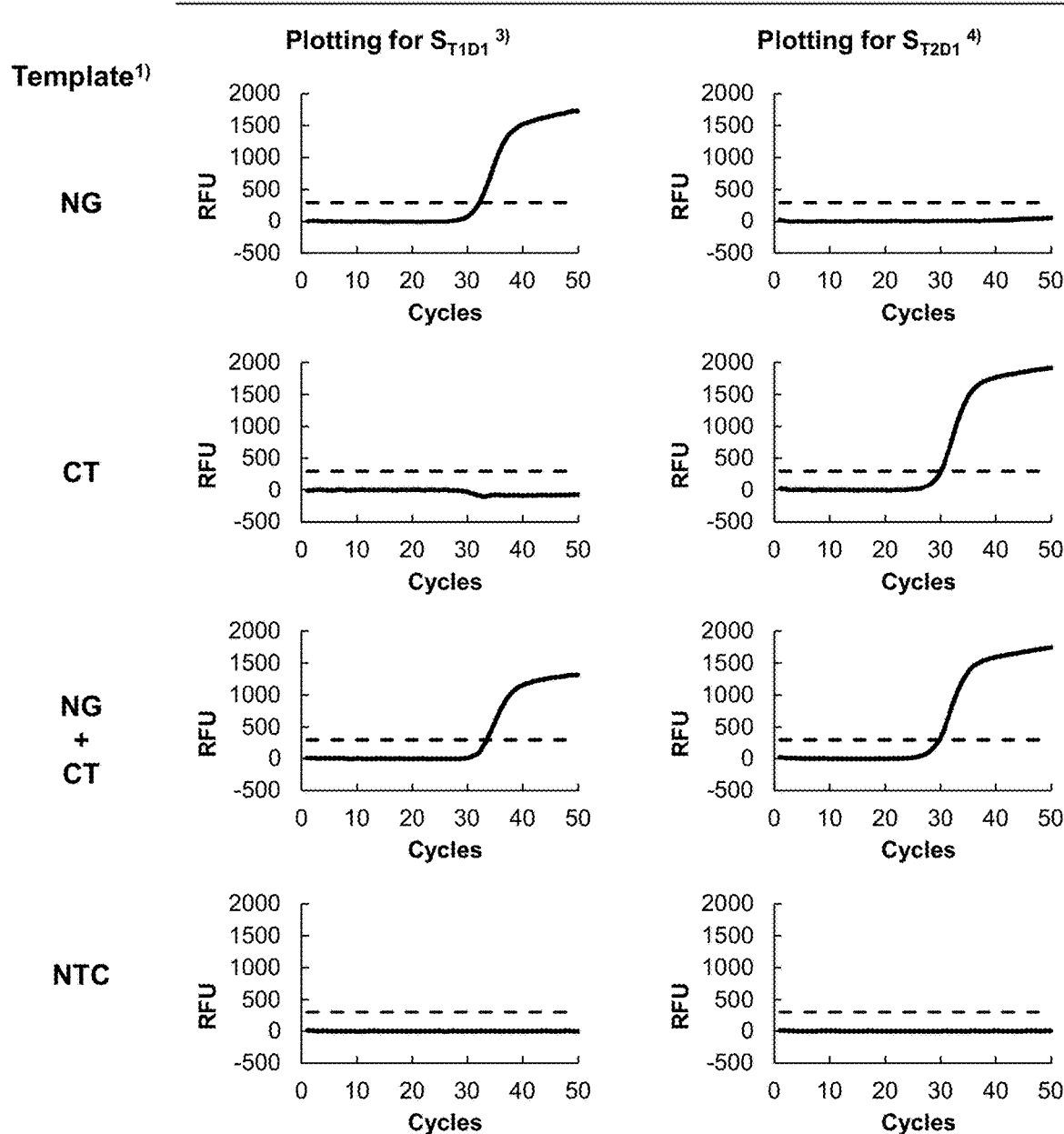
FIG. 2C represents plotting results for $S_{T1D1}$ and $S_{T2D1}$ obtained by solving the equation set 2 ($S_{T1D2}$=0). The dotted line represents a threshold which was determined with referring to the result of NG only sample and CT only sample in FIG. 2A to verify the significance of the obtained amplification curves.
Figure 2D:
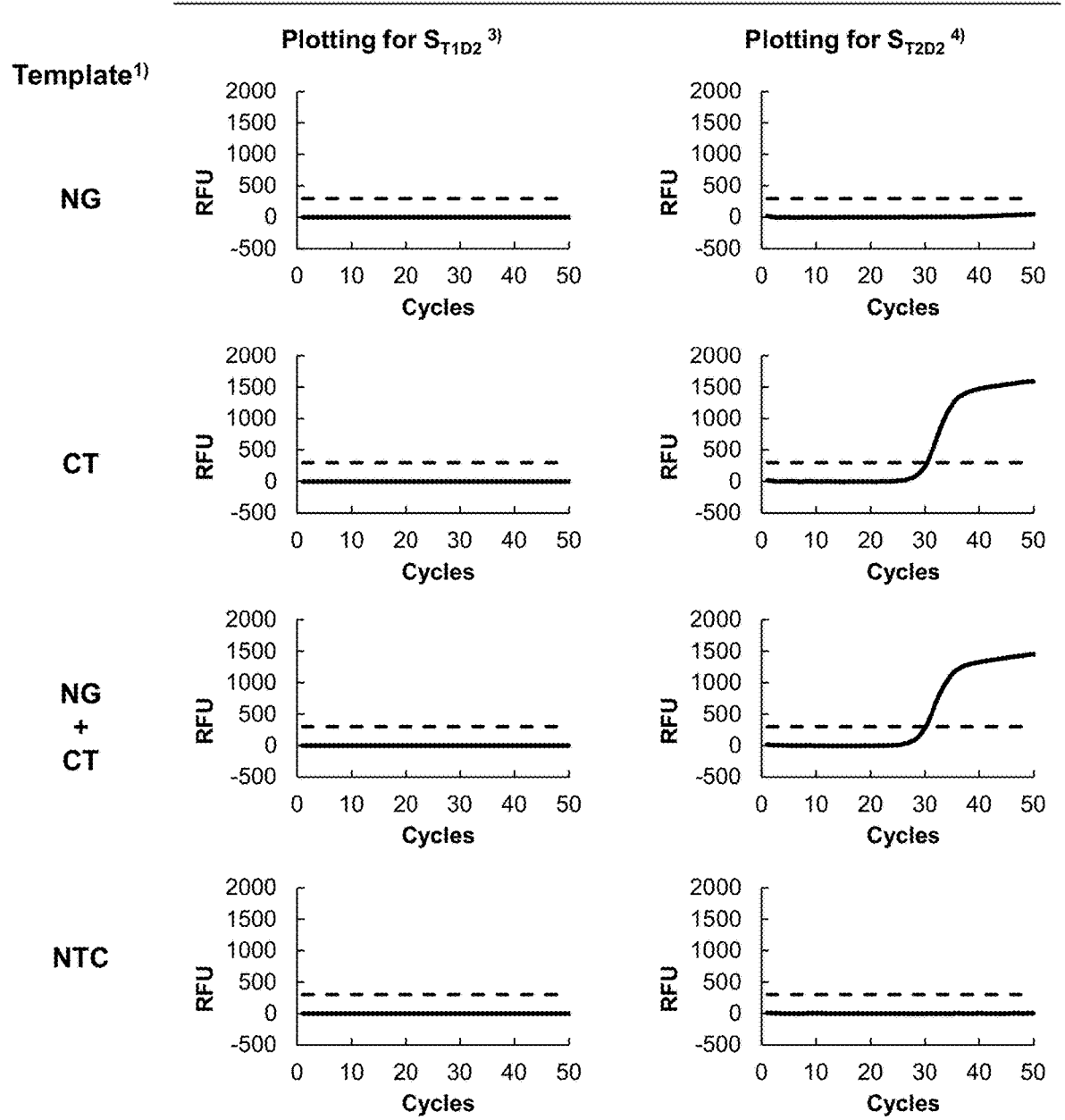
FIG. 2D represents plotting results for $S_{T1D2}$ and $S_{T2D2}$ obtained by solving the equation set 2 ($S_{T1D2}$=0). The dotted line represents a threshold.

As exemplified in Example 2 and FIGS. 2C-2D, where the first signal-generating means is prepared to generate substantially no signal in the presence of the first target nucleic acid sequence at the second detection temperature, $S_{T1D2}=0$ in the equation (V) and $f(S_{T2D1}, S_{T2D2})=RV_{T2(D1D2)}$ (IV) as the additional equation may be selected for obtaining solutions to at least one of the variables. Where $f(S_{T2D1}, S_{T2D2})$ is $S_{T2D1}/S_{T2D2}$, the equation set for obtaining solutions to variables includes the following:

$$S_{T1D1}+S_{T2D1}=S_{D1}$$

$$S_{T1D2}+S_{T2D2}=S_{D2}$$

$$S_{T1D2}=0$$

$$S_{T2D1}/S_{T2D2}=RV_{T2D1/D2}$$

Because $RV_{T2D1/D2}$ is a predetermined constant value, the solutions to the variables, $(S_{T1D1})$, $(S_{T2D1})$ and $(S_{T1D2})$ may be obtained by the four equations.

As a particular embodiment of the first approach using the equations (III) and (IV) as the two additional equations, $RV_{T1(D1D2)}$ may be selected as an arbitrarily selected value when the first signal-generating means is prepared to generate no signal in the presence of the first target nucleic acid sequence at the second detection temperature.

According to an embodiment, when the first signal-generating means is prepared to generate substantially no signal in the presence of the first target nucleic acid sequence at the second detection temperature, $RV_{T1(D1D2)}$ is an arbitrarily selected value.

As described above, where the first target nucleic acid sequence (T1) generates no signal at the second detection temperature (D2), an arbitrarily selected value may be used as $S_{T1D2}$, whereby $RV_{T1(D1D2)}$ may become an arbitrarily selected value.

Particularly, the arbitrarily selected value as $RV_{T1(D1D2)}$ may be selected such that a solution (value) of $S_{T1D2}$ is rendered to be a value or around the value (e.g., "0" or around "0" in the equations.

The term "around the value" with conjunction to "a value or around the value" means any number within a significance level being considerable as a value.

Particularly, when $f(S_{T1D1}, S_{T1D2})$ is be presented by a mathematical expression for calculating ratio between signals at the first detection temperature (D1) and the second detection temperature (D2), $RV_{T1(D1D2)}$ may be selected as an arbitrarily selected value.

Practically, even when the first signal-generating means is prepared to generate no signal in the presence of the first target nucleic acid sequence at the second detection temperature, it is usually to generate signals with very weak intensities (e.g., background signal). In particular, the arbitrarily selected value as $RV_{T1(D1D2)}$ may be the same as, less or greater than $RV_{T1(D1D2)}$ calculated with practically-obtained signal values.

It would be understood by one of skill in the art that the descriptions for the first approach in the Specification and Claims encompass embodiments in which $RV_{T1(D1D2)}$ or $RV_{T2(D1D2)}$ is an arbitrarily selected value. For example, $RV_{T2(D1D2)}$ may be an arbitrarily selected value with a proviso that the second signal-generating means is prepared to generate substantially no signal in the presence of the second target nucleic acid sequence at the second detection temperature. Such various embodiments may be claimed and covered by the description of the embodiment ($RV_{T1(D1D2)}$ as an arbitrarily selected value) with avoiding undue complexity of the Specification by unnecessary redundancy.

The equations (III) and (IV) together with the equations (I) and (II) are used for obtaining solutions to at least one of the variables. As exemplified in Example 2 and FIGS. 2G-2H, where the first signal-generating means is prepared to generate substantially no signal in the presence of the first target nucleic acid sequence at the second detection temperature, $RV_{T1(D1D2)}$ may be an arbitrarily selected value. Where $f(S_{T1D1}, S_{T1D2})$ is $S_{T1D1}/S_{T1D2}$ and $f(S_{T2D1}, S_{T2D2})$ is $S_{T2D1}/S_{T2D2}$, the equation set for obtaining solutions to variables includes the following:

$$S_{T1D1}+S_{T2D1}=S_{D1}$$

$$S_{T1D2}+S_{T2D2}=S_{D2}$$

$$S_{T1D1}/S_{T1D2}=RV_{T1D1/D2}$$

$$S_{T2D1}/S_{T2D2}=RV_{T2D1/D2}$$

Because $RV_{T1D1/D2}$ is an arbitrarily selected value, the solutions to the variables, $(S_{T1D1})$, $(S_{T2D1})$, $(S_{T1D2})$ and $(S_{T2D2})$ may be obtained by the four equations.

It is very interesting that the present method allows for quantification of a signal amount (e.g. signal intensity) generated by each of the signal-generating means. As described above, the solutions to the variables, $(S_{T1D1})$, $(S_{T2D1})$, $(S_{T1D2})$ and $(S_{T2D2})$ permit quantification of a signal amount (e.g. signal intensity) generated by each of the signal-generating means, which may be applied to quantification of the target nucleic acid sequences.

Step (d): Obtaining Solutions to Variables

Finally, the solutions to at least one of the variables are obtained by using the four equations provided in the steps (b) and (c) for differentiating at least one of the signals of interest to be assigned to at least one of the two target nucleic acid sequences.

As described above, the four equations provided in the steps (b) and (c) are used to obtain the solutions to at least one of the variables for differentiating at least one of the signals of interest to be assigned to at least one of the two target nucleic acid sequences, whereby the presence of at least one of the two target nucleic acid sequences may be determined.

Particularly, the solutions to at least two (more particularly at least three, most particularly four) of the variables are obtained by using the four equations provided in the steps (b) and (c) for differentiating at least two (more particularly at least three, most particularly four) of the signals of interest to be assigned to at least one (most particularly all) of the two target nucleic acid sequences.

According to an embodiment, the present method is used to obtain solutions (values) to the two variables and one of the two variables is selected from the variables for the first target nucleic acid sequence and the other is selected from the variables for the second target nucleic acid sequence.

According to an embodiment, depending on approaches for generating signals, a threshold value may be employed to analyze whether the obtained solutions (values) to the variables may be significant.

A negative control, sensitivity or label used may be considered for determining the threshold value. According to an embodiment of this invention, a threshold value may be determined by user or automatically.

According to an embodiment, the threshold value is determined with referring to signals detected using only the first target nucleic acid sequence or only the second target nucleic acid sequence.

According to an embodiment, where signals are generated in a real-time manner associated with target amplification by PCR, the signals at each amplification cycle or some selected cycles are mathematically processed with the reference values and the calculation results are plotted against cycles and used for differentiating the signals of interest (e.g., determination of the presence of the target nucleic acid sequence).

According to an embodiment of this invention, the two target nucleic acid sequences comprises a nucleotide variation and one of the two target nucleic acid sequences comprises one type of the nucleotide variation and the other comprises the other type of the nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and any mutant type at a particular location in a nucleic acid sequence.

According to an embodiment of this invention, the nucleotide variation detected by the present invention is a SNP (single nucleotide polymorphism).

According to an embodiment of this invention, a homozygote composed of a first SNP allele is detected by using the signal-generating means for the first target nucleic acid sequence, a homozygote composed of a second SNP allele by using the second signal-generating means for the second target nucleic acid sequence and a heterozygote composed of the first SNP allele and the second SNP allele by using the two signal-generating means.

II. Differentiation of Signals of Interest for at Least Three Target Nucleic Acid Sequences In another aspect of this invention, there is provided a method for differentiating signals of interest for each of target nucleic acid sequences in the number of N in a sample, which are not differentiable by a single type of detector, comprising:

(a) incubating the sample with signal-generating means in the number of N for detection of the target nucleic acid sequences in the number of N and detecting signals at detection temperatures in the number of N; wherein each of the target nucleic acid sequences is detected by a corresponding signal-generating means; wherein the signals of interest to be generated by the signal-generating means in the number of N are not differentiated for each target nucleic acid sequence by a single type of detector; wherein N is an integer not less than 2;

(b) providing the following equations in the number of N each of which comprises variables representing the signals of interest generated at each detection temperature for the target nucleic acid sequences;

$$S_{T1D1} + S_{T2D1} + \ldots + S_{TND1} = S_{D1} \tag{1}$$

$$S_{T1D2} + S_{T2D2} + \ldots + S_{TND2} = S_{D2} \tag{2}$$

$$\vdots$$

$$S_{T1DN} + S_{T2DN} + \ldots + S_{TNDN} = S_{DN} \tag{N}$$

wherein each of $(S_{D1})$ to $(S_{DN})$ is a signal detected at each detection temperature; each of $(S_{T1D1})$ to $(S_{TNDN})$ is a variable representing a signal of interest generated by each signal-generating means at each detection temperature; and the total number of the variables is $N^2$;

(c) providing additional equations in the number of $(N^2-N)$ each of which comprises at least one variable selected from the group consisting of the variables, $(S_{T1D1})$ to $(S_{TNDN})$; and (d) obtaining solutions to at least one of the variables by the equations in the number of $N^2$ provided in the steps (b) and (c) for differentiating at least one of the signals of interest to be assigned to at least one of the target nucleic acid sequences in the number of N.

The present method is expressed herein as a method for differentiating signals of interest for each of target nucleic acid sequences in the number of N in a sample and alternatively may be expressed as a method for detecting at least one of the target nucleic acid sequences in a sample or a method for determining the presence of at least one of the target nucleic acid sequences in a sample by assigning at least one of signals of interest to at least one of the target nucleic acid sequences.

Since the second aspect follows in principle the technological principle and features of the first aspect of this invention described above, the common descriptions between them are omitted in order to avoid undue redundancy leading to the complexity of this specification. When referring to descriptions for the first aspect in order to describe the second aspect, it should be noted that the second aspect may be, in part, different from the first aspect. Therefore, it would be understood to those skilled in the art that some descriptions for the first aspect may be directly applied to descriptions for the second aspect and other descriptions may be applied to descriptions for the second aspect by a little modification.

The present invention will be described in more detail as follows:

Step (a): Incubating Samples with Signal-Generating Means and Signal Detection

Firstly, the sample to be analyzed is incubated with signal-generating means in the number of N for detection of the target nucleic acid sequences in the number of N and then signals from the signal-generating means are detected at detection temperatures in the number of N; wherein each of the target nucleic acid sequences is detected by a corresponding signal-generating means; wherein the signals of interest to be generated by the signal-generating means in the number of N are not differentiated for each target nucleic acid sequence by a single type of detector; wherein N is an integer not less than 2.

The number of the target nucleic acid sequences (N) to be detected in the present invention is not limited, including more than 2, 3, 4, 5, 6, 7, 8, 9 and 10 target nucleic acid sequences.

For example, where the number of the target nucleic acid sequences is three, N is three and the target nucleic acid sequence may be expressed as T1, T2 and T3, respectively.

According to an embodiment, where the target nucleic acid sequences are in the number of N, the signal-generating means are used in the number of N.

Where the target nucleic acid sequences are in the number of N, the detection temperatures are used in the number of N. For example, where the number of the target nucleic acid sequences is three, N is three and the detection temperatures are used in the number of three. The detection temperatures may be expressed as D1, D2 and D3, respectively.

The present invention utilizes signal-generating means for providing signals for target nucleic acid sequences. Each of the target nucleic acid sequences is detected by a corresponding signal-generating means. For example, the $g^{th}$ target nucleic acid sequence among the target nucleic acid sequences in the number of N may be detected by the $g^{th}$ signal-generating means, where the term "g" is an integer selected from 1 to N.

According to an embodiment of this invention, the incubation is preformed under conditions allowing a signal generation by the signal-generation means.

According to an embodiment of this invention, the incubation is preformed in a single reaction vessel containing signal-generating means in the number of N.

The signal-generation means for the second aspect of the present invention may be with reference to those for the first aspect of the present invention.

In the present invention, signals may be generated by using various materials in various fashions.

According to an embodiment, at least one of the signal-generating means in the number of N is a signal-generating means to generate a signal in a dependent manner on the formation of a duplex.

According to an embodiment, the signal-generating means for each of the target nucleic acid sequences are signal-generating means to generate a signal in a dependent manner on the formation of a duplex.

Particularly, the signal is generated by the formation of a duplex between a target nucleic acid sequence and a detection oligonucleotide specifically hybridized with the target nucleic acid sequence.

Particularly, the signal is generated by a duplex formed in a dependent manner on cleavage of a mediation oligonucleotide specifically hybridized with the target nucleic acid sequence.

The signal by the duplex formed in a dependent manner on cleavage of the mediation oligonucleotide may be generated by various methods, including PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312).

According to an embodiment, at least one of the signal-generating means in the number of N is a signal-generating means to generate a signal in a dependent manner on cleavage of a detection oligonucleotide.

According to an embodiment, the signal-generating means for each of the target nucleic acid sequences are signal-generating means to generate a signal in a dependent manner on cleavage of a detection oligonucleotide.

Particularly, the signal is generated by hybridization of the detection oligonucleotide with a target nucleic acid sequence and then cleavage of the detection oligonucleotide. The signal by hybridization of the detection oligonucleotide with a target nucleic acid sequence and then cleavage of the detection oligonucleotide may be generated by various methods, including TaqMan probe method (U.S. Pat. Nos. 5,210,015 and 5,538,848).

Particularly, the signal is generated by cleavage of the detection oligonucleotide in a dependent manner on cleavage of a mediation oligonucleotide specifically hybridized with the target nucleic acid sequence. According to an embodiment of this invention, the cleavage of a mediation oligonucleotide releases a fragment and the fragment mediates a formation of a duplex or a cleavage of a detection oligonucleotide by an extension of the fragment on a capture oligonucleotide.

According to an embodiment of this invention, the signal-generating means for at least one of the target nucleic acid sequences in the number of N is a signal-generating means by cleavage of a detection oligonucleotide, and the signal-generating means for the other target nucleic acid sequences are a signal-generating means by the formation of a duplex.

According to an embodiment, each target nucleic acid sequence is detected by a signal-generating means capable of generating signals at all detection temperatures.

According to an embodiment, an $g^{th}$ target nucleic acid sequence among the target nucleic acid sequences in the number of N is detected by a signal-generating means capable of generating signals at detection temperatures in the number of at least "g". For example, an $3^{rd}$ target nucleic acid sequence among the target nucleic acid sequences is detected by a signal-generating means capable of generating signals at three or more detection temperatures.

According to an embodiment of this invention, the signal-generating means in the number of N comprise an identical label and signals from the label are not differentiated by the single type of detector.

According to an embodiment of this invention, the step (a) is performed in a signal amplification process concomitantly with a nucleic acid amplification.

In the present invention, the signal generated by signal-generating means may be amplified simultaneously with target amplification. Alternatively, the signal may be amplified with no target amplification.

According to an embodiment of this invention, the signal generation is performed in a process involving signal amplification together with target amplification.

According to an embodiment of this invention, the target amplification is performed in accordance with PCR (polymerase chain reaction).

According to an embodiment of this invention, the incubation is preformed in the conditions allowing target amplification well as signal generation by the signal-generation means.

According to an embodiment of this invention, the step (a) is performed in a signal amplification process without a nucleic acid amplification.

Where the signal is generated by methods including cleavage of an oligonucleotide, the signal may be amplified with no target amplification.

During or after the incubation (reaction) of the sample with the signal-generating means to provide signals, the signals are detected by using a detector such as a single type of detector. According to the present invention, the presence or absence of the two target nucleic acid sequences may be determined even using a single type of detector.

The present invention may be performed by using any type of signal-generating means in view of detection temperatures.

The signal-generating means may be designed to provide signals at all or a portion of the detection temperatures in the number of N.

Particularly, the signal-generating means may be designed to provide different signals upon changing detection temperatures.

According to an embodiment, the detection temperatures are predetermined in considering a temperature range to allow signal generation by the signal-generating means.

A detection temperature is selected from the temperature range to allow signal generation by the signal generation mean.

According to an embodiment, the detection temperatures in the number of N are different from each other.

According to an embodiment, the signal-generating means for detecting a target nucleic acid sequence may be signal-generating means to provide different signals (e.g. signal intensity) from each other at each of the detection temperatures in the number of N.

According to an embodiment, signal-generating means for the two target nucleic acid sequences are firstly constructed and then detection temperatures for the two target nucleic acid sequences are allocated, followed by performing the step (a).

According to an embodiment of this invention, when the signal-generating means generates a signal in a dependent manner on cleavage of a detection oligonucleotide, the detection temperature is arbitrarily selected. In other words, any temperature can be selected so long as the signal generated by cleavage of a detection oligonucleotide may be detected. As described above, where the signal is generated being dependent manner on cleavage of the detection oligonucleotide, the label released by the cleavage may be detected at various temperatures.

The detector used in the present invention includes any means capable of detecting signals. For example, where fluorescent signals are used, photodiodes suitable in detection of the fluorescent signals may be employed as detectors. The detection using a single type of detector means that the detection is performed by using a detector capable of detecting a single type of signal or using each channel (i.e., photodiode) of a detector carrying several channels (i.e., photodiodes).

Step (b): Establishing Equations Comprising Variables Representing Signals of Interest Provided are the following equations in the number of N each of which comprises variables representing the signals of interest generated at each detection temperature for the target nucleic acid sequences;

$$S_{T1D1} + S_{T2D1} + ... + S_{TND1} = S_{D1} \tag{1}$$

$$S_{T1D2} + S_{T2D2} + ... + S_{TND2} = S_{D2} \tag{2}$$

$$\vdots$$

$$S_{T1DN} + S_{T2DN} + ... + S_{TNDN} = S_{DN} \tag{N}$$

wherein each of ($S_{D1}$) to ($S_{DN}$) is a signal detected at each detection temperature; each of ($S_{T1D1}$) to ($S_{TNDN}$) is a variable representing a signal of interest generated by each signal-generating means at each detection temperature; and the total number of the variables is $N^2$.

In the above mathematical equations, " . . . " in a horizontal dot line represents a variable or variables of which number is dependent on the number of N. For instance, where N is three, there is no additional variable represented by the horizontal dot line. Where N is four, there is an additional variable in the number of (N−3) represented by the horizontal dot line. Furthermore, " . . . " in a vertical dot line represents an equation or equations of which number is dependent on the number of N. For instance, where N is three, there is no additional equation represented by the vertical dot line. Where N is four, there is an additional equation in the number of (N−3) represented by the vertical dot line.

Where N is two, the equation set is presented as follows:

$$S_{T1D1} + S_{T2D1} = S_{D1} \tag{1}$$

$$S_{T1D2} + S_{T2D2} = S_{D2} \tag{2}$$

($S_{D1}$), the signal detected at the first detection temperature (D1) consists of signals of interest in the number of N generated by the signal-generating means in the number of N for the target nucleic acid sequences in the number of N at the first detection temperature (D1). In other words, ($S_{D1}$), the signal detected at the first detection temperature consists of ($S_{T1D1}$), the signal of interest generated by the first signal-generating means for the first target nucleic acid sequence at the first detection temperature to ($S_{TND1}$), the signal of interest generated by the $N^{th}$ signal-generating means for the $N^{th}$ target nucleic acid sequence at the first detection temperature.

The equations for other detection temperatures may be interpreted as described above for the first detection temperature.

For example, ($S_{DN}$), the signal detected at the $N^{th}$ detection temperature (DN) consists of N개의 signals of interest generated by the signal-generating means in the number of N for the target nucleic acid sequences in the number of N at the $N^{th}$ detection temperature (DN). ($S_{DN}$), the signal detected at the $N^{th}$ detection temperature consists of ($S_{T1DN}$), the signal of interest generated by the first signal-generating means for the first target nucleic acid sequence at the $N^{th}$ detection temperature to ($S_{TNDN}$), the signal of interest generated by the $N^{th}$ signal-generating means for the $N^{th}$ target nucleic acid sequence at the $N^{th}$ detection temperature.

($S_{D1}$) to ($S_{DN}$) may be a measured signal by detectors, i.e., a constant value. ($S_{T1D1}$) to ($S_{TNDN}$) are unknown variables to be obtained. The present invention is drawn to methods for obtaining solutions to at least one of the variables ($S_{T1D1}$) to ($S_{TNDN}$) by using measured signals ($S_{D1}$) to ($S_{DN}$).

In a particular example, where the target nucleic acid sequences in the number of N in a sample comprises T1, T2 and T3, and the detection temperatures in the number of N comprises 60° C., 72° C. and 95° C., the following equations in the number of N each of which comprises variables representing the signals of interest generated at each detection temperature for the target nucleic acid sequences may be provided:

$$S_{T1D1} + S_{T2D1} + S_{T3D1} = S_{D1}$$

$$S_{T1D2} + S_{T2D2} + S_{T3D2} = S_{D2}$$

$$S_{T1D3} + S_{T2D3} + S_{T3D3} = S_{D3}$$

Step (c): Establishing Additional Equations

Afterwards, provided are additional equations in the number of ($N^2-N$) each of which comprises at least one variable selected from the group consisting of the variables, ($S_{T1D1}$) to ($S_{TNDN}$).

Following setting up the equations (1) to (N), additional equations in the number of ($N^2-N$) are established such that the additional equations are provided for obtaining solutions to at least one of the variables (particularly at least two of the variables, more particularly at least three of the variables, still more particularly at least four of the variables, still much more particularly at least five of the variables) in the equations (1) to (N) by a mathematical processing.

Mathematically, the equations in the number of $N^2$ provided in the steps (b) and (c) may provide solutions to at least one of the variables.

For instance, where the additional equations enable that the equations (1) to (N) have the same variable set (i.e., the equations (1) to (N) are converted to a simultaneous equation), the solution to at least one of the variables in the equations (1) to (N) can be obtained by solving the simultaneous equation (particularly, linear simultaneous equation with variables in the number of N). Alternatively, the solution to at least one of the variables in the equations (1) to (N) may be obtained in a different manner from the simultaneous equation-solving approach.

According to an embodiment, the additional equations in the number of $(N^2-N)$ are selected from the group of the following equations:

$$f(S_{TjD\alpha}, S_{TjD\beta}) = RV_{Tj(D\alpha D\beta)} \quad (X), \text{ and}$$

$$S_{TjDK} = \text{an arbitrarily selected value} \quad (XI)$$

wherein, j in Tj represents all integers starting from 1 to a $N^{th}$ integer; for each $j^{th}$ target nucleic acid, $\alpha$ and $\beta$ jointly represent a combination of two integers selected from 1 to N; wherein the number of the combination is represented by $_NC_2$; for each $j^{th}$ target nucleic acid, K is at least one of integers selected from 1 to N; $RV_{Tj(D\alpha D\beta)}$ is a reference value (RV) of the $j^{th}$ target nucleic acid sequence (Tj) representing relationship reflecting change in signals provided by the $j^{th}$ signal-generating means at the $\alpha^{th}$ detection temperature and the $\beta^{th}$ detection temperature; $f(S_{TjD\alpha}, S_{TjD\beta})$ represents a function of $S_{TjD\alpha}$ and $S_{TjD\beta}$;

wherein $S_{TjDK}$=an arbitrarily selected value in the equation (XI) may be selected with a proviso that the $j^{th}$ signal-generating means is prepared to generate no signal in the presence of the $j^{th}$ target nucleic acid sequence at the $K^{th}$ detection temperature; and wherein when the equation (XI) is selected as the additional equations, the other additional equations are selected from the equation (X) in which $\alpha$ or $\beta$ for the $j^{th}$ target nucleic acid sequence is different from K for the $j^{th}$ target nucleic acid sequence.

According to an embodiment, it is convenient in terms of performance of the present invention that zero (0) may be used as $S_{TjDK}$ ($S_{TjDK}=0$). Alternatively, either negative numeric constant or positive numeric constant may be used as $S_{TjDK}$ ($S_{TjDK}$=negative numeric constant or $S_{TjDK}$=positive numeric constant).

$S_{TjD\alpha}$ and $S_{TjD\beta}$ represents signals provided by the $j^{th}$ signal-generating means at the $\alpha^{th}$ detection temperature (D$\alpha$) and at the $\beta^{th}$ detection temperature (D$\beta$), respectively, when the $j^{th}$ target nucleic acid sequence (Tj) is present.

The equation (X) is presented for describing a plurality of equations as a single general equation.

In the mathematical equation (X), j in Tj represents all integers starting from 1 to a $N^{th}$ integer, and $\alpha$ and $\beta$ jointly represent a combination of two integers selected from 1 to N. The term "combination" in conjunction with $\alpha$ and $\beta$ is a mathematic combination meaning a way of selecting items from a collection, such that the order of selection does not matter. The combination of $\alpha$ and $\beta$ means a combination of two among the detection temperatures in the number of N. The number of the combination of $\alpha$ and $\beta$ is represented by $_NC_2$.

According to an embodiment, where the target nucleic acid sequences are in the number of N, the equation (X) permits to describe equations in the number of "$N \times [_NC_2]$".

For instance, where N is 3, j comprises 1, 2 and 3 and the combination of $\alpha$ and $\beta$ comprises (1, 2), (1, 3) and (2, 3). In this case, the equation (X) describes nine (9) equations.

For example, "$f(S_{TjD\alpha}, S_{TjD\beta})=RV_{Tj(D\alpha D\beta)}$" may comprise:

(i) in the case of j=1;

$$f(S_{T1D1}, S_{T1D2}) = RV_{T1(D1D2)},$$

$$f(S_{T1D1}, S_{T1D3}) = RV_{T1(D1D3)},$$

$$f(S_{T1D2}, S_{T1D3}) = RV_{T1(D2D3)},$$

(ii) in the case of j=2;

$$f(S_{T2D1}, S_{T2D2}) = RV_{T2(D1D2)},$$

$$f(S_{T2D1}, S_{T2D3}) = RV_{T2(D1D3)},$$

$$f(S_{T2D2}, S_{T2D3}) = RV_{T2(D2D3)},$$

(ii) in the case of j=3

$$f(S_{T3D1}, S_{T3D2}) = RV_{T3(D1D2)},$$

$$f(S_{T3D1}, S_{T3D3}) = RV_{T3(D1D3)}, \text{ and}$$

$$f(S_{T3D2}, S_{T3D3}) = RV_{T3(D2D3)}.$$

According to an embodiment, where the additional equations in the number of $(N^2-N)$ are selected from the equation (X), they may be selected such that equations in the number of (N-1) are selected from the equation group for each j.

More particularly, such (N-1) equation selection may be carried out such that the selected (N-1) equations for each j provides a simultaneous equation with variables in the number of N to obtain solutions to at least one of the variables by the equations (1) to (N).

In the particular example in which N is 3 and signals at the detection temperature D1 are analyzed, two equations (i.e. N-1=3-1=2) for each j may be selected among three presentable equations. Six (6) additional equations selected from the nine (9) equations described above are selected as follows:

$$f(S_{T1D1}, S_{T1D2}) = RV_{T1(D1D2)}$$

$$f(S_{T1D1}, S_{T1D3}) = RV_{T1(D1D3)}$$

$$f(S_{T2D1}, S_{T2D2}) = RV_{T2(D1D2)}$$

$$f(S_{T2D1}, S_{T2D3}) = RV_{T2(D1D3)}$$

$$f(S_{T3D1}, S_{T3D2}) = RV_{T3(D1D2)}$$

$$f(S_{T3D1}, S_{T3D3}) = RV_{T3(D1D3)}$$

Particularly, the additional equations in the number of $(N^2-N)$ comprise equations selected from an equation group represented by the equation (X).

According to an embodiment, a portion of the additional equations in the number of $(N^2-N)$ can be selected from the group of the following equation:

$$S_{TjDK} = \text{an arbitrarily selected value} \quad (XI)$$

Where the $j^{th}$ signal-generating means is prepared to generate no signal in the presence of the $j^{th}$ target nucleic acid sequence at the $K^{th}$ detection temperature, an equation to allow the $S_{TjDK}$ to have an arbitrarily selected value.

According to an embodiment, signals may not be generated at a plurality of detection temperatures by adjusting characteristics of the $j^{th}$ signal-generating means.

The equation (XI) is presented for describing a plurality of equations as a single general equation.

Where a detection temperature is selected to generate no signal for each of the target nucleic acid sequences in the number of N, an equation allowing signal for a target nucleic acid sequence at the detection temperature to have an arbitrarily selected value. The equation may be represented by the equation (XI).

For instance, where the target nucleic acid sequences are in the number of N (i.e., N=3), a first signal-generating means for a first target nucleic acid sequence is designed to generate no signal at a second detection temperature and a third detection temperature and a second signal-generating means for a second target nucleic acid sequence is designed to generate no signal at a third detection temperature, the equation (XI) "$S_{TjDK}$=an arbitrarily selected value" comprises $S_{T1D2}$=an arbitrarily selected value, $S_{T1D3}$=an arbitrarily selected value and $S_{T2D3}$=an arbitrarily selected value. All or a portion of the three equations may be selected.

According to an embodiment, the additional equations comprise an equation or equations selected from an equation group represented by the equation (X) as well as an equation or equations selected from an equation group represented by the equation (XI).

The above-described embodiment describes two approaches to obtain the solution to at least one of the variables in the equations (1) to (N).

The first approach is to use the equation (X) as the additional equations in the number of ($N^2-N$).

In the equation (X), $RV_{Tj(D\alpha D\beta)}$ as a reference value is a predetermined value.

The reference value is obtained through a mathematical processing of signals provided by a signal-generating means at two detection temperatures and the second detection temperature. Such mathematical processing is a function of the signals. The function used in obtaining reference values include any function so long as it gives a relationship of change in signals provided by the signal-generating means at the two detection temperatures. For instance, the function may be presented as a mathematical processing such as addition, multiplication, subtraction and division of signals.

As described above, because $RV_{Tj(D\alpha D\beta)}$ as a reference value is a predetermined value, $RV_{Tj(D\alpha D\beta)}$ may serve as a convertor for (i) converting the variables ($S_{TjD1}$) to ($S_{TjDN}$) in the equations (1) to (N) into a variable selected from the variables ($S_{TjD1}$) to ($S_{TjDN}$).

According to an embodiment, the equation (X) comprising the reference value (RV) of the $j^{th}$ target nucleic acid sequence (Tj) is used to convert the variables ($S_{TjD1}$) to ($S_{TjDN}$) in the equations (1) to (N) into a variable selected from the variables ($S_{TjD1}$) to ($S_{TjDN}$).

The reference values, $RV_{Tj(D\alpha D\beta)}$ used in this invention may be obtained in various manners. For instance, the reference value may be given as an anticipated value. In considering a target sequence, a signal-generating means and detection temperatures, the reference value representing a relationship of change in signals at the detection temperatures may be anticipated. Alternatively, the reference value may be given as an experimental or practical value by performing experiments for obtaining the reference value.

According to an embodiment, $RV_{Tj(D\alpha D\beta)}$ is obtained by (i-1) incubating the $j^{th}$ target nucleic acid sequence with the $j^{th}$ signal-generating means for detection of the $j^{th}$ target nucleic acid sequence, (i-2) detecting signals at the $\alpha^{th}$ detection temperature and the $\beta^{th}$ detection temperature, and (i-3) then obtaining a difference between the signals detected at the $\alpha^{th}$ detection temperature and the $\beta^{th}$ detection temperature.

The term "difference between signals detected at the $\alpha^{th}$ detection temperature and the $\beta^{th}$ detection temperature" is an embodiment of a relationship of change in signals at the $\alpha^{th}$ detection temperature and the $\beta^{th}$ detection temperature.

According to an embodiment, the difference between the signals detected at the $\alpha^{th}$ detection temperature and the $\beta^{th}$ detection temperature comprises a difference to be obtained by mathematically processing the signal detected at the $\alpha^{th}$ detection temperature and the $\beta^{th}$ detection temperature.

According to an embodiment, where the mathematical processing is done, the characteristics of the signal should be vulnerable to the mathematical processing. In certain embodiments, the mathematical processing includes calculation (e.g., addition, multiplication, subtraction and division) using signals or obtaining other values derived from signals.

The difference between the signals at the $\alpha^{th}$ detection temperature and the $\beta^{th}$ detection temperature may be expressed as a numerical value or plot with signal characteristics.

The mathematical processing of the signals for obtaining the difference may be carried out by various calculation methods and their modifications.

In particular, the mathematical processing of the signals for obtaining the difference may be carried out by calculating a ratio between signals at the $\alpha^{th}$ detection temperature and the $\beta^{th}$ detection temperature.

For instance, the ratio of the end-point intensity of the signal detected at the $\beta^{th}$ detection temperature to the end-point intensity of the signal detected at the $\alpha^{th}$ detection temperature may be used as reference values.

The mathematical processing for obtaining the difference may be carried out in various fashions. The mathematical processing may be carried out by use of a machine. For example, the signals may be undergone a mathematical processing by a processor in a detector or real-time PCR device. Alternatively, the signals may be manually undergone a mathematical processing particularly according to a predetermined algorithm.

According to an embodiment of the present invention, RVs for the target nucleic acid sequences in the number of N at detection temperatures in the number of N are different from each other.

Particularly, reference values for different target nucleic acid sequences calculated by using signals between the same two-detection temperatures are different. For example, where there are three target nucleic acid sequences, $RV_{T1(D\alpha D\beta)}$, $RV_{T2(D\alpha D\beta)}$ and $RV_{T3(D\alpha D\beta)}$ may be different from each other. According to an embodiment, signal generating means are used to provide different reference values for different target nucleic acid sequences.

Where the RV values are different from each other, a quantitative expression describing a difference extent may be varied depending on approaches for calculating the RV values.

According to an embodiment, signals for obtaining reference values may be processed by a common calculation method to provide a reference value for comparison, and then a difference extent between two reference values may be obtained by using the reference value for comparison.

According to an embodiment, the common calculation method is division of two signals.

For instance, while two signals are processed by subtraction for obtaining reference values used to analyze signals according to the present method, the two signals may be processed by division for obtaining a reference value for comparison.

According to an embodiment, one reference value is at least 1.1-fold, 1.2-fold, 1.3-fold, 1.5-fold, 1.7-fold, 2-fold, 2.5-fold, 3-fold, 3.5-fold, 4-fold, 5-fold or 10-fold larger than the other reference value.

According to an embodiment, some of reference values used in the present method may be the same to one another.

According to an embodiment of this invention, the signal-generating means for the reference value may be the same as those for the detection of the target nucleic acid sequences.

According to an embodiment, the incubation conditions for obtaining the reference values are the same as those for the sample.

For a target nucleic acid sequence, the reference values may be obtained under various reaction conditions including the amounts of components (e.g. the target nucleic acid sequence, signal-generating means, enzymes and dNTPs), buffer pH or reaction time. According to an embodiment of this invention, the reference value may be obtained under reaction conditions sufficient to provide a saturated signal at the reaction completion. According to an embodiment of this invention, the difference between the signals obtained in obtaining the reference value has a certain range and the reference value is selected within the certain range or with referring to the certain range. According to an embodiment of this invention, the reference value may be selected with maximum or minimum value of the certain range or with referring to maximum or minimum value of the certain range. Particularly, the reference value may be modified in considering standard variation of the reference values obtained in various conditions, acceptable error ranges, specificity or sensitivity.

$f(S_{TjD\alpha}, S_{TjD\beta})$ in "$f(S_{TjD\alpha}, S_{TjD\beta})=RV_{Tj(D\alpha D\beta)}$" may be presented by a mathematical expression for calculating $RV_{Tj(D\alpha D\beta)}$.

According to an embodiment, $f(S_{TjD\alpha}, S_{TjD\beta})=RV_{Tj(D\alpha D\beta)}$ comprises $S_{TjD\alpha}/S_{TjD\beta}=RV_{TjD\alpha/D\beta}$ (XII) or $S_{TjD\beta}/S_{TjD\alpha}=RV_{TjD\beta/D\alpha}$ (XIII).

Where RV is obtained by using a ratio between signals at the $\alpha^{th}$ detection temperature and the $\beta^{th}$ detection temperature, "$f(S_{TjD\alpha}, S_{TjD\beta})$" in "$f(S_{TjD\alpha}, S_{TjD\beta})=RV_{Tj(D\alpha D\beta)}$" may be presented by a mathematical expression for calculating ratio between $S_{TjD\alpha}$ and $S_{TjD\beta}$. In the term "$RV_{Tj(D\alpha D\beta)}$", Tj(DαDβ) indicates that a calculated RV corresponds to the reference value for the $j^{th}$ target nucleic acid sequence obtained by calculating a difference between signals at the $\alpha^{th}$ detection temperature (Dα) and the $\beta^{th}$ detection temperature (Dβ).

Upon determining a method for calculation RV, the term "Tj(DαDβ)" may be specifically expressed in considering the calculation method. For example, the term "$RV_{TjD\alpha/D\beta}$" means a reference value for the $j^{th}$ target nucleic acid sequence obtained by calculating a ratio of a signal detected at the $\alpha^{th}$ detection temperature to a signal detected at the $\beta^{th}$ detection temperature.

According to an embodiment, $RV_{TjD\alpha/D\beta}$ is obtained by (i-1) incubating the $j^{th}$ target nucleic acid sequence with the $j^{th}$ signal-generating means for detection of the $j^{th}$ target nucleic acid sequence, (i-2) detecting signals at the $\alpha^{th}$ detection temperature and the $\beta^{th}$ detection temperature, and (i-3) then calculating a ratio of a signal detected at the $\alpha^{th}$ detection temperature to a signal detected at the $\beta^{th}$ detection temperature; $RV_{TjD\alpha/D\beta}$ is obtained by performing the steps (i-1) and (i-2) and then calculating a ratio of the signal detected at the $\beta^{th}$ detection temperature to the signal detected at the $\alpha^{th}$ detection temperature.

According to an embodiment, the additional equations in the number of $N^2-N$ are selected from the groups of the following equations:

$$S_{TjD\alpha}/S_{TjD\beta}=RV_{TjD\alpha/D\beta} \quad (XII)$$

$$S_{TjD\beta}/S_{TjD\alpha}=RV_{TjD\beta/D\alpha} \quad (XIII)$$

wherein the equation for each $j^{th}$ target nucleic acid at the $\alpha^{th}$ detection temperature and the $\beta^{th}$ detection temperature is selected from the equations (XII) and (XIII). Particularly, the equation for each $j^{th}$ target nucleic acid at the $\alpha^{th}$ detection temperature and the $\beta^{th}$ detection temperature is selected from one of the equations (XII) and (XIII).

The additional equation(s) selected from an equation group represented by the equation (X) together with the equations (1) to (N) are used for obtaining solutions to at least one of the variables.

In the particular example (N=3), the equation (XII) or (XIII) is presented as follows:

(i) in the case of j=1;
$f(S_{T1D1}, S_{T1D2})=RV_{T1(D1D2)}$ may comprise:

$$S_{T1D1}/S_{T1D2}=RV_{T1D1/D2} \text{ or } S_{T1D2}/S_{T1D1}=RV_{T1D2/D1}$$

$f(S_{T1D1}, S_{T1D3})=RV_{T1(D1D3)}$ may comprise:

$$S_{T1D1}/S_{T1D3}=RV_{T1D1/D3} \text{ or } S_{T1D3}/S_{T1D1}=RV_{T1D3/D1}$$

$f(S_{T1D2}, S_{T1D3})=RV_{T1(D2D3)}$ may comprise:

$$S_{T1D2}/S_{T1D3}=RV_{T1D2/D3} \text{ or } S_{T1D3}/S_{T1D2}=RV_{T1D3/D2}$$

(ii) in the case of j=2;
$f(S_{T2D1}, S_{T2D2})=RV_{T2(D1D2)}$ may comprise:

$$S_{T2D1}/S_{T2D2}=RV_{T2D1/D2} \text{ or } S_{T2D2}/S_{T2D1}=RV_{T2D2/D1}$$

$f(S_{T2D1}, S_{T2D3})=RV_{T2(D1D3)}$ may comprise:

$$S_{T2D1}/S_{T2D3}=RV_{T2D1/D3} \text{ or } S_{T2D3}/S_{T2D1}=RV_{T2D3/D1}$$

$f(S_{T2D2}, S_{T2D3})=RV_{T2(D2D3)}$ may comprise:

$$S_{T2D2}/S_{T2D3}=RV_{T2D2/D3} \text{ or } S_{T2D3}/S_{T2D2}=RV_{T2D3/D2}$$

(ii) in the case of j=3
$f(S_{T3D1}, S_{T3D2})=RV_{T3(D1D2)}$ may comprise:

$$S_{T3D1}/S_{T3D2}=RV_{T3D1/D2} \text{ or } S_{T3D2}/S_{T3D1}=RV_{T3D2/D1}$$

$f(S_{T3D1}, S_{T3D3})=RV_{T3(D1D3)}$ may comprise:

$$S_{T3D1}/S_{T3D3}=RV_{T3D1/D3} \text{ or } S_{T3D3}/S_{T3D1}=RV_{T3D3/D1}$$

$f(S_{T3D2}, S_{T3D3})=RV_{T3(D2D3)}$ may comprise:

$$S_{T3D2}/S_{T3D3}=RV_{T3D2/D3} \text{ or } S_{T3D3}/S_{T3D2}=RV_{T3D3/D2}$$

According to an embodiment, a plurality of equations for calculating RV for a certain target nucleic acid sequence at selected two detection temperatures may be presented. According to an embodiment, in such case, a single equation among a plurality of equations is selected. For example, where j=1 (i.e., T1) and two detection temperatures are 60° C. (D1) and 72° C. (D2), "$f(S_{T1D1}, S_{T1D2})=RV_{T1(D1D2)}$" may comprise $S_{T1D1}/S_{T1D2}=RV_{T1D1/D2}$ and $S_{T1D2}/S_{T1D1}=RV_{T1D2/D1}$. A single equation among the two particular equations is used to calculate RV for the target nucleic acid sequence (T1).

Where signals at the detection temperature D1 are analyzed, six (6) additional equations selected from the equations described above may be selected as follows:

$S_{T1D1}/S_{T1D2}=RV_{T1D1/D2}$ (or $S_{T1D2}/S_{T1D1}=RV_{T1D2/D1}$)

$S_{T1D1}/S_{T1D3}=RV_{T1D1/D3}$ (or $S_{T1D3}/S_{T1D1}=RV_{T1D3/D1}$)

$S_{T2D1}/S_{T2D2}=RV_{T2D1/D2}$ (or $S_{T2D2}/S_{T2D1}=RV_{T2D2/D1}$)

$S_{T2D1}/S_{T2D3}=RV_{T2D1/D3}$ (or $S_{T2D3}/S_{T2D1}=RV_{T2D3/D1}$)

$S_{T3D1}/S_{T3D2}=RV_{T3D1/D2}$ (or $S_{T3D2}/S_{T3D1}=RV_{T3D2/D1}$)

$S_{T3D1}/S_{T3D3}=RV_{T3D1/D3}$ (or $S_{T3D3}/S_{T3D1}=RV_{T3D3/D1}$)

Finally, the equation set for obtaining solutions to variables may include the following:

$S_{T1D1}+S_{T2D1}+S_{T3D1}=S_{D1}$ $S_{T1D2}+S_{T2D2}+S_{T3D2}=S_{D2}$ $S_{T1D3}+S_{T2D3}+S_{T3D3}=S_{D3}$ $S_{T1D1}/S_{T1D2}=RV_{T1D1/D2}$ $S_{T1D1}/S_{T1D3}=RV_{T1D1/D3}$ $S_{T2D1}/S_{T2D2}=RV_{T2D1/D2}$ $S_{T2D1}/S_{T2D3}=RV_{T2D1/D3}$ $S_{T3D1}/S_{T3D2}=RV_{T3D1/D2}$ $S_{T3D1}/S_{T3D3}=RV_{T3D1/D3}$

Because $RV_{T1D1/D2}$, $RV_{T1D1/D3}$, $RV_{T2D1/D2}$, $RV_{T2D1/D3}$, $RV_{T3D1/D2}$ and $RV_{T3D1/D3}$ are an experimentally predetermined value, the solutions to the variables ($S_{T1D1}$), ($S_{T2D1}$), ($S_{T3D1}$), ($S_{T1D2}$), ($S_{T2D2}$), ($S_{T3D2}$), ($S_{T1D3}$), ($S_{T2D3}$) and ($S_{T3D3}$) may be obtained by the nine (9) equations.

The second approach to obtain the solution to at least one of the variables in the equations (1) to (N) is to use the equations (X) and (XI) as the additional equations in the number of ($N^2-N$). $S_{TjDK}$=an arbitrarily selected value in the equation (XI) may be selected with a proviso that the $j^{th}$ signal-generating means is prepared to generate substantially no signal in the presence of the $j^{th}$ target nucleic acid sequence at the $K^{th}$ detection temperature.

According to an embodiment, when the equation (XI) is selected as the additional equations, the other additional equations are selected from the equation (X) in which α or β for the $j^{th}$ target nucleic acid sequence is different from K for the $j^{th}$ target nucleic acid sequence.

In other words, when at least one equation is selected from an equation group represented by the equation (XI) as the additional equations, a portion of an equation group represented by the equation (X) in which α or β for the $j^{th}$ target nucleic acid sequence is the same as K for the $j^{th}$ target nucleic acid sequence is excluded from the other additional equations and the other additional equations are selected from the equation (X) except for the exclusion.

Therefore, the phrase used herein "when the equation (XI) is selected as the additional equations, the other additional equations are selected from the equation (X) in which α or β for the $j^{th}$ target nucleic acid sequence is different from K for the $j^{th}$ target nucleic acid sequence" may be also described as "when the equation (XI) is selected as the additional equations, the other additional equations are selected from the equation (X) except for an equation in which α or β for the $j^{th}$ target nucleic acid sequence is the same as K for the $j^{th}$ target nucleic acid sequence.

In a particular example in which three target nucleic acid sequences are analyzed (i.e. N=3 and j comprises 1, 2 and 3), a signal generating means for a target nucleic acid sequence (T1) is prepared to generate substantially no signal even in the presence of T1 at the 72° C. (D2) and 95° C. (D3) detection temperatures and a signal generating means for a target nucleic acid sequence (T2) is prepared to generate substantially no signal even in the presence of T2 at the 95° C. detection temperature (D3) (see FIG. 3A), the equation (XI) may comprise the following equations:

$S_{T1D2}=0$ (j=1 and K=2), $S_{T1D1}=0$ (j=1 and K=3), and $S_{T2D3}=0$ (j=2 and K=3).

Meanwhile, the equation (X) "f($S_{TjDα}$, $S_{TjDβ}$=$RV_{Tj(DαDβ)}$" may comprise:
(i) in the case of j=1;

$f(S_{T1D1},S_{T1D2})=RV_{T1(D1D2)}$, $f(S_{T1D1},S_{T1D3})=RV_{T1(D1D3)}$, $f(S_{T1D2},S_{T1D3})=RV_{T1(D2D3)}$, (ii) in the case of j=2;

$f(S_{T2D1},S_{T2D2})=RV_{T2(D1D2)}$, $f(S_{T2D1},S_{T2D3})=RV_{T2(D1D3)}$, $f(S_{T2D2},S_{T2D3})=RV_{T2(D2D3)}$, (ii) in the case of j=3

$f(S_{T3D1},S_{T3D2})=RV_{T3(D1D2)}$, $f(S_{T3D1},S_{T3D3})=RV_{T3(D1D3)}$, and $f(S_{T3D2},S_{T3D3})=RV_{T3(D2D3)}$.

Where "$S_{T2D3}=0$ (j=2 and K=3)" is used as one of the additional equation, the other additional equations may comprise two equations among the equation (X) (j=1), two equations among the equation (X) (j=3) and one equation among the equation (X) (j=2). In a certain embodiment, for such equation selection, equations in which α or β for the target nucleic acid sequence (j=2, i.e. T2) is the same as K (i.e., 3) for the target nucleic acid sequence (j=2, i.e. T2) are excluded. In other words, equations containing the D3 detection temperature among "f($S_{T2Dα}$, $S_{T2Dβ}$)=$RV_{T2(DαDβ)}$" are excluded.

Where signals at the detection temperature 60° C. (D1) are analyzed, equations comprising variables containing D1 may be selected as follows:

$S_{T2D3}=0$ $f(S_{T1D1}/S_{T1D2})=RV_{T1(D1D2)}$ $f(S_{T1D1}/S_{T1D3})=RV_{T1(D1D3)}$ $f(S_{T2D1}/S_{T2D2})=RV_{T2(D1D2)}$ $f(S_{T3D1}/S_{T3D2})=RV_{T3(D1D2)}$ $f(S_{T3D1}/S_{T3D3})=RV_{T3(D1D3)}$

Instead of using "$S_{T2D3}=0$ (j=2 and K=3)", $S_{T1D2}=0$ (j=1 and K=2) and $S_{T1D3}=0$ (j=1 and K=3) may be used as two of the additional equations. The other additional equations may comprise two equations among the equation (X) (j=2) and two equations among the equation (X) (j=3). In a certain embodiment, for such equation selection, equations in which α or β for the target nucleic acid sequence (j=1, i.e. T1) is the same as K (i.e., 2 or 3) for the target nucleic acid sequence (j=1, i.e. T1) are excluded. In other words, equations containing D2 or D3 as the detection temperature among "f($S_{T1D\alpha}$, $S_{T1D\beta}$)=$RV_{T1(D\alpha D\beta)}$," are excluded. Where signals at the detection temperature 60° C. (D1) are analyzed, equations comprising variables containing D1 may be selected as follows:

$$S_{T1D2}=0$$

$$S_{T1D3}=0$$

$$f(S_{T2D1}, S_{T2D2})=RV_{T2(D1D2)}$$

$$f(S_{T2D1}, S_{T2D3})=RV_{T2(D1D3)}$$

$$f(S_{T3D1}, S_{T3D2})=RV_{T3(D1D2)}$$

$$f(S_{T3D1}, S_{T3D3})=RV_{T3(D1D3)}$$

According to an embodiment, the additional equations in numbers of $N^2-N$ are selected from the groups of the following equations:

$$S_{TjD\alpha}/S_{TjD\beta}=RV_{TjD\alpha/D\beta} \quad \text{(XII)}$$

$$S_{TjD\beta}/S_{TjD\alpha}=RV_{TjD\beta/D\alpha} \quad \text{(XIII)}$$

$$S_{TjDK}=\text{an arbitrarily selected value} \quad \text{(XI)}$$

wherein the equation for each $j^{th}$ target nucleic acid at the $\alpha^{th}$ detection temperature and the $\beta^{th}$ detection temperature is selected from the equations (XII) and (XIII);

wherein when the equation (XI) is selected as the additional equation, the other additional equations are selected from the equations (XII) and (XIII) in which $\alpha$ or $\beta$ for the $j^{th}$ target nucleic acid sequence is different from K for the $j^{th}$ target nucleic acid sequence.

In a particular example in which three target nucleic acid sequences are analyzed (i.e. N=3 and j comprises 1, 2 and 3), a signal generating means for a target nucleic acid sequence (T1) is prepared to generate substantially no signal even in the presence of T1 at the 72° C. (D2) and 95° C. (D3) detection temperatures and a signal generating means for a target nucleic acid sequence (T2) is prepared to generate substantially no signal even in the presence of T2 at the 95° C. detection temperature (D3) (see FIG. 3A), there are various equation sets available for obtaining solutions to variables.

Where "$S_{T2D3}=0$ (j=2 and K=3)" is used as one of the additional equation, one of the equation sets for obtaining solutions to variables may include the following:

$$S_{T1D1}+S_{T2D1}+S_{T3D1}=S_{D1}$$

$$S_{T1D2}+S_{T2D2}+S_{T3D2}=S_{D2}$$

$$S_{T1D3}+S_{T2D3}+S_{T3D3}=S_{D3}$$

$$S_{T1D1}/S_{T1D2}=RV_{T1D1/D2}$$

$$S_{T1D1}/S_{T1D3}=RV_{T1D1/D3}$$

$$S_{T2D1}/S_{T2D2}=RV_{T2D1/D2}$$

$$S_{T2D3}=0$$

$$S_{T3D1}/S_{T3D2}=RV_{T3D1/D2}$$

$$S_{T3D1}/S_{T3D3}=RV_{T3D1/D3}$$

Because $RV_{T1D1/D2}$, $RV_{T1D1/D3}$, $RV_{T2D1/D2}$, $RV_{T3D1/D2}$ and $RV_{T3D1/D3}$ are constants determined experimentally or arbitrarily, the solutions to the variables ($S_{T1D1}$), ($S_{T2D1}$), ($S_{T3D1}$), ($S_{T1D2}$), ($S_{T2D2}$), ($S_{T3D2}$), ($S_{T1D3}$) and ($S_{T3D3}$) may be obtained by the nine (9) equations.

Instead of using "$S_{T2D3}=0$ (j=2 and K=3)", $S_{T1D2}=0$ (j=1 and K=2) and $S_{T1D3}=0$ (j=1 and K=3) may be used as two of the additional equations. One of the equation sets for obtaining solutions to variables may include the following:

$$S_{T1D1}+S_{T2D1}+S_{T3D1}=S_{D1}$$

$$S_{T1D2}+S_{T2D2}+S_{T3D2}=S_{D2}$$

$$S_{T1D3}+S_{T2D3}+S_{T3D3}=S_{D3}$$

$$S_{T1D2}=0$$

$$S_{T1D3}=0$$

$$S_{T2D1}/S_{T2D2}=RV_{T2D1/D2}$$

$$S_{T2D1}/S_{T2D3}=RV_{T2D1/D3}$$

$$S_{T3D1}/S_{T3D2}=RV_{T3D1/D2}$$

$$S_{T3D1}/S_{T3D3}=RV_{T3D1/D3}$$

Because $RV_{T2D1/D2}$, $RV_{T2D1/D3}$, $RV_{T3D1/D2}$ and $RV_{T3D1/D3}$ are constants determined experimentally or arbitrarily, the solutions to the variables ($S_{T1D1}$), ($S_{T2D1}$), ($S_{T3D1}$), ($S_{T2D2}$), ($S_{T3D2}$), ($S_{T2D3}$) and ($S_{T3D3}$) may be obtained by the nine (9) equations.

According to an embodiment, even though the $j^{th}$ signal-generating means is prepared to generate no signal in the presence of the $j^{th}$ target nucleic acid sequence at the $K^{th}$ detection temperature, the equation "$S_{TjDK}$=an arbitrarily selected value" may not be used as an additional equation. In such case, $RV_{Tj(D\alpha D\beta)}$ in which $\alpha$ or $\beta$ is the same as K may be an experimentally-obtained value.

According to an embodiment, when the $j^{th}$ signal-generating means is prepared to generate no signal in the presence of the $j^{th}$ target nucleic acid sequence at the $K^{th}$ detection temperature, $RV_{Tj(D\alpha D\beta)}$ in which $\alpha$ or $\beta$ is the same as K is an arbitrarily selected value.

Particularly, when f($S_{TjD\alpha}$, $S_{TjD\beta}$) in the equation (X) is presented by a mathematical expression for calculating ratio between signals at the $\alpha^{th}$ detection temperature (D$\alpha$) and the $\beta^{th}$ detection temperature (D$\beta$), $RV_{Tj(D\alpha D\beta)}$ may be selected as an arbitrarily selected value.

Particularly, the arbitrarily selected value as $RV_{Tj(D\alpha D\beta)}$ may be selected such that the solution of $S_{TjDK}$ is rendered to be a value or around the value (e.g. "0" or around "0") in solving procedures of an equation set.

According to an embodiment, the arbitrarily selected value as $RV_{Tj(D\alpha D\beta)}$ may be the same as, greater or less than $RV_{Tj(D\alpha D\beta)}$ calculated with practically-obtained signal values.

Practically, even when the $j^{th}$ signal-generating means is prepared to generate no signal in the presence of the $j^{th}$ target nucleic acid sequence at the $K^{th}$ detection temperature, it is usually to generate signals with very weak intensities (e.g., background signal). Therefore, $RV_{Tj(D\alpha D\beta)}$ in which $\alpha$ or $\beta$ is the same as K may be obtained experimentally.

It is very interesting that the present method allows for quantification of a signal amount (e.g. signal intensity) generated by each of the signal-generating means. As described above, the solutions to the variables ($S_{T1D1}$) to ($S_{TNDN}$) permit quantification of a signal amount (e.g. signal intensity) generated by each of the signal-generating means, which may be applied to quantification of the target nucleic acid sequences.

Step (d): Obtaining Solutions to Variables

Finally, the solutions to at least one of the variables by the equations in the number of $N^2$ provided in the steps (b) and (c) for differentiating at least one of the signals of interest to be assigned to at least one of the target nucleic acid sequences in the number of N.

As described above, the equations in the number of $N^2$ provided in the steps (b) and (c) are used to obtain the solutions to at least one of the variables for differentiating at least one of the signals of interest to be assigned to at least one of the target nucleic acid sequences in the number of N, whereby the presence of at least one of the target nucleic acid sequences in the number of N may be determined.

Particularly, the solutions to at least one (e.g., at least two, at least three, at least four, at least five, at least six, at least nine, at least sixteen, at least twenty-five or at least $N^2$) of the variables are obtained by using the equations in the number of $N^2$ provided in the steps (b) and (c) for differentiating at least one (e.g., at least two, at least three, at least four, at least five, at least six, at least nine, at least sixteen, at least twenty-five or at least $N^2$) of the signals of interest to be assigned to at least one (e.g., at least two, at least three, at least four, at least five, at least six, at least seven, at least eight, at least nine and at least ten or at least N) of the target nucleic acid sequences.

According to an embodiment, the present method is used to obtain solutions (values) to the variables in the number of N each of which is selected from a variable group for each target nucleic acid sequence.

According to an embodiment, depending on approaches for generating signals, a threshold value may be employed to analyze whether the obtained solutions to the variables may be significant. A negative control, sensitivity or label used may be considered for determining the threshold value. According to an embodiment of this invention, a threshold value may be determined by user or automatically.

According to an embodiment, the threshold value is determined with referring to signals detected using only one of the target nucleic acid sequences at a detection temperature.

According to an embodiment, the threshold value may be used specifically to each target nucleic acid sequence or each detection temperature.

According to an embodiment, where signals are generated in a real-time manner associated with target amplification by PCR, the signals at each amplification cycle or some selected cycles are mathematically processed with the reference values and the calculation results are plotted against cycles and used for differentiating the signals of interest (e.g., determination of the presence of the target nucleic acid sequence).

According to an embodiment, a threshold value is applied to the plotting result to determine the significance of the signal of interest.

According to an embodiment of this invention, the target nucleic acid sequences comprises a nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

According to an embodiment of this invention, the nucleotide variation detected by the present invention is a SNP (single nucleotide polymorphism).

III. Kits for Differentiating Signals of Interest for Target Nucleic Acid Sequences In still another aspect of this invention, there is provided a kit for differentiating signals of interest for each of two target nucleic acid sequences comprising a first target nucleic acid sequence (T1) and a second target nucleic acid sequence (T2) in a sample, which are not differentiable by a single type of detector, comprising:

(a) a first signal-generating means for detection of the first target nucleic acid sequence (T1) and a second signal-generating means for detection of the second target nucleic acid sequence (T2) two signal-generating means for detection of the two target nucleic acid sequences; and (b) an instruction that describes the present method of the Aspect I titled as Differentiation of Signals of Interest for Two Target Nucleic Acid Sequences.

In further aspect of this invention, there is provided a kit for differentiating signals of interest for each of target nucleic acid sequences in the number of N in a sample, which are not differentiable by a single type of detector, comprising:

(a) signal-generating means in the number of N for detection of the target nucleic acid sequences in the number of N; and (b) an instruction that describes the present method of the Aspect II titled as Differentiation of Signals of Interest for at least Three Target Nucleic Acid Sequences.

Since the kits of this invention are prepared to perform the present methods, the common descriptions between them are omitted in order to avoid undue redundancy leading to the complexity of this specification.

All of the present kits described hereinabove may optionally include the reagents required for performing target amplification reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The components of the kit may be present in separate containers, or multiple components may be present in a single container.

The instructions for describing or practicing the methods of the present invention may be recorded on a suitable recording medium. For example, the instructions may be printed on a substrate, such as paper and plastic. In other embodiments, the instructions may be present as an electronic storage data file present on a suitable computer readable storage medium such as CD-ROM and diskette. In yet other embodiments, the actual instructions may not be present in the kit, but means for obtaining the instructions from a remote source, e.g. via the internet, are provided. An example of this embodiment is a kit that includes a web address where the instructions can be viewed and/or from which the instructions can be downloaded.

IV. Storage Medium and Device for Differentiating Signals of Interest for Target Nucleic Acid Sequences Since the storage medium, the device and the computer program of the prevent invention described hereinbelow are intended to perform the present methods in a computer, the common descriptions between them are omitted in order to avoid undue redundancy leading to the complexity of this specification.

In still further aspect of this invention, there is provided a computer readable storage medium containing instructions to configure a processor to perform a method for differentiating signals of interest for each of two target nucleic acid sequences comprising a first target nucleic acid sequence (T1) and a second target nucleic acid sequence (T2) in a sample, which are not differentiable by a single type of detector, the method comprising:

(a) receiving signals detected at a first detection temperature (D1) and a second detection temperature (D2); wherein the first target nucleic acid sequence (T1) in the sample is detected by a first signal-generating means and the second target nucleic acid sequence (T2) in the sample is detected by a second signal-generating means; wherein the signals of interest to be generated by the two signal-generating means are not differentiated by a single type of detector;

(b) providing the following two equations each of which comprises variables representing the signals of interest generated at each detection temperature for the two target nucleic acid sequences;

$$S_{T1D1} + S_{T2D1} = S_{D1} \quad (I)$$

$$S_{T1D2} + S_{T2D2} = S_{D2} \quad (II)$$

wherein ($S_{D1}$) is a signal detected at the first detection temperature, ($S_{D2}$) is a signal detected at the second detection temperature; ($S_{T1D1}$) is a variable representing a signal of interest generated by the first signal-generating means at the first detection temperature, ($S_{T2D1}$) is a variable representing a signal of interest generated by the second signal-generating means at the first detection temperature, ($S_{T1D2}$) is a variable representing a signal of interest generated by the first signal-generating means at the second detection temperature, ($S_{T2D2}$) is a variable representing a signal of interest generated by the second signal-generating means at the second detection temperature; and the total number of variables is four;

(c) providing two additional equations each of which comprises at least one variable selected from the group consisting of the four variables, ($S_{T1D1}$), ($S_{T2D1}$), ($S_{T1D2}$) and ($S_{T2D2}$); and (d) obtaining solutions to at least one of the variables by the four equations provided in the steps (b) and (c) for differentiating at least one of the signals of interest to be assigned to at least one of the two target nucleic acid sequences.

According to an embodiment of the present invention, the equations (I) and (II) as well as the additional equations is stored in the computer readable storage medium. According to an embodiment of the present invention, $RV_{T1(D1D2)}$ as a reference value (RV) of the first target nucleic acid sequence (T1) and/or $RV_{T2(D1D2)}$ as a reference value (RV) of the second target nucleic acid sequence (T2) is stored in the computer readable storage medium.

According to an embodiment of the present invention, the computer readable storage medium contains instructions to provide the equations (I) and (II) as well as the additional equations. According to an embodiment of the present invention, the computer readable storage medium contains instructions to input $RV_{T1(D1D2)}$ and/or $RV_{T2(D1D2)}$ in performing the method. According to an embodiment of the present invention, the computer readable storage medium further contains instructions to configure a processor to perform a method for obtaining $RV_{T1(D1D2)}$ and/or $RV_{T2(D1D2)}$.

In another aspect of this invention, there is provided a computer program to be stored on a computer readable storage medium to configure a processor to perform a method for differentiating signals of interest for each of two target nucleic acid sequences comprising a first target nucleic acid sequence (T1) and a second target nucleic acid sequence (T2) in a sample, which are not differentiable by a single type of detector, the method comprising:

(a) receiving signals detected at a first detection temperature (D1) and a second detection temperature (D2); wherein the first target nucleic acid sequence (T1) in the sample is detected by a first signal-generating means and the second target nucleic acid sequence (T2) in the sample is detected by a second signal-generating means; wherein the signals of interest to be generated by the two signal-generating means are not differentiated by a single type of detector;

(b) providing the following two equations each of which comprises variables representing the signals of interest generated at each detection temperature for the two target nucleic acid sequences;

$$S_{T1D1} + S_{T2D1} = S_{D1} \quad (I)$$

$$S_{T1D2} + S_{T2D2} = S_{D2} \quad (II)$$

wherein ($S_{D1}$) is a signal detected at the first detection temperature, ($S_{D2}$) is a signal detected at the second detection temperature; ($S_{T1D1}$) is a variable representing a signal of interest generated by the first signal-generating means at the first detection temperature, ($S_{T2D1}$) is a variable representing a signal of interest generated by the second signal-generating means at the first detection temperature, ($S_{T1D2}$) is a variable representing a signal of interest generated by the first signal-generating means at the second detection temperature, ($S_{T2D2}$) is a variable representing a signal of interest generated by the second signal-generating means at the second detection temperature; and the total number of variables is four;

(c) providing two additional equations each of which comprises at least one variable selected from the group consisting of the four variables, ($S_{T1D1}$), ($S_{T2D1}$), ($S_{T1D2}$) and ($S_{T2D2}$); and (d) obtaining solutions to at least one of the variables by the four equations provided in the steps (b) and (c) for differentiating at least one of the signals of interest to be assigned to at least one of the two target nucleic acid sequences.

According to an embodiment of the present invention, the computer program contains the equations (I) and (II) as well as the additional equations. According to an embodiment of the present invention, the computer program contains $RV_{T1(D1D2)}$ and/or $RV_{T2(D1D2)}$. According to an embodiment of the present invention, the computer program contains instructions to provide the equations (I) and (II) as well as the additional equations. According to an embodiment of the present invention, the computer program contains instructions to input $RV_{T1(D1D2)}$ and/or $RV_{T2(D1D2)}$ in performing the method. According to an embodiment of the present invention, the computer program further contains instructions to configure a processor to perform a method for obtaining $RV_{T1(D1D2)}$ and/or $RV_{T2(D1D2)}$.

The program instructions are operative, when preformed by the processor, to cause the processor to perform the present method described above. The program instructions may comprise an instruction to receive signals detected at a first detection temperature (D1) and a second detection temperature (D2), and an instruction to obtain solutions to at least one of the variables by using the four equations provided in the steps (b) and (c) for differentiating at least one of the signals of interest to be assigned to at least one of the two target nucleic acid sequences.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The data (e.g., intensity, amplification cycle number and detection temperature) associated with the signals may be received through several mechanisms. For example, the data may be acquired by a processor resident in a PCR data acquiring device. The data may be provided to the processor in real time as the data is being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system. After the data has been received or acquired, the data analysis process proceeds to obtain solutions to at least one of the variables by using the four equations provided in the steps (b) and (c) for differentiating at least one of the signals of interest to be assigned to at least one of the two target nucleic acid sequences. For example, the processor processes the received data to obtain a difference between the signals detected at the first detection temperature and the second detection temperature. The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In still another aspect of this invention, there is provided a device for differentiating signals of interest for each of two target nucleic acid sequences comprising a first target nucleic acid sequence (T1) and a second target nucleic acid sequence (T2) in a sample, which are not differentiable by a single type of detector, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a single type detector to detect signals at the first detection temperature and the second detection temperature.

According to an embodiment, the computer processor permits not only the single type of detector to detect signals at the first detection temperature and the second detection temperature but also to obtain solutions to at least one of the variables. The processor may be prepared in such a manner that a single processor can do two performances: direction of detection at two detection temperatures and calculation of the solutions. Alternatively, the processor unit may be prepared in such a manner that two processors do two performances, respectively.

The first essential feature of the device carries the processor to permit the device to detect signals at the two detection temperatures. According to an embodiment, where the signal is generated along with amplification of the target nucleic acid sequence, the device comprises a processor to permit the device to detect signals at the two detection temperatures at each amplification cycle.

The second essential feature of the device is to carry the processor to process signals at the two detection temperatures to obtain solutions to the variables. According to an embodiment, the solutions to the variables are expressed as numeric values by a mathematical processing.

According to an embodiment, the processor may be embodied by installing software into conventional devices for detection of target nucleic acid sequences (e.g. real-time PCR device). According to an embodiment, the device comprises a processor to permit the device to detect signals at two detection temperatures and to mathematically process two detection results.

In further aspect of this invention, there is provided a computer readable storage medium containing instructions to configure a processor to perform a method for differentiating signals of interest for each of target nucleic acid sequences in the number of N in a sample, which are not differentiable by a single type of detector, the method comprising:

(a) receiving signals detected at detection temperatures in the number of N; wherein each of the target nucleic acid sequences in the sample is detected by a corresponding signal-generating means; wherein the signals of interest to be generated by the signal-generating means in the number of N are not differentiated for each target nucleic acid sequence by a single type of detector; wherein N is an integer not less than 2;

(b) providing the following equations in the number of N each of which comprises variables representing the signals of interest generated at each detection temperature for the target nucleic acid sequences;

$$S_{T1D1} + S_{T2D1} + \ldots + S_{TND1} = S_{D1} \quad (1)$$

$$S_{T1D2} + S_{T2D2} + \ldots + S_{TND2} = S_{D2} \quad (2)$$

$$\vdots$$

$$S_{T1DN} + S_{T2DN} + \ldots + S_{TNDN} = S_{DN} \quad (N)$$

wherein each of($S_{D1}$) to ($S_{DN}$) is a signal detected at each detection temperature; each of($S_{T1D1}$) to ($S_{TNDN}$) is a variable representing a signal of interest generated by each signal-generating means at each detection temperature; and the total number of the variables is $N^2$;

(c) providing additional equations in the number of ($N^2$–N) each of which comprises at least one variable selected from the group consisting of the variables, ($S_{T1D1}$) to ($S_{TNDN}$); and (d) obtaining solutions to at least one of the variables by the equations in the number of $N^2$ provided in the steps (b) and (c) for differentiating at least one of the signals of interest to be assigned to at least one of the target nucleic acid sequences in the number of N.

According to an embodiment of the present invention, the equations (1) to (N) as well as the additional equations is stored in the computer readable storage medium. According to an embodiment of the present invention, $RV_{Tj(D\alpha D\beta)}$ as a reference value is stored in the computer readable storage medium.

According to an embodiment of the present invention, the computer readable storage medium contains instructions to provide the equations (1) to (N) as well as the additional equations. According to an embodiment of the present invention, the computer readable storage medium contains instructions to input $RV_{Tj(D\alpha D\beta)}$ in performing the method. According to an embodiment of the present invention, the computer readable storage medium further contains instructions to configure a processor to perform a method for obtaining $RV_{Tj(D\alpha D\beta)}$.

In still further aspect of this invention, there is provided a computer program to be stored on a computer readable storage medium to configure a processor to perform a method for differentiating signals of interest for each of target nucleic acid sequences in the number of N in a sample, which are not differentiable by a single type of detector, the method comprising:

(a) receiving signals detected at detection temperatures in the number of N; wherein each of the target nucleic acid sequences in the sample is detected by a corresponding signal-generating means; wherein the signals of interest to be generated by the signal-generating means in the number of N are not differentiated for each target nucleic acid sequence by a single type of detector; wherein N is an integer not less than 2;

(b) providing the following equations in the number of N each of which comprises variables representing the signals of interest detected at each detection temperature for the target nucleic acid sequences;

$$S_{T1D1} + S_{T2D1} + \ldots + S_{TND1} = S_{D1} \quad (1)$$

$$S_{T1D2} + S_{T2D2} + \ldots + S_{TND2} = S_{D2} \quad (2)$$

$$\vdots$$

$$S_{T1DN} + S_{T2DN} + \ldots + S_{TNDN} = S_{DN} \quad (N)$$

wherein each of($S_{D1}$) to ($S_{DN}$) is a signal detected at each detection temperature; each of($S_{T1D1}$) to ($S_{TNDN}$) is a variable representing a signal of interest provided by each signal-generating means at each detection temperature; and the total number of the variables is $N^2$;

(c) providing additional equations in the number of ($N^2$–N) each of which comprises at least one variable selected from the group consisting of the variables, ($S_{T1D1}$) to ($S_{TNDN}$); and (d) obtaining solutions to at least one of the variables by the equations in the number of $N^2$ provided in the steps (b) and (c) for differentiating at least one of the signals of interest to be assigned to at least one of the target nucleic acid sequences in the number of N.

According to an embodiment of the present invention, the computer program contains the equations (1) to (N) as well as the additional equations. According to an embodiment of the present invention, the computer program contains $RV_{Tj(D\alpha D\beta)}$. According to an embodiment of the present invention, the computer program contains instructions to provide the equations (1) to (N) as well as the additional equations. According to an embodiment of the present invention, the computer program contains instructions to input $RV_{Tj(D\alpha D\beta)}$ in performing the method. According to an embodiment of the present invention, the computer program further contains instructions to configure a processor to perform a method for obtaining $RV_{Tj(D\alpha D\beta)}$.

The program instructions are operative, when preformed by the processor, to cause the processor to perform the present method described above. The program instructions may comprise an instruction to receive signals detected at detection temperatures in the number of N, and an instruction to obtain solutions to at least one of the variables for differentiating at least one of the signals of interest to be assigned to at least one of the target nucleic acid sequences in the number of N.

In another aspect of this invention, there is provided a device for differentiating signals of interest for each of target nucleic acid sequences in the number of N in a sample, which are not differentiable by a single type of detector, comprising (a) a computer processor and (b) the above-described computer readable storage medium coupled to the computer processor.

According to an embodiment, the device further comprises a reaction vessel to accommodate the sample and signal-generating means, a temperature controlling means to control temperatures of the reaction vessel and/or a single type detector to detect signals at detection temperatures in the number of N.

According to an embodiment, the computer processor permits not only the single type of detector to detect signals at detection temperatures in the number of N but also to obtain solutions to at least one of the variables. The processor may be prepared in such a manner that a single processor can do two performances: direction of detection at detection temperatures in the number of N and calculation of the solutions. Alternatively, the processor unit may be prepared in such a manner that two processors do two performances, respectively.

The first essential feature of the device carries the processor to permit the device to detect signals at detection temperatures in the number of N. According to an embodiment, where the signal is generated along with amplification of the target nucleic acid sequence, the device comprises a processor to permit the device to detect signals at detection temperatures in the number of N at each amplification cycle.

The second essential feature of the device is to carry the processor to process signals at detection temperatures in the number of N to obtain solutions to the variables. According to an embodiment, the solutions to the variables are expressed as numeric values by a mathematical processing.

According to an embodiment, the processor may be embodied by installing software into conventional devices for detection of target nucleic acid sequences (e.g. real-time PCR device). According to an embodiment, the device comprises a processor to permit the device to detect signals at detection temperatures in the number of N and to mathematically process detection results.

The features and advantages of this invention will be summarized as follows:

(a) The present invention employing different detection temperatures enables to detect a plurality of target nucleic acid sequences in conventional real-time manners even with a single type of label in a single reaction vessel. The conventional technologies detect a plurality of target nucleic acid sequences by a melting analysis after target amplification. Unlikely, the present invention does not require a melting analysis after target amplification, such that the time for analysis is greatly reduced.

(b) The present invention permits to obtain an individual signal value (i.e., variable) contained in a total signal detected at detection temperatures by using mathematical equations. The present invention based on equation-solving approach enables to obtain the individual signal value in a systematical manner, thereby providing analysis results in much more accurate and convenient manner.

(c) The present invention has a tremendous freedom in selecting signal-generating means for detection of target nucleic acid sequences. In particular, the present invention may use (i) signal-generating means to generate signals at all detection temperatures for each target nucleic acid sequence, (ii) signal-generating means to generate signals at all detection temperatures for a portion of target nucleic acid sequences and signal-generating means to generate signals at a portion of detection temperatures for a portion of target nucleic acid sequences, and (iii) signal-generating means with different signal-generating temperature range for different target nucleic acid sequences.

(d) The present invention embodies our findings in which there is a certain relationship (pattern or rule) in change of signals generated by signal-generating means between two detection temperatures. In particular, the present invention introduces a novel concept "a reference value representing such relationship (pattern or rule) in change of signals" for detecting target nucleic acid sequences. The present invention uses equations containing reference values. The utilization of the reference value enables to provide the individual signal value in much more logical manner and provide additional equations in much more convenient manner.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Two Target Detection by Performing TaqMan Real-Time PCR Comprising Signal Detection at Different Temperatures and Solving Equations We examined whether two target nucleic acid sequences can be detected in a single reaction vessel by using a single detection channel and TaqMan real-time PCR comprising signal detection at different temperatures. Equations with variables representing signals of interest detected at the two detection temperature were setup and solved for differentiating the signals of interest and determining the presence or absence of target nucleic acid sequences.

Taq DNA polymerase having a 5' nuclease activity was used for the extension of upstream primers and downstream primers and the cleavage of a TaqMan probe. Genomic DNA of *Neisseria gonorrhoeae* (NG) and genomic DNA of *Chlamydia trachomatis* (CT) were used as target nucleic acid sequences. Four types of samples (NG, CT, NG+CT and no template control) were prepared and analyzed.

TaqMan real-time PCR was employed to detect NG and CT. If a target nucleic acid sequence is present, a TaqMan probe is cleaved and a labeled fragment is released. An amplification curve can be obtained by measuring a signal from the labeled fragment.

A TaqMan probe for NG is labeled with a fluorescent reporter molecule (Quasar 670) at its 5'-end and a quencher molecule at its 3'-end (SEQ ID NO: 3) and a TaqMan probe for CT with a fluorescent reporter molecule (Quasar 670) at its 5'-end and a quencher molecule in its inner part (BHQ-2) (SEQ ID NO: 6).

"60° C." and "72° C." were selected as signal detection temperatures.

The following equations were set up with variables representing signals of interest provided by NG and CT at the 60° C. and 72° C. detection temperatures, reference values (RVs) of the NG and CT and signals detected at the two temperatures at every cycle during PCR.

$$S_{T1D1} + S_{T2D1} = S_{D1}$$

$$S_{T1D2} + S_{T2D2} = S_{D2}$$

$$S_{T1D1}/S_{T1D2} = RV_{T1D1/D2}$$

$$S_{T2D1}/S_{T2D2} = RV_{T2D1/D2} \qquad \text{<Equation set 1>}$$

$S_{T1D1}$ is a variable representing a signal of interest provided by NG at 60° C. detection temperature wherein T1 represents NG, D1 represents 60° C. detection temperature;

$S_{T2D1}$ is a variable representing a signal of interest provided by CT at 60° C. detection temperature wherein T2 represents CT target, D1 represents 60° C. detection temperature;

$S_{T1D2}$ is a variable representing a signal of interest provided by NG at 72° C. detection temperature, wherein T1 represents NG, D2 represents 72° C. detection temperature;

$S_{T2D2}$ is a variable representing a signal of interest provided by CT at 72° C. detection temperature, wherein T2 represents CT, D2 represents 72° C. detection temperature;

$S_{D1}$ is a constant and obtained experimentally by measuring a signal at 60° C.;

$S_{D2}$ is a constant and obtained experimentally by measuring signals at 72° C.;

$RV_{T1D1/D2}$ is a constant and obtained experimentally by calculating (RFU at 60° C. RFU at 72° C. at the end-point)

wherein RFUs are those measured for NG solely containing-sample. T1 represents NG, and D1 and D2 represent 60° C. and 72° C. detection temperatures, respectively; and $RV_{T2D1/D2}$ is a constant and obtained experimentally by calculating RFU at 60° C. RFU at 72° C. at the end-point wherein RFUs are those measured for CT solely containing-sample. T2 represents CT target, and D1 and D2 represent 60° C. and 72° C. detection temperatures, respectively.

One of approaches for solving the equation set is as follows: Linear simultaneous equation with two variables each of which is selected for each target sequence is newly established and then solutions to the two variables are obtained. For instance, the following four linear simultaneous equations may be set up:

$S_{T1D1} + S_{T2D1} = S_{D1}$ $1/RV_{T1D1/D2} \times S_{T1D1} + 1/RV_{T2D1/D2} \times S_{T2D1} = S_{D2}$  Simultaneous equation 1

$RV_{T1D1/D2} \times S_{T1D2} + RV_{T2D1/D2} \times S_{T2D2} = S_{D1}$ $S_{T1D2} + S_{T2D2} = S_{D2}$  Simultaneous equation 2

$S_{T1D1} + RV_{T2D1/D2} \times S_{T2D2} = S_{D1}$ $1/RV_{T1D1/D2} \times S_{T1D1} + S_{T2D2} = S_{D2}$  Simultaneous equation 3

$RV_{T1D1/D2} \times S_{T1D2} + S_{T2D1} = S_{D1}$ $S_{T1D2} + 1/RV_{T2D1/D2} \times S_{T2D1} = S_{D2}$  Simultaneous equation 4

Afterwards, one of the four linear simultaneous equations is selected. The solutions to a corresponding variable at each cycle are obtained and then plotted. The plotting results may be considered as an amplification curve of a target sequence represented by a corresponding variable. Finally, the presence or absence of a target sequence is determined.

In this Example, the simultaneous equations 1 and 2 are employed.

The sequences of upstream primer, downstream primer, and probe used in this Example are:

```
NG-F
                              (SEQ ID NO: 1)
5'-TACGCCTGCTACTTTCACGCTIIIIIGTAATCAGATG-3'

NG-R
                              (SEQ ID NO: 2)
5'-CAATGGATCGGTATCACTCGCIIIIICGAGCAAGAAC-3'

NG-P
                              (SEQ ID NO: 3)
5'-[Quasar 670]TGCCCCTCATTGGCGTGTTTCG[BHQ-2]-3'

CT-F1
                              (SEQ ID NO: 4)
5'-TCCGAATGGATAAAGCGTGACIIIIIATGAACTCAC-3'

CT-R1
                              (SEQ ID NO: 5)
5'-AACAATGAATCCTGAGCAAAGGIIIIICGTTAGAGTC-3'

CT-P
                              (SEQ ID NO: 6)
5'-[Quasar 670]CATTGTAAAGA[T(BHQ-2)]

ATGGTCTGCTTCGACCG[C3 spacer]-3'

(I: Deoxyinosine)
```

The real-time PCR was conducted in the final volume of 20 μl containing a target nucleic acid sequence (1 pg of NG genomic DNA, 10 pg of CT genomic DNA or a mixture of 1 pg of NG genomic DNA and 10 pg of CT genomic DNA), 5 pmole of upstream primer (SEQ ID NO: 1) and 10 pmole of downstream primer (SEQ ID NO: 2) for NG target amplification, 1.5 pmole of TaqMan probe (SEQ ID NO: 3), 5 pmole of upstream primer (SEQ ID NO: 4) and 10 pmole of downstream primer (SEQ ID NO: 5) for CT target amplification, 3 pmole of TaqMan probe (SEQ ID NO: 6), and 5 μl of 4× Master Mix (final, 200 uM dNTPs, 2 mM $MgCl_2$, 2 U of Taq DNA polymerase). The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C. and 72° C. of each cycle.

As shown in FIG. 1A, signals were detected both at 60° C. and 72° C. in the presence of NG, CT, or NG+CT. No signal was detected in the absence of the target nucleic acid sequences. Reference values of each target were calculated using the signals of NG only sample or CT only sample and shown in FIG. 1B. As shown in FIG. 1B, reference values for NG and CT target were 1.8 and 5.8, respectively.

Figure 1C:
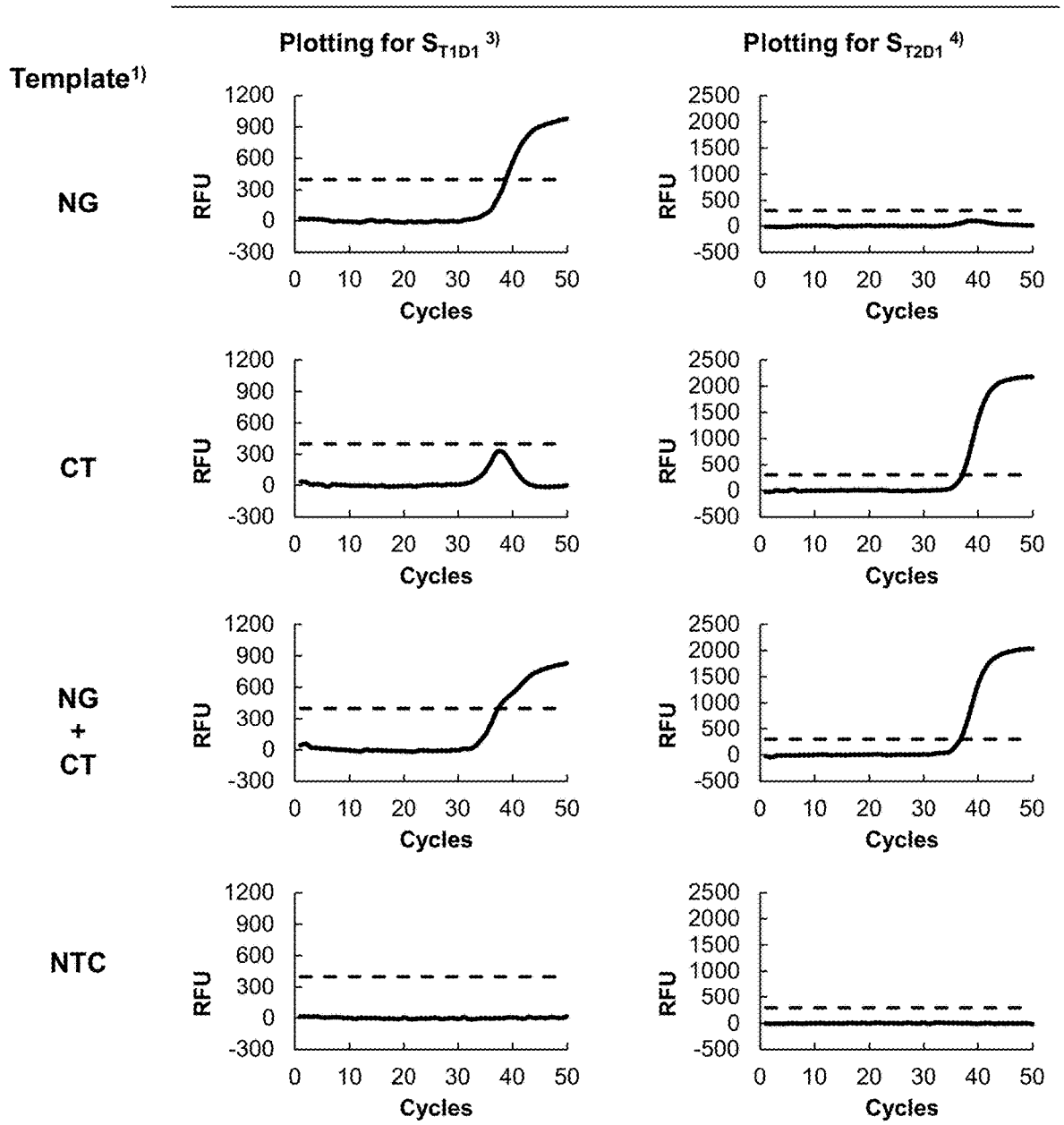
FIG. 1C represents plotting results for $S_{T1D1}$ and $S_{T2D1}$ obtained by solving the simultaneous equation 1. Experimentally obtained reference values were used. The dotted line represents a threshold which was determined with referring to the result of NG only sample and CT only sample in FIG. 1A to verify the significance of the obtained amplification curves.

FIG. 1C shows plotting results obtained by solving the simultaneous equation 1. The plotting result for $S_{T1D1}$ can be considered as an amplification curve of NG at 60° C. and the plotting result for $S_{T2D1}$ be as an amplification curve of CT at 60° C. Proper thresholds were selected with referring to the result of NG sample and CT sample to verify the significance of the obtained amplification curves. As shown in FIG. 1C, the amplification curves of the NG or the CT at 60° C. can show the presence or absence of target nucleic acid sequences in the each sample.

Figure 1D:
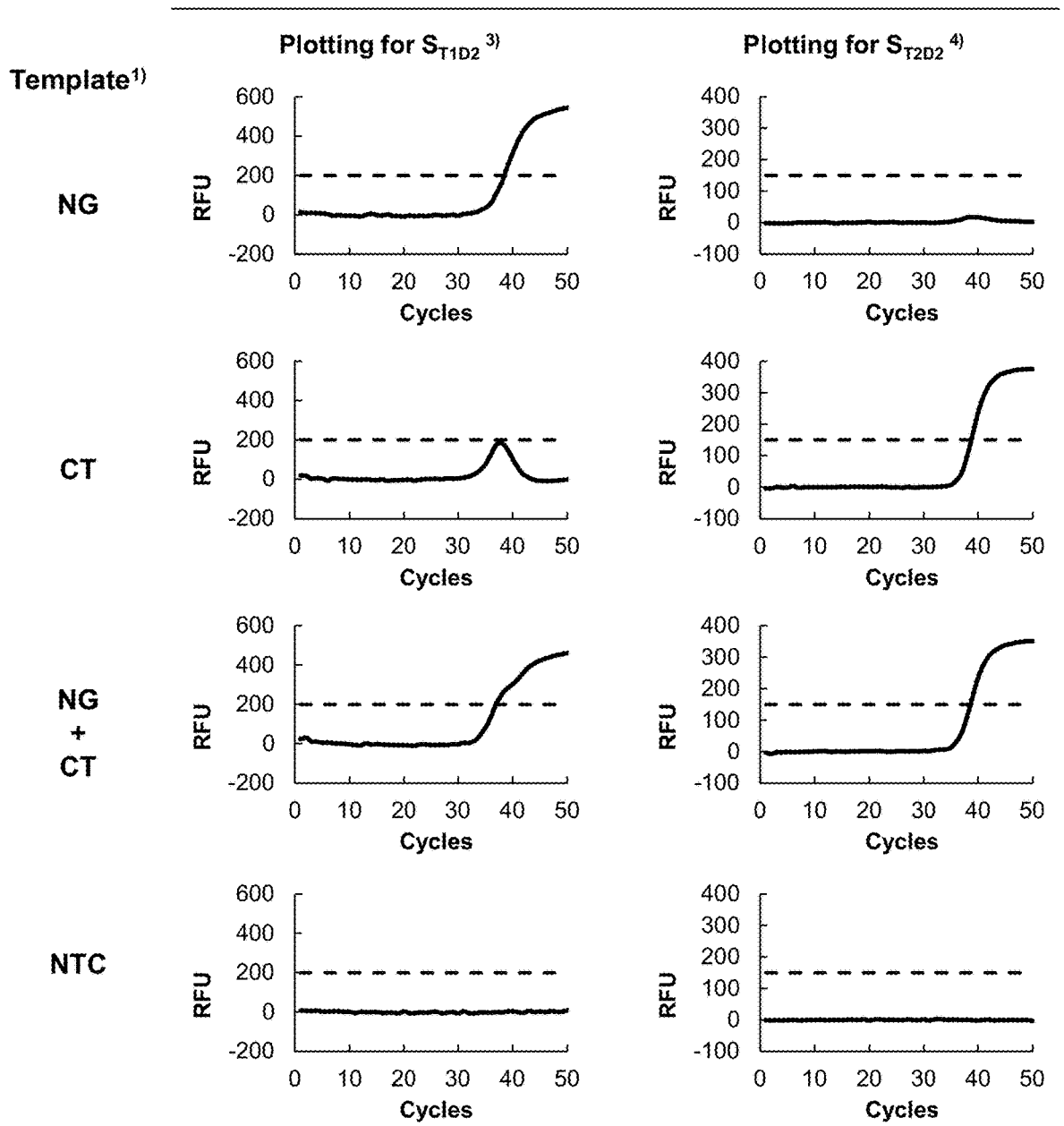
FIG. 1D represents plotting results for $S_{T1D2}$ and $S_{T2D2}$ obtained by solving the simultaneous equation 2. Experimentally obtained reference values were used. The dotted line represents a threshold.

FIG. 1D shows that the amplification curves of the NG or the CT at 72° C. can be obtained by solving the simultaneous equation 2, whereby, the presence or absence of target nucleic acid sequences in the each sample can be determined.

These results demonstrate that the approach of setting up and solving equations containing variables, reference values and signals measured at each detection temperature allows for extracting or differentiating the signal of interest for each target sequence from signals detected at each detection temperature.

Therefore, two target nucleic acid sequences can be detected in a single reaction vessel by using a single detection channel and TaqMan real-time PCR comprising signal detection at different temperatures, addressing that the present equation solving-approach permits to determine the presence of target sequences in much more convenient and reliable manner.

Example 2: Two Target Detection by Performing PTOCE Real-Time PCR Comprising Signal Detection at Different Temperatures and Solving Equations We examined whether two target nucleic acid sequences can be detected in a single reaction vessel by using a single detection channel and PTOCE real-time PCR comprising signal detection at different temperatures. Equations with variables representing signals of interest detected at the two detection temperature were setup and solved for differentiating the signals of interest and determining the presence or absence of the target nucleic acid sequences.

Taq DNA polymerase having a 5' nuclease activity was used for the extension of upstream primers and downstream primers, the cleavage of PTO, and the extension of PTO fragment. Genomic DNA of *Neisseria gonorrhoeae* (NG)

and genomic DNA of *Chlamydia trachomatis* (CT) were used as target nucleic acid sequences. Four types of samples (NG, CT, NG+CT and no template control) were prepared and analyzed.

PTOCE real-time PCR was used to detect CT and NG. If a target is present, a PTO is cleaved and a PTO fragment is produced. The PTO fragment is annealed to the capturing portion of the CTO, extended on the templating portion of the CTO and forms an extended duplex with CTO (Duplexed CTO). The formation of the extended duplex provides a signal and an amplification curve can be obtained by measuring the signal at the extended duplex-forming temperature.

"60° C." and "72° C." were selected as signal detection temperatures.

In this Example, the sequence and length of the extended duplex for CT is designed to provide a signal as it forms the duplex at 60° C. and 72° C. Meanwhile, the sequence and length of the extended duplex for NG is designed to provide a signal as it forms the duplex at 60° C., but not to provide a signal as it is dissociated not to forms the duplex at 72° C. In the detection temperature of 72° C., the signal for CT will be generated and detected. In the detection temperature of 60° C., the signal for NG as well as the signal for CT will be generated and detected.

The PTO and CTO are blocked with a carbon spacer at their 3'-ends to prohibit their extension. The CTO is labeled with a quencher molecule (BHQ-2) and a fluorescent reporter molecule (CAL Fluor Red 610) in its templating portion (SEQ ID NOs: 8 and 12).

$$S_{T1D1}+S_{T2D1}=S_{D1}$$

$$S_{T1D2}+S_{T2D2}=S_{D2}$$

$$S_{T1D2}=0$$

$$S_{T2D1}/S_{T2D2}=RV_{T2D1/D2} \quad \text{<Equation set 2>}$$

$S_{T1D1}$, $S_{T2D1}$, $S_{T1D2}$, $S_{T2D2}$, $S_{D1}$, $S_{D2}$ and $RV_{T2D1/D2}$ are defined as those in the Equation set 1.

In the Equation set 2, the equation $S_{T1D2}=0$ is used instead of $RV_{T1D1/D2}$ as a reference value of NG. Because the signal-generating means for NG was prepared to generate substantially no signal even in the presence of NG at the 72° C. detection temperature (D2), the equation $S_{T1D2}=0$ can be adopted in this Example.

The solutions to a corresponding variable at each cycle are obtained and then plotted.

$$S_{T1D1}+S_{T2D1}=S_{D1}$$

$$S_{T1D2}+S_{T2D2}=S_{D2}$$

$$S_{T1D1}/S_{T1D2}=RV_{T1D1/D2}$$

$$S_{T2D1}/S_{T2D2}=RV_{T2D1/D2} \quad \text{<Equation set 3>}$$

$S_{T1D1}$, $S_{T2D1}$, $S_{T1D2}$, $S_{T2D2}$, $S_{D1}$, $S_{D2}$, $RV_{T1D1/D2}$ and $RV_{T2D1/D2}$ are defined as those in the Equation set 1.

In this Example, the signal-generating means for NG was prepared to generate substantially no signal even in the presence of NG at the 72° C. detection temperature (D2). Nevertheless, a very weak signal (e.g., background signal) detected at the 72° C. detection temperature (D2) which is usually detected in practical experiments may be used to practically provide $RV_{T1D1/D2}$.

The solutions by using the Simultaneous equations 1 and 2 were obtained in the same manner as solving of the Equation set 1. The solutions to a corresponding variable at each cycle were obtained and then plotted.

$$S_{T1D1}+S_{T2D1}=S_{D1}$$

$$S_{T1D2}+S_{T2D2}=S_{D2}$$

$$S_{T1D1}/S_{T1D2}=RV_{T1D1/D2}$$

$$S_{T2D1}/S_{T2D2}=RV_{T2D1/D2} \quad \text{<Equation set 4>}$$

$S_{T1D1}$, $S_{T2D1}$, $S_{T1D2}$, $S_{T2D2}$, $S_{D1}$, $S_{D2}$, and $RV_{T2D1/D2}$ are defined as those in the Equation set 1.

In the Equation set 4, $RV_{T1D1/D2}$ is an arbitrary-selected constant value. In this Example, because the signal-generating means for NG was prepared to generate substantially no signal even in the presence of NG at the 72° C. detection temperature (D2), an arbitrary-selected value for $RV_{T1D1/D2}$ instead of experimentally-obtained values may be used. In this case, the arbitrary-selected value for $RV_{T1D1/D2}$ is $10^8$ which is much greater than experimentally-obtained values in the Equation set 3.

The solutions by using the Simultaneous equations 1 and 2 were obtained in the same manner as solving of the Equation set 1. The solutions to a corresponding variable at each cycle were obtained and then plotted.

The sequences of upstream primer, downstream primer, PTO, and CTO used in this Example are:

```
NG-F
                                       (SEQ ID NO: 1)
5'-TACGCCTGCTACTTTCACGCTIIIIIGTAATCAGATG-3'

NG-R
                                       (SEQ ID NO: 2)
5'-CAATGGATCGGTATCACTCGCIIIIICGAGCAAGAAC-3'

NG-PTO
                                       (SEQ ID NO: 7)
5'-GTACGCGATACGGGCCCCTCATTGGCGTGTTT

CG[C3 spacer]-3'

NG-CTO
                                       (SEQ ID NO: 8)
5'-[BHQ-2]TTTTTTTTTTTTTTTTTTTG[T(CAL Fluor Red 610)]ACTGCCCGTATCGCGTAC[C3 spacer]-3'

CT-F2
                                       (SEQ ID NO: 9)
5' -GAGTTTTAAAATGGGAAATTCTGGTIIIII

TTTGTATAAC-3'

CT-R2
                                       (SEQ ID NO: 10)
5'-CCAATTGTAATAGAAGCATTGGTTGIIIIITTATTGGAGA-3'

CT-PTO
                                       (SEQ ID NO: 11)
5'-GATTACGCGACCGCATCAGAAGCTGTCATTTTGGC

TGCG[C3 spacer]-3'

CT-CTO
                                       (SEQ ID NO: 12)
5'-[BHQ-2]GCGCTGGATACCCTGGACGA[T(CAL Fluor Red 610)]ATGTGCGGTCGCGTAATC[C3 spacer]-3'

(I: Deoxyinosine)
(Underlined letters indicate the 5'-tagging
portion of PTO)
```

The real-time PCR was conducted in the final volume of 20 μl containing a target nucleic acid sequence (10 pg of NG genomic DNA, 10 pg of CT genomic DNA or a mixture of 10 pg of NG genomic DNA and 10 pg of CT genomic DNA), 5 pmole of upstream primer (SEQ ID NO: 1) and 5 pmole of downstream primer (SEQ ID NO: 2) for NG target amplification, 3 pmole of PTO (SEQ ID NO: 7), 1 pmole of CTO (SEQ ID NO: 8), 5 pmole of upstream primer (SEQ ID NO: 9) and 5 pmole of downstream primer (SEQ ID NO: 10) for CT target amplification, 3 pmole of PTO (SEQ ID NO: 11), 1 pmole of CTO (SEQ ID NO: 12), and 10 µl of 2× Master Mix [final, 200 uM dNTPs, 2 mM MgCl$_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C. and 72° C. of each cycle.

As shown in FIG. 2A, signals were detected at 60° C. in the presence of NG, CT, or NG+CT. In the sole presence of CT, a signal was detected both at 60° C. and 72° C. In the sole presence of NG, a signal was detected at 60° C. but not at 72° C. No signal was detected in the absence of the target nucleic acid sequences. Reference values of each target were calculated using the signals of NG sample or CT sample and shown in FIG. 2B. As shown in FIG. 2B, reference values for NG and CT target obtained experimentally were 36.7 and 1.2, respectively.

FIGS. 2C-2H show plotting results obtained by solving the equation set 2, 3 and 4 respectively. The plotting result for $S_{T1D1}$, $S_{T2D1}$, $S_{T1D2}$, $S_{T2D2}$ can be considered as an amplification curve of NG at 60° C., an amplification curve of CT at 60° C., an amplification curve of NG at 72° C. and an amplification curve of CT at 72° C., respectively. Proper thresholds were selected with referring to the result of NG sample and CT sample to verify the significance of the obtained amplification curves.

Figure 2E:
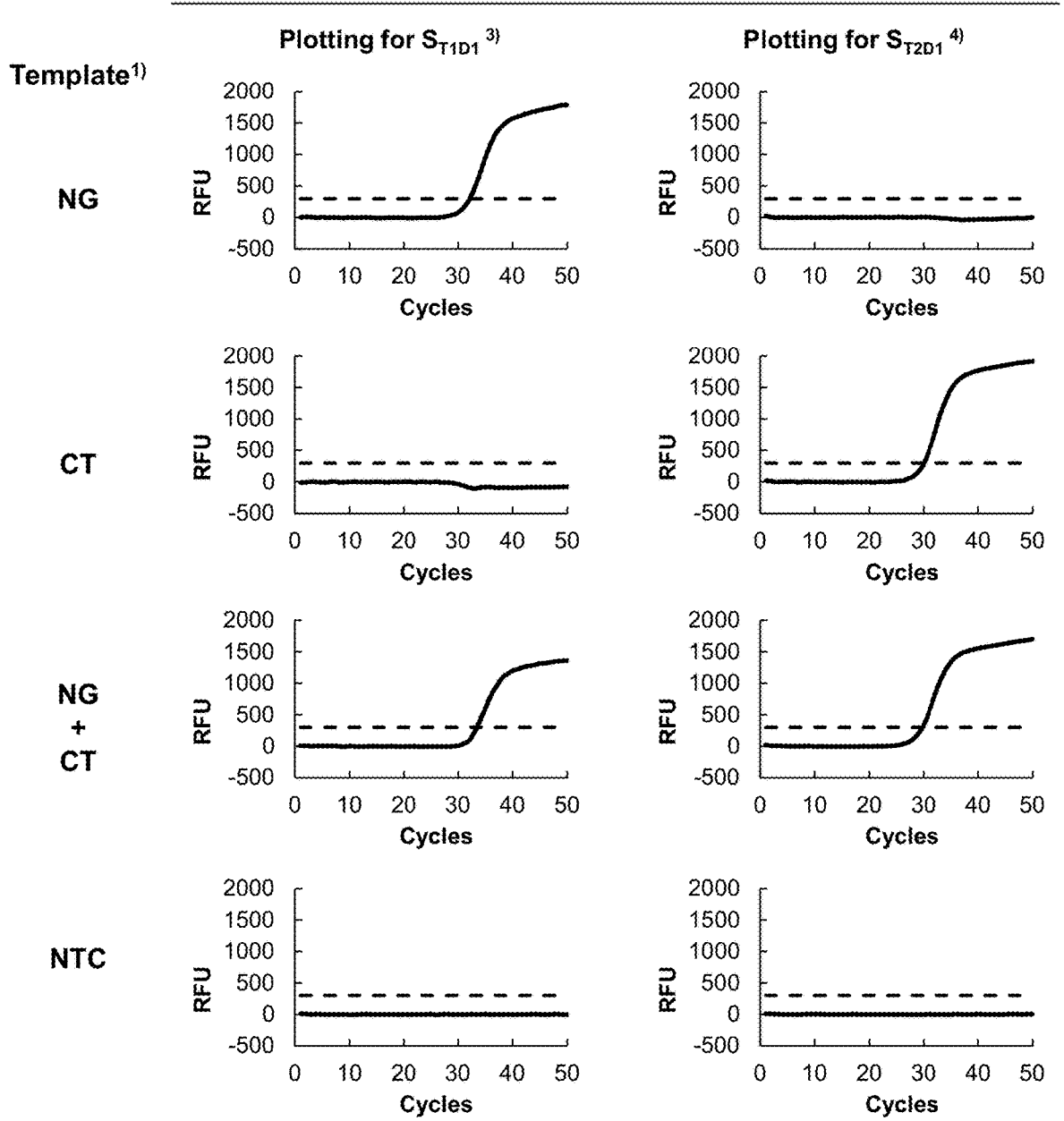
FIG. 2E represents plotting results for $S_{T1D1}$ and $S_{T2D1}$ obtained by solving the equation set 3 in which experimentally obtained reference values were used. The dotted line represents a threshold.
Figure 2F:
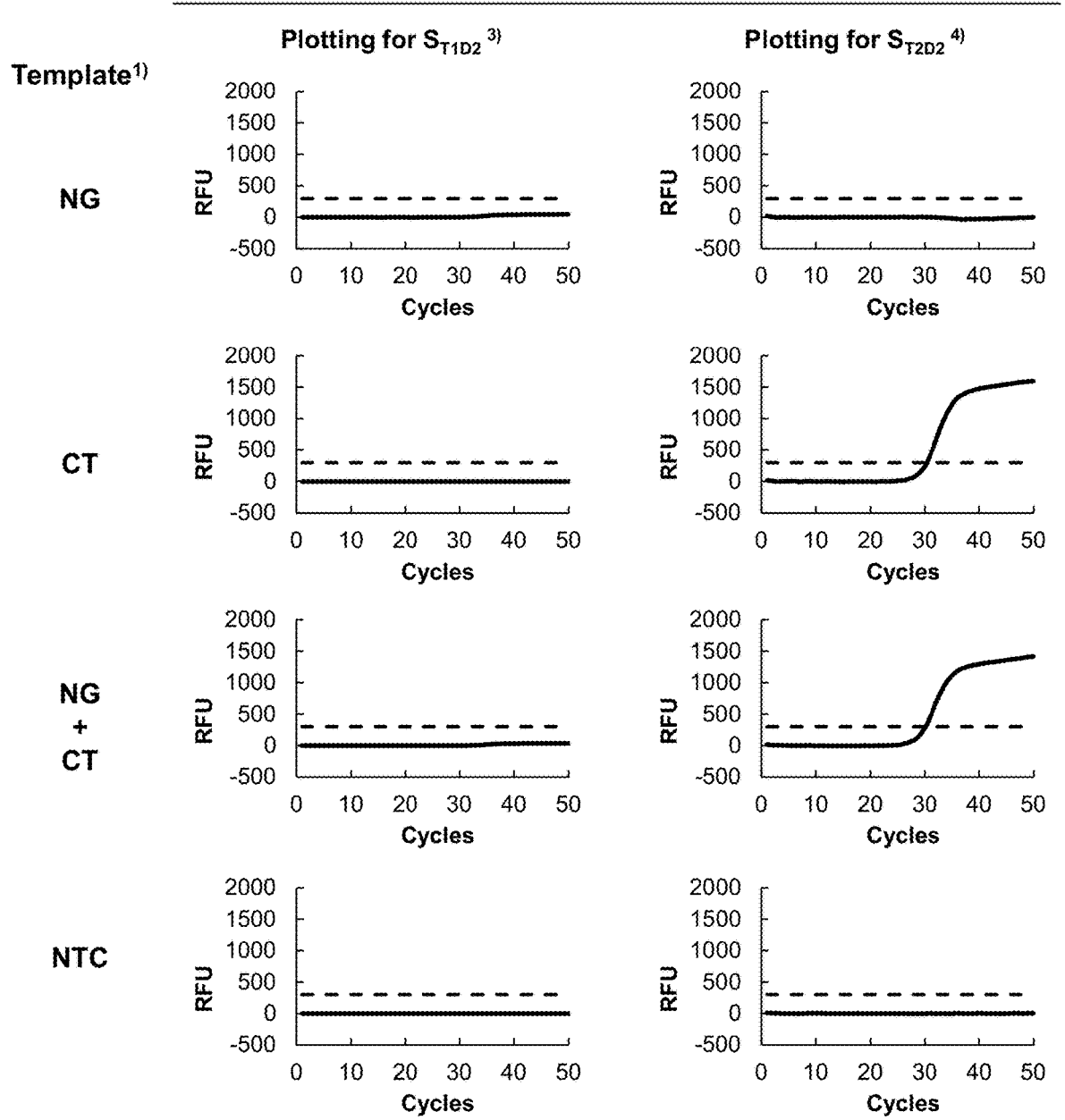
FIG. 2F represents plotting results for $S_{T1D2}$ and $S_{T2D2}$ obtained by solving the equation set 3 in which experimentally obtained reference values were used. The dotted line represents a threshold.
Figure 2G:
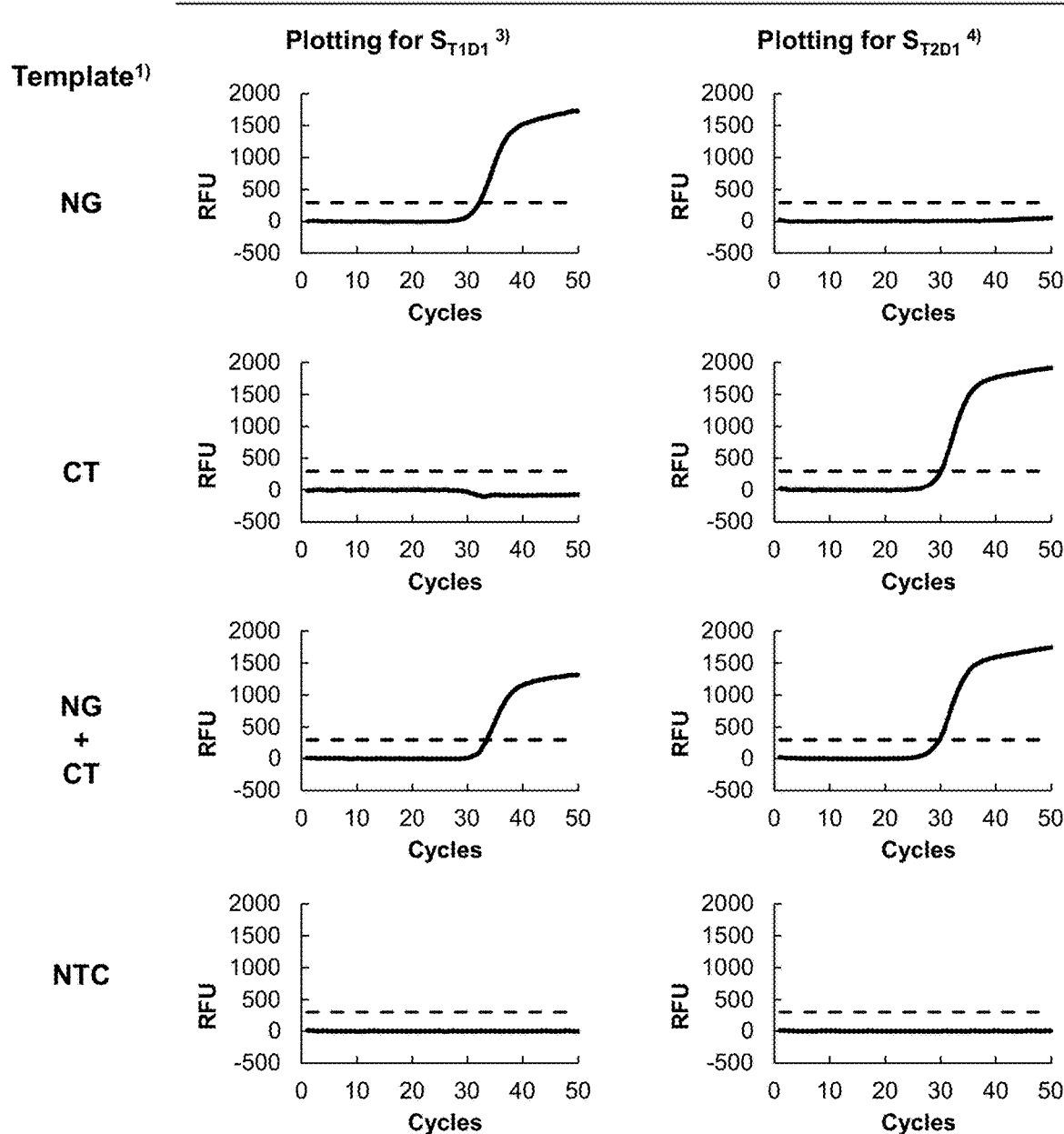
FIG. 2G represents plotting results for $S_{T1D1}$ and $S_{T2D1}$ obtained by solving the equation set 4 in which an arbitrary-selected constant value was used as $RV_{T1D1/D2}$. The dotted line represents a threshold.
Figure 2H:
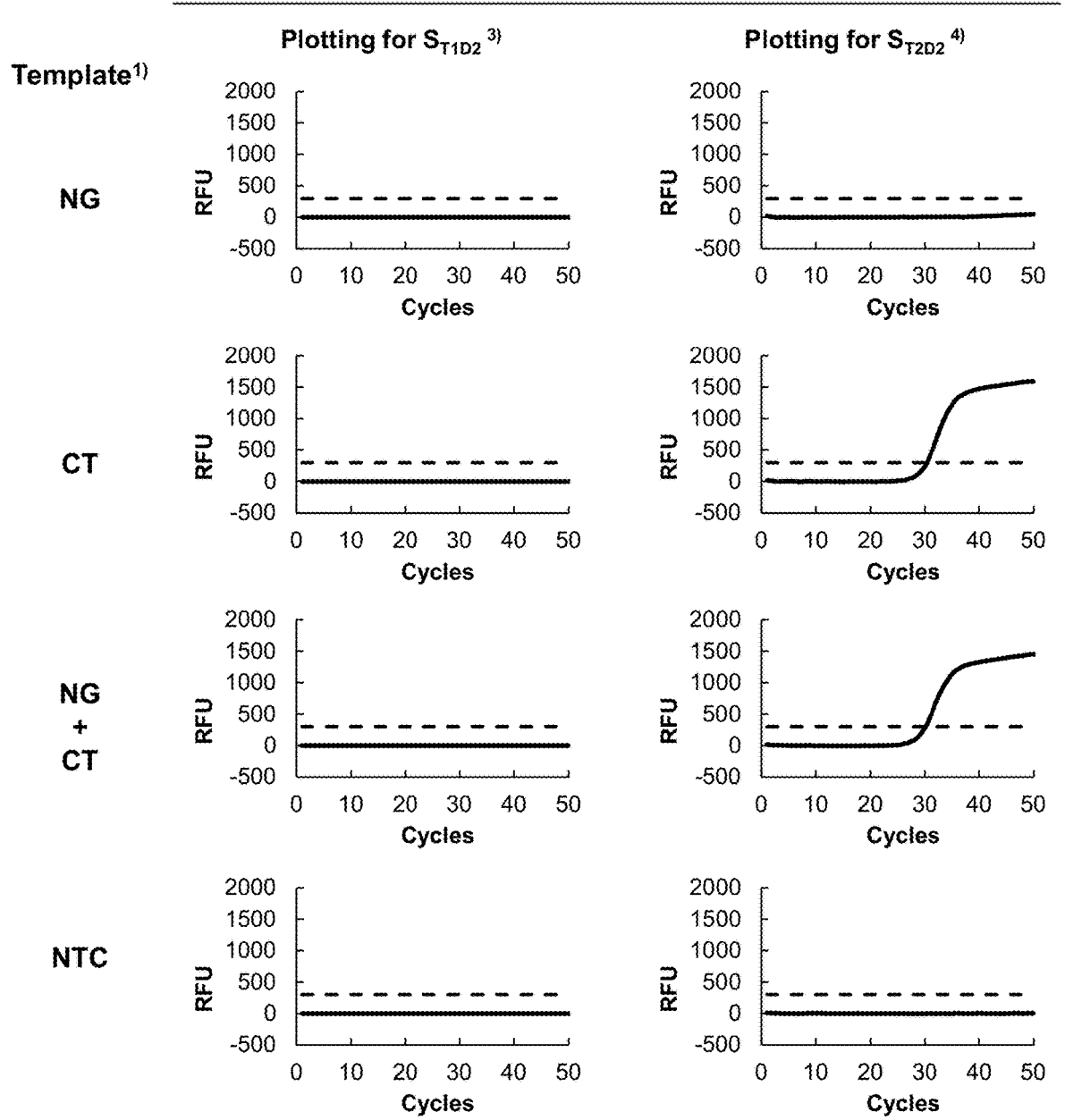
FIG. 2H represents plotting results for $S_{T1D2}$ and $S_{T2D2}$ obtained by solving the equation set 4 in which an arbitrary-selected constant value was used as $RV_{T1D1/D2}$. The dotted line represents a threshold.

As shown in FIGS. 2C, 2E and 2G, the amplification curves of the NG or the CT at 60° C. can confirm the presence or absence of target nucleic acid sequences in the each sample.

There results demonstrate that approach setting up and solving equations with variables, reference values and signals measured at each detection temperature allows for extracting or differentiating the signal of interest for each target sequence from signals detected at each detection temperature.

Therefore, two target nucleic acid sequences can be detected in a single reaction vessel by using a single detection channel and PTOCE real-time PCR comprising signal detection at different temperatures, addressing that the present equation solving-approach permits to determine the presence of target sequences in much more convenient and reliable manner.

Example 3: Three Target Detection by Performing TaqMan/PTOCE Real-Time PCR Comprising Signal Detection at Different Temperatures and Solving Equations We examined whether triple target nucleic acid sequences can be detected in a single reaction vessel by using a single detection channel and TaqMan/PTOCE real-time PCR comprising signal detection at different temperatures. Equations with variables representing signals of interest detected at the three detection temperature were setup and solved for differentiating the signals of interest and determining the presence or absence of the target nucleic acid sequences.

Taq DNA polymerase having a 5' nuclease activity was used for the extension of upstream primers and downstream primers, the cleavage of TaqMan probe, the cleavage of PTO, and the extension of PTO fragment. Genomic DNA of *Neisseria gonorrhoeae* (NG), genomic DNA of *Chlamydia trachomatis* (CT), and genomic DNA of *Mycoplasma genitalium* (MG) were used as target nucleic acid sequences. Eight reaction tubes were prepared containing NG, CT, MG, a mixture of NG and CT, a mixture of NG and MG, a mixture of CT and MG, a mixture of NG, CT and MG, and no target control respectively.

TaqMan real-time PCR was employed to detect MG. PTOCE real-time PCR was used to detect CT and NG.

"60° C.", "72° C." and "95° C." were selected as signal detection temperatures.

In this Example, the sequence and length of the extended duplex for CT is designed to provide a signal at 60° C. and 72° C. but not at 95° C. Meanwhile, the sequence and length of the extended duplex for NG is designed to provide a signal at 60° C., but not to provide a signal at 72° C. and 95° C. In the detection temperature of 95° C., the signal for MG will be generated and detected. In the detection temperature of 72° C., the signal for CT will be generated and detected as well as the signal for MG. Also, in the detection temperature of 60° C., the signal for NG will be generated and detected as well as the signal for MG and CT.

TaqMan probe is labeled with a fluorescent reporter molecule (CAL Fluor Red 610) at its 5'-end and a quencher molecule at its 3'-end (BHQ-2) (SEQ ID NO: 15). The PTO and CTO are blocked with a carbon spacer at their 3'-ends to prohibit their extension. CTO is labeled with a quencher molecule (BHQ-2) and a fluorescent reporter molecule (CAL Fluor Red 610) in its templating portion (SEQ ID NOs: 8 and 12).

In this Example, plotting methods using reference values of each target and the signals from three detection temperatures (95° C., 72° C., and 60° C.) provides amplification curves indicating the presence of each target nucleic acid sequence. Simultaneous equations were used as plotting methods and were applied for the extraction of each target's signal from each detection temperatures. Calculation for reference value and simultaneous equations to obtain amplification curves for each target nucleic acid sequence were as follows:

$$S_{T1D1}+S_{T2D1}+S_{T3D1}=S_{D1}$$

$$S_{T1D2}+S_{T2D2}+S_{T3D2}=S_{D2}$$

$$S_{T1D3}+S_{T2D3}+S_{T3D3}=S_{D3}$$

$$S_{T1D1}/S_{T1D2}=RV_{T1D1/D2}$$

$$S_{T1D1}/S_{T1D3}=RV_{T1D1/D3}$$

$$S_{T1D2}/S_{T1D3}=RV_{T1D2/D3}$$

$$S_{T2D1}/S_{T2D2}=RV_{T2D1/D2}$$

$$S_{T2D1}/S_{T2D3}=RV_{T2D1/D3}$$

$$S_{T2D2}/S_{T2D3}=RV_{T2D2/D3}$$

$$S_{T3D1}/S_{T3D2}=RV_{T3D1/D2}$$

$$S_{T3D1}/S_{T3D3}=RV_{T3D1/D3}$$

$$S_{T3D2}/S_{T3D3}=RV_{T3D2/D3} \qquad \text{<Equation set 5>}$$

$S_{T1D1}$ is a variable representing a signal of interest provided by NG at 60° C. detection temperature, wherein T1 represents NG target, D1 represents 60° C. detection temperature;

$S_{T2D1}$ is a variable representing a signal of interest provided by CT at 60° C. detection temperature, wherein T2 represents CT target, D1 represents 60° C. detection temperature;

$S_{T3D1}$ is a variable representing a signal of interest provided by MG at 60° C. detection temperature, wherein T3 represents MG target, D1 represents 60° C. detection temperature;

$S_{T1D2}$ is a variable representing a signal of interest provided by NG at 72° C. detection temperature, wherein T1 represents NG, D2 represents 72° C. detection temperature;

$S_{T2D2}$ is a variable representing a signal of interest provided by CT at 72° C. detection temperature, wherein T2 represents CT target, D2 represents 72° C. detection temperature;

$S_{T3D2}$ is a variable representing a signal of interest provided by MG at 72° C. detection temperature, wherein T3 represents MG target, D2 represents 72° C. detection temperature;

$S_{T1D1}$ is a variable representing a signal of interest provided by NG at 95° C. detection temperature, wherein T1 represents NG target, D3 represents 95° C. detection temperature;

$S_{T2D3}$ is a variable representing a signal of interest provided by CT at 95° C. detection temperature, wherein T2 represents CT target, D3 represents 95° C. detection temperature;

$S_{T3D3}$ is a variable representing a signal of interest provided by MG target at 95° C. detection temperature, wherein T3 represents MG target, D3 represents 95° C. detection temperature;

$S_{D1}$ is a constant and obtained experimentally by measuring a signal at 60° C.;

$S_{D2}$ is a constant and obtained experimentally by measuring signals at 72° C.;

$S_{D3}$ is a constant and obtained experimentally by measuring signals at 95° C.;

$RV_{T1D1/D2}$ is a constant and obtained experimentally by calculating RFU at 60° C. RFU at 72° C. at the end-point wherein RFUs are those measured in NG solely containing-sample. T1 represents NG, and D1 and D2 represent 60° C. and 72° C. detection temperatures, respectively;

$RV_{T1D1/D3}$ is a constant and obtained experimentally by calculating RFU at 60° C. RFU at 95° C. at the end-point wherein RFUs are those measured in NG solely containing-sample. T1 represents NG, and D1 and D3 represent 60° C. and 95° C. detection temperatures, respectively;

$RV_{T1D2/D3}$ is a constant and obtained experimentally by calculating RFU at 72° C. RFU at 95° C. at the end-point wherein RFUs are those measured in NG solely containing-sample. T1 represents NG, and D2 and D3 represent 72° C. and 95° C. detection temperatures, respectively;

$RV_{T2D1/D2}$ is a constant and obtained experimentally by calculating RFU at 60° C. RFU at 72° C. at the end-point wherein RFUs are those measured in CT solely containing-sample. T2 represents CT, and D1 and D2 represent 60° C. and 72° C. detection temperatures, respectively;

$RV_{T2D1/D3}$ is a constant and obtained experimentally by calculating RFU at 60° C. RFU at 95° C. at the end-point wherein RFUs are those measured in CT solely containing-sample. T2 represents CT, and D1 and D3 represent 60° C. and 95° C. detection temperatures, respectively;

$RV_{T2D2/D3}$ is a constant and obtained experimentally by calculating RFU at 72° C. RFU at 95° C. at the end-point wherein RFUs are those measured in CT solely containing-sample. T2 represents CT, and D2 and D3 represent 72° C. and 95° C. detection temperatures, respectively;

$RV_{T3D1/D2}$ is a constant and obtained experimentally by calculating RFU at 60° C. RFU at 72° C. at the end-point wherein RFUs are those measured in MG solely containing-sample. T3 represents MG, and D1 and D2 represent 60° C. and 72° C. detection temperatures, respectively;

$RV_{T3D1/D3}$ is a constant and obtained experimentally by calculating RFU at 60° C. RFU at 95° C. at the end-point wherein RFUs are those measured in MG solely containing-sample. T3 represents MG, and D1 and D3 represent 60° C. and 95° C. detection temperatures, respectively; and $RV_{T3D2/D3}$ is a constant and obtained experimentally by calculating RFU at 72° C. RFU at 95° C. at the end-point wherein RFUs are those measured in MG solely containing-sample. T3 represents MG, and D2 and D3 represent 72° C. and 95° C. detection temperatures, respectively.

One of approaches for solving the equation set is as follows: Linear simultaneous equation with three variables each of which is selected for each target sequence is newly established and then solutions to the three variables are obtained. For instance, by using suitable six equations among the nine RV equations in the Equation set 5, the following three linear simultaneous equations may be set up:

$$S_{T1D1} + S_{T2D1} + S_{T3D1} = S_{D1}$$

$$1/RV_{T1D1/D2} \times S_{T1D1} + 1/RV_{T2D1/D2} \times S_{T2D1} + 1/RV_{T3D1/D2} \times S_{T3D1} = S_{D2}$$

$$1/RV_{T1D1/D3} \times S_{T1D1} + 1/RV_{T2D1/D3} \times S_{T2D1} + 1/RV_{T3D1/D3} \times S_{T3D1} = S_{D3} \quad \text{Simultaneous equation 5}$$

$$RV_{T1D1/D2} \times S_{T1D2} + RV_{T2D1/D2} \times S_{T2D2} + RV_{T3D1/D2} \times S_{T3D2} = S_{D1}$$

$$S_{T1D2} + S_{T2D2} + S_{T3D2} = S_{D2}$$

$$1/RV_{T1D2/D3} \times S_{T1D2} + 1/RV_{T2D2/D3} \times S_{T2D2} + 1/RV_{T3D2/D3} \times S_{T3D2} = S_{D3} \quad \text{Simultaneous equation 6}$$

$$RV_{T1D1/D3} \times S_{T1D3} + RV_{T2D1/D3} \times S_{T2D3} + RV_{T3D1/D3} \times S_{T3D3} = S_{D1}$$

$$RV_{T1D2/D3} \times S_{T1D3} + RV_{T2D2/D3} \times S_{T2D3} + RV_{T3D2/D3} \times S_{T3D3} = S_{D2}$$

$$S_{T1D3} + S_{T2D3} + S_{T3D3} = S_{D3} \quad \text{Simultaneous equation 7}$$

Afterwards, the solutions to a corresponding variable at each cycle are obtained and then plotted. The plotting results may be considered as an amplification curve of a target sequence represented by a corresponding variable. Finally, the presence or absence of a target sequence is determined.

In this Example, the signal-generating means for NG was prepared to generate substantially no signal even in the presence of NG at the 72° C. and 95° C. detection temperatures, and the signal-generating means for CT was prepared to generate substantially no signal even in the presence of CT at the 95° C. detection temperature. Therefore, other equation sets may be also used instead of the Equation set 5.

As a first modification example of the Equation set 5, the equations $S_{T1D2} = 0$ and $S_{T1D3} = 0$ are used instead of equations comprising $RV_{T1D1/D2}$, $RV_{T1D1/D3}$ or $RV_{T1D2/D3}$ among reference values for NG, and the equation $S_{T2D3} = 0$ is used instead of equations comprising $RV_{T2D1/D3}$ or $RV_{T2D2/D3}$ among reference values for CT.

According to a second modification example, arbitrary-selected values for $RV_{T1D1/D2}$, $RV_{T1D1/D3}$, $RV_{T1D2/D3}$, $RV_{T2D1/D3}$ and $RV_{T2D2/D3}$ may be used instead of experimentally-obtained values.

A combinatory embodiment of the first and second modifications may be also used in the present method.

The sequences of upstream primer, downstream primer, PTO, CTO and TaqMan probe used in this Example are:

```
NG-F
                                          (SEQ ID NO: 1)
5'-TACGCCTGCTACTTTCACGCTIIIIIGTAATCAGATG-3'

NG-R
                                          (SEQ ID NO: 2)
5'-CAATGGATCGGTATCACTCGCIIIIICGAGCAAGAAC-3'

NG-PTO
                                          (SEQ ID NO: 7)
5'-GTACGCGATACGGGCCCCTCATTGGCGTGTTT

CG[C3 spacer]-3'

NG-CTO
                                          (SEQ ID NO: 8)
5'-[BHQ-2]TTTTTTTTTTTTTTTTTG[T(CAL Fluor Red 610)]ACTGCCCGTATCGCGTAC[C3 spacer]-3'

CT-F2
                                          (SEQ ID NO: 9)
5'-GAGTTTTAAAATGGGAAATTCTGGTIIIIITTTGTATAAC-3'

CT-R2
                                         (SEQ ID NO: 10)
5' -CCAATTGTAATAGAAGCATTGGTTGIIIIITTATTGGAGA-3'

CT-PTO
                                         (SEQ ID NO: 11)
5'-GATTACGCGACCGCATCAGAAGCTGTCATTTTGGCTGCG[C3 spacer]-3'

CT-CTO
                                         (SEQ ID NO: 12)
5'-[BHQ-2]GCGCTGGATACCCTGGACGA[T(CAL Fluor Red 610)]ATGTGCGGTCGCGTAATC[C3 spacer]-3'

MG-F
                                         (SEQ ID NO: 13)
5'-AAAACCCACGGAAATGATGAGAIIIIIATTGGTTCTAC-3'

MG-R
                                         (SEQ ID NO: 14)
5'-CTCGTTAATTTACCTATTCCATTTTGIIIIICTGATAAAAG-3'

MG-P
                                         (SEQ ID NO: 15)
5'-[CAL Fluor Red 610]GAGTTCTT

TCAAGAACAGCAAGAGGTGT[BHQ-2]-3'
```

(I: Deoxyinosine)
(Underlined letters indicate the 5'-tagging portion of PTO)

The real-time PCR was conducted in the final volume of 20 μl containing a target nucleic acid sequence (10 pg of NG genomic DNA, 10 pg of CT genomic DNA, 10 pg of MG genomic DNA, a mixture of each 10 pg of NG and CT genomic DNA, a mixture of each 10 pg of NG and MG genomic DNA, a mixture of each 10 pg of CT and MG genomic DNA; or a mixture of each 10 pg of NG, CT and MG genomic DNA), 5 pmole of upstream primer (SEQ ID NO: 1) and 5 pmole of downstream primer (SEQ ID NO: 2) for NG target amplification, 3 pmole of PTO (SEQ ID NO: 7), 1 pmole of CTO (SEQ ID NO: 8), 5 pmole of upstream primer (SEQ ID NO: 9) and 5 pmole of downstream primer (SEQ ID NO: 10) for CT target amplification, 3 pmole of PTO (SEQ ID NO: 11), 1 pmole of CTO (SEQ ID NO: 12), 5 pmole of upstream primer (SEQ ID NO: 13) and 5 pmole of downstream primer (SEQ ID NO: 14) for MG target amplification, 1 pmole of TaqMan probe (SEQ ID NO: 15), and 10 μl of 2× Master Mix [final, 200 uM dNTPs, 2 mM $MgCl_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C., 72° C., and 95° C. of each cycle.

Figure 3A:
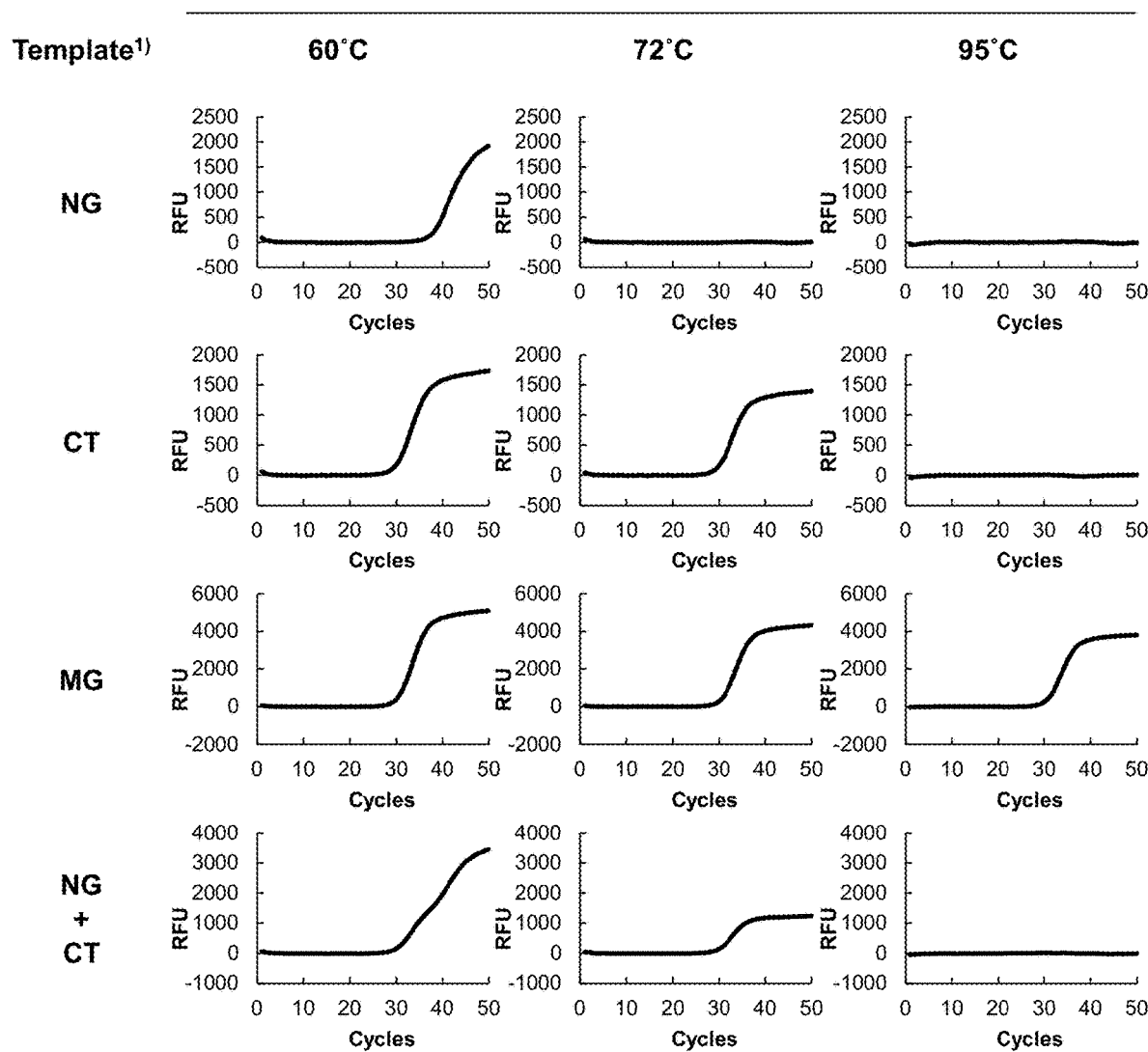
FIGS. 3A and 3B represent the detection results of three target nucleic acid sequences [genomic DNA of *Neisseria gonorrhoeae* (NG), genomic DNA of *Chlamydia trachomatis* (CT), and genomic DNA of *Mycoplasma genitalium* (MG)] and their combination at three detection temperature (60° C., 72° C. and 95° C.). The signals for NG and CT were generated by the TOCE method, and the signals for MG were generated by the TaqMan probe method.
Figure 3B:
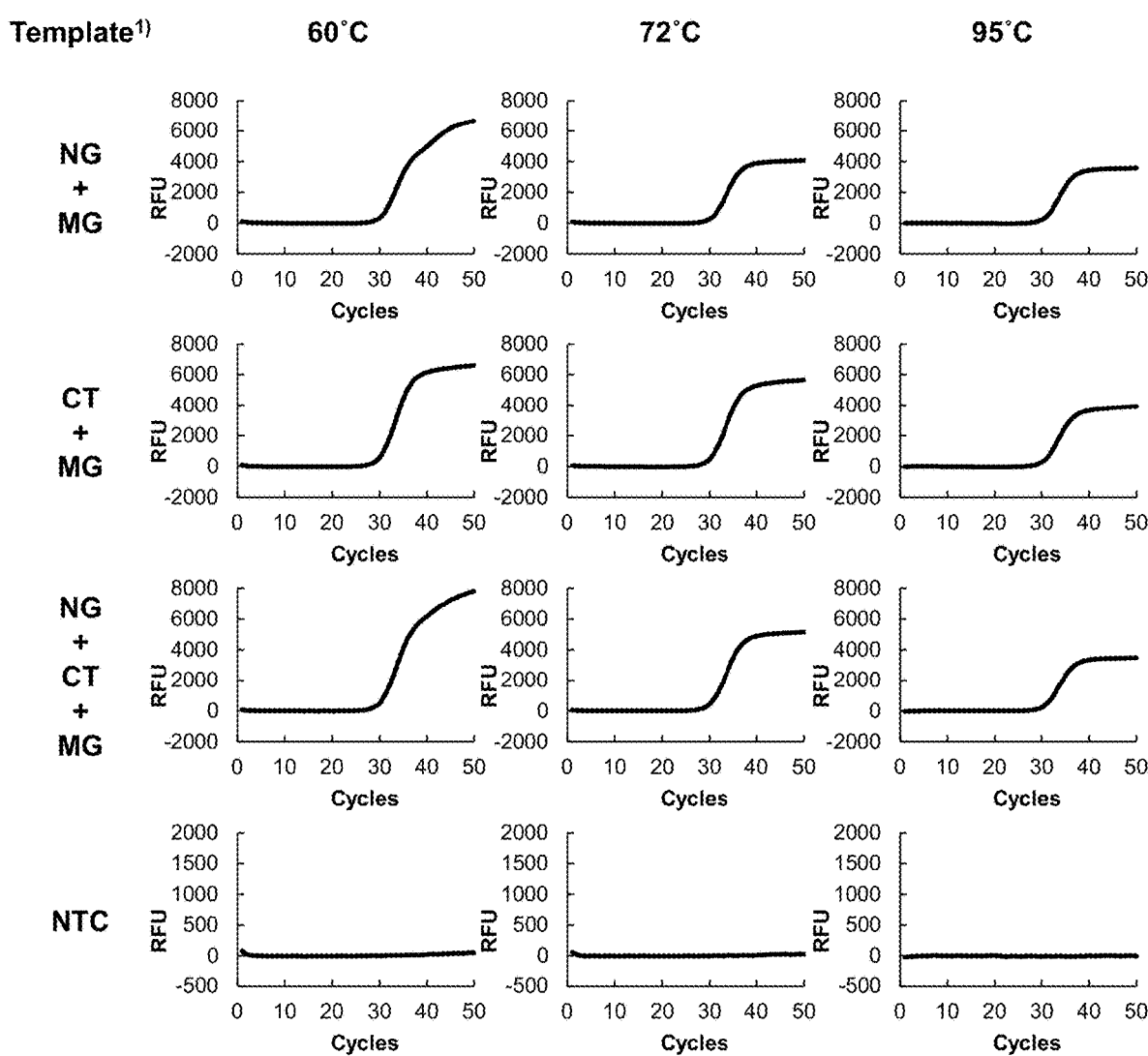

As shown in FIGS. 3A and 3B, signals were detected at 60° C. in the presence of NG, CT, MG, and mixed targets. In the sole presence of CT, a signal was detected at 72° C. and 60° C. but not at 95° C. In the sole presence of NG, a signal was detected at 60° C. but not at 95° C. and 72° C. No signal was detected in the absence of the target nucleic acid sequences. Reference values of each target were calculated using the signals of NG only sample or CT only or MG only sample and shown in FIG. 3C.

The plotting result for $S_{T1D1}$, $S_{T2D1}$, $S_{T3D1}$, $S_{T1D2}$, $S_{T2D2}$/$S_{T3D2}$, $S_{T1D3}$, $S_{T2D3}$, and $S_{T3D3}$ can be considered as an amplification curve of NG at 60° C., an amplification curve of CT at 60° C., an amplification curve of MG at 60° C., an amplification curve of NG at 72° C., an amplification curve of CT at 72° C., an amplification curve of MG at 72° C., an amplification curve of NG at 95° C., an amplification curve of CT at 95° C., and an amplification curve of MG at 95° C. respectively. Proper thresholds were selected referring to the result of NG only sample, CT only sample, and MG only sample to verify the significance of the obtained amplification curves.

As shown in FIGS. 3D and 3E, the amplification curves of the NG, the CT, or the MG at 60° C. can confirm the presence or absence of target nucleic acid sequences in the each sample.

These results demonstrate that approach setting up and solving equations with variables, reference values and signals measured at each detection temperature allows for extracting or differentiating the signal of interest for each target sequence from signals detected at each detection temperature.

Therefore, three target nucleic acid sequences can be detected in a single reaction vessel by using a single detection channel and TaqMan/PTOCE real-time PCR comprising signal detection at different temperatures, addressing that the present equation solving-approach permits to determine the presence of at least three target sequences in much more convenient and reliable manner.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for differentiating signals of interest for each of two target nucleic acid sequences comprising a first target nucleic acid sequence (T1) and a second target nucleic acid sequence (T2) in a sample, which are not differentiable by a single type of detector, comprising:

(a) incubating the sample with a first signal-generating means for detection of the first target nucleic acid sequence (T1) and a second signal-generating means for detection of the second target nucleic acid sequence (T2) and detecting signals at a first detection temperature (D1) and a second detection temperature (D2); wherein the signals of interest to be generated by the two signal-generating means are not differentiated for each target nucleic acid sequence by a single type of detector;

(b) providing the following two equations each of which comprises variables representing the signals of interest generated at each detection temperature for the two target nucleic acid sequences;

$$S_{T1D1} + S_{T2D1} = S_{D1} \quad (I)$$

$$S_{T1D2} + S_{T2D2} = S_{D2} \quad (II)$$

wherein ($S_{D1}$) is a signal detected at the first detection temperature, ($S_{D2}$) is a signal detected at the second detection temperature; ($S_{T1D1}$) is a variable representing a signal of interest generated by the first signal-generating means at the first detection temperature, ($S_{T2D1}$) is a variable representing a signal of interest generated by the second signal-generating means at the first detection temperature, ($S_{T1D2}$) is a variable representing a signal of interest generated by the first signal-generating means at the second detection temperature, ($S_{T2D2}$) is a variable representing a signal of interest generated by the second signal-generating means at the second detection temperature; and the total number of variables is four;
(c) providing two additional equations selected from the group consisting of the following equations:

$$f(S_{T1D1}, S_{T1D2}) = RV_{T1(D1D2)} \quad \text{(III)},$$

$$f(S_{T2D1}, S_{T2D2}) = RV_{T2(D1D2)} \quad \text{(IV), and}$$

$$S_{T1D2} = 0 \quad \text{(V)}$$

wherein, $RV_{T1(D1D2)}$ is a reference value (RV) of the first target nucleic acid sequence (T1) representing a relationship of change in signals provided by the first signal-generating means at the first detection temperature and the second detection temperature, $RV_{T2(D1D2)}$ is a reference value (RV) of the second target nucleic acid sequence (T2) representing a relationship of change in signals provided by the second signal-generating means at the first detection temperature and the second detection temperature; $f(S_{T1D1}, S_{T1D2})$ represents a function of $S_{T1D1}$ and $S_{T1D2}$; $f(S_{T2D1}, S_{T2D2})$ represents a function of $S_{T2D1}$ and $S_{T2D2}$;

wherein $S_{T1D2} = 0$ in the equation (V) may be selected with a proviso that the first signal-generating means is prepared to generate no signal in the presence of the first target nucleic acid sequence at the second detection temperature; and (d) obtaining solutions to at least one of the variables by the four equations provided in the steps (b) and (c) for differentiating at least one of the signals of interest to be assigned to at least one of the two target nucleic acid sequences.

2. The method of claim 1, wherein the method is performed to detect at least one of the two target nucleic acid sequences in the sample by assigning the at least one of the signals of interest to at least one of the two target nucleic acid sequences.

3. The method of claim 1, wherein the equation (III) is used to convert the two variables ($S_{T1D1}$) and ($S_{T1D2}$) in the equations (I) and (II) into a variable selected from the two variables, and the equation (IV) is used to convert the two variables ($S_{T2D1}$) and ($S_{T2D2}$) in the equations (I) and (II) into a variable selected from the two variables.

4. The method of claim 1, wherein (i) $RV_{T1(D1D2)}$ is obtained by (i-1) incubating the first target nucleic acid sequence with the first signal-generating means for detection of the first target nucleic acid sequence, (i-2) detecting signals at the first detection temperature and the second detection temperature, and (i-3) then obtaining a difference between the signals detected at the first detection temperature and the second detection temperature, and (ii) $RV_{T2(D1D2)}$ is obtained by (ii-1) incubating the second target nucleic acid sequence with the second signal-generating means for detection of the second target nucleic acid sequence, (ii-2) detecting signals at the first detection temperature and the second detection temperature, and (ii-3) then obtaining a difference between the signals detected at the first detection temperature and the second detection temperature; wherein $RV_{T1(D1D2)}$ is different from $RV_{T2(D1D2)}$.

5. The method of claim 1, wherein $f(S_{T1D1}, S_{T1D2}) = RV_{T1(D1D2)}$ comprises $S_{T1D1}/S_{T1D2} = RV_{T1D1/D2}$ (VI) or $S_{T1D2}/S_{T1D1} = RV_{T1D2/D1}$ (VII); $f(S_{T2D1}, S_{T2D2}) = RV_{T2(D1D2)}$ comprises $S_{T2D1}/S_{T2D2} = RV_{T2D1/D2}$ (VIII) or $S_{T2D2}/S_{T2D1} = RV_{T2D2/D1}$ (IX).

6. The method of claim 5, wherein $RV_{T1D1/D2}$ is obtained by (i-1) incubating the first target nucleic acid sequence with the first signal-generating means for detection of the first target nucleic acid sequence, (i-2) detecting signals at the first detection temperature and the second detection temperature, and (i-3) then calculating a ratio of a signal detected at the first detection temperature to a signal detected at the second detection temperature; $RV_{T1D2/D1}$ is obtained by performing the steps (i-1) and (i-2) and then calculating a ratio of the signal detected at the second detection temperature to the signal detected at the first detection temperature; $RV_{T2D1/D2}$ is obtained by (ii-1) incubating the second target nucleic acid sequence with the second signal-generating means for detection of the second target nucleic acid sequence, (ii-2) detecting signals at the first detection temperature and the second detection temperature, and then (ii-3) calculating a ratio of the signal detected at the first detection temperature to the signal detected at the second detection temperature; and $RV_{T2D2/D1}$ is obtained by performing the steps (ii-1) and (ii-2) and then calculating a ratio of the signal detected at the second detection temperature to the signal detected at the first detection temperature.

7. The method of claim 1, wherein when the first signal-generating means is prepared to generate no signal in the presence of the first target nucleic acid sequence at the second detection temperature, $RV_{T1(D1D2)}$ is 0.

8. The method of claim 1, wherein the two additional equations for obtaining ($S_{T1D1}$), ($S_{T1D2}$), ($S_{T2D1}$) and ($S_{T2D2}$) comprises one of the following equations (VI) and (VII) and one of the following equations (VIII) and (IX):

$$S_{T1D1}/S_{T1D2} = RV_{T1D1/D2} \quad \text{(VI)}$$

$$S_{T1D2}/S_{T1D1} = RV_{T1D2/D1} \quad \text{(VII)}$$

$$S_{T2D1}/S_{T2D2} = RV_{T2D1/D2} \quad \text{(VIII)}$$

$$S_{T2D2}/S_{T2D1} = RV_{T2D2/D1} \quad \text{(IX)}.$$

9. The method of claim 1, wherein the two additional equations for obtaining ($S_{T1D1}$), ($S_{T1D2}$), ($S_{T2D1}$) and ($S_{T2D2}$) comprises one of the following equations (VIII) and (IX) and the following equation (V):

$$S_{T2D1}/S_{T2D2} = RV_{T2D1/D2} \quad \text{(VIII)}$$

$$S_{T2D2}/S_{T2D1} = RV_{T2D2/D1} \quad \text{(IX)}$$

$$S_{T1D2} = 0 \quad \text{(V)}$$

10. A method for differentiating signals of interest for each of target nucleic acid sequences in the number of N in a sample, which are not differentiable by a single type of detector, comprising:
(a) incubating the sample with signal-generating means in the number of N for detection of the target nucleic acid sequences in the number of N and detecting signals at detection temperatures in the number of N; wherein each of the target nucleic acid sequences is detected by a corresponding signal-generating means; wherein the signals of interest to be generated by the signal-generating means in the number of N are not differentiated for each target nucleic acid sequence by a single type of detector; wherein N is an integer not less than 2;
(b) providing the following equations in the number of N each of which comprises variables representing the signals of interest generated at each detection temperature for the target nucleic acid sequences;

$$S_{T1D1} + S_{T2D1} + \ldots + S_{TND1} = S_{D1} \quad (1)$$

$$S_{T1D1} + S_{T2D1} + \ldots + S_{TND1} = S_{D1} \quad (1)$$

$$S_{T1D2} + S_{T2D2} + \ldots + S_{TND2} = S_{D2} \quad (2)$$

$$\vdots$$

$$S_{T1DN} + S_{T2DN} + \ldots + S_{TNDN} = S_{DN} \quad (N)$$

wherein each of ($S_{D1}$) to ($S_{DN}$) is a signal detected at each detection temperature; each of ($S_{T1D1}$) to ($S_{TNDN}$) is a variable representing a signal of interest generated by each signal-generating means at each detection temperature; and the total number of the variables is $N^2$;

(c) providing additional equations in the number of ($N^2-N$) selected from the group consisting of the following equations:

$$f(S_{TjD\alpha}, S_{TjD\beta}) = RV_{Tj(D\alpha D\beta)} \quad (X), \text{ and}$$

$$S_{TjDK} = 0 \quad (XI)$$

wherein, j in Tj represents all integers starting from 1 to a $N^{th}$ integer; for each $j^{th}$ target nucleic acid, $\alpha$ and $\beta$ jointly represent a combination of two integers selected from 1 to N; wherein the number of the combination is represented by $_NC_2$; for each $j^{th}$ target nucleic acid, K is at least one of integers selected from 1 to N; $RV_{Tj(D\alpha D\beta)}$ is a reference value (RV) of the $j^{th}$ target nucleic acid sequence (Tj) representing relationship reflecting change in signals provided by the $j^{th}$ signal-generating means at the $\alpha^{th}$ detection temperature and the $\beta^{th}$ detection temperature; $f(S_{TjD\alpha}, S_{TjD\beta})$ represents a function of $S_{TjD\alpha}$ and $S_{TjD\beta}$;

wherein $S_{TjDK}=0$ in the equation (XI) may be selected with a proviso that the $j^{th}$ signal-generating means is prepared to generate no signal in the presence of the $j^{th}$ target nucleic acid sequence at the $K^{th}$ detection temperature; and (d) obtaining solutions to at least one of the variables by the equations in the number of $N^2$ provided in the steps (b) and (c) for differentiating at least one of the signals of interest to be assigned to at least one of the target nucleic acid sequences in the number of N.

11. The method of claim 10, wherein the method is performed to detect at least one of the target nucleic acid sequences in the sample by assigning the at least one of the signals of interest to at least one of the target nucleic acid sequences.

12. The method of claim 10, wherein the equation (X) comprising the reference value (RV) of the $j^{th}$ target nucleic acid sequence (Tj) is used to convert the variables ($S_{TjD1}$) to ($S_{TjDN}$) in the equations (1) to (N) into a variable selected from the variables ($S_{TjD1}$) to ($S_{TjDN}$).

13. The method of claim 10, wherein $RV_{Tj(D\alpha D\beta)}$ is obtained by (i-1) incubating the $j^{th}$ target nucleic acid sequence with the $j^{th}$ signal-generating means for detection of the $j^{th}$ target nucleic acid sequence, (i-2) detecting signals at the $\alpha^{th}$ detection temperature and the $\beta^{th}$ detection temperature, and (i-3) then obtaining a difference between the signals detected at the $\alpha^{th}$ detection temperature and the $\beta^{th}$ detection temperature.

14. The method of claim 10, wherein $f(S_{TjD\alpha}, S_{TjD\beta}) = RV_{Tj(D\alpha D\beta)}$ comprises $S_{TjD\alpha}/S_{TjD\beta} = RV_{TjD\alpha/D\beta}$ (XII) or $S_{TjD\beta}/S_{TjD\alpha} = RV_{TjD\beta/D\alpha}$ (XIII).

15. The method of claim 14, wherein $RV_{TjD\alpha/D\beta}$ is obtained by (i-1) incubating the $j^{th}$ target nucleic acid sequence with the $j^{th}$ signal-generating means for detection of the $j^{th}$ target nucleic acid sequence, (i-2) detecting signals at the $\alpha^{th}$ detection temperature and the $\beta^{th}$ detection temperature, and (i-3) then calculating a ratio of a signal detected at the $\alpha^{th}$ detection temperature to a signal detected at the $\beta^{th}$ detection temperature; $RV_{TjD\beta/D\alpha}$ is obtained by performing the steps (i-1) and (i-2) and then calculating a ratio of the signal detected at the $\beta^{th}$ detection temperature to the signal detected at the $\alpha^{th}$ detection temperature.

16. The method of claim 10, wherein when the $j^{th}$ signal-generating means is prepared to generate no signal in the presence of the $j^{th}$ target nucleic acid sequence at the $K^{th}$ detection temperature, $RV_{Tj(D\alpha D\beta)}$ in which $\alpha$ or $\beta$ is the same as K is 0.

17. The method of claim 10, wherein the additional equations in the number of $N^2-N$ are selected from the groups of the following equations:

$$S_{TjD\alpha}/S_{TjD\beta} = RV_{TjD\alpha/D\beta} \quad (XII)$$

$$S_{TjD\beta}/S_{TjD\alpha} = RV_{TjD\beta/D\alpha} \quad (XIII)$$

wherein the equation for each $j^{th}$ target nucleic acid at the $\alpha^{th}$ detection temperature and the $\beta^{th}$ detection temperature is selected from the equations (XII) and (XIII).

18. The method of claim 10, wherein the additional equations in numbers of $N^2-N$ are selected from the groups of the following equations:

$$S_{TjD\alpha}/S_{TjD\beta} = RV_{TjD\alpha/D\beta} \quad (XII)$$

$$S_{TjD\beta}/S_{TjD\alpha} = RV_{TjD\beta/D\alpha}, \quad (XIII)$$

$$S_{TjDK} = 0 \quad (XI)$$

wherein the equation for each $j^{th}$ target nucleic acid at the $\alpha^{th}$ detection temperature and the $\beta^{th}$ detection temperature is selected from the equations (XII) and (XIII);

wherein when the equation (XI) is selected as the additional equations, the other additional equations are selected from the equations (XII) and (XIII) in which $\alpha$ or $\beta$ for the $j^{th}$ target nucleic acid sequence is different from K for the $j^{th}$ target nucleic acid sequence.

19. The method of claim 1, wherein the step (a) is performed in a signal amplification process concomitantly with a nucleic acid amplification.

20. The method of claim 1, wherein the step (a) is performed in a signal amplification process without a nucleic acid amplification.

21. A kit for differentiating signals of interest for each of two target nucleic acid sequences comprising a first target nucleic acid sequence (T1) and a second target nucleic acid sequence (T2) in a sample, which are not differentiable by a single type of detector, comprising:

(a) two signal-generating means for detection of the two target nucleic acid sequences; and (b) an instruction that describes the method of claim 1.

22. A kit for differentiating signals of interest for each of target nucleic acid sequences in the number of N in a sample, which are not differentiable by a single type of detector, comprising:

(a) signal-generating means in the number of N for detection of the target nucleic acid sequences in the number of N; and (b) an instruction that describes the method of claim 10.

23. A non-transitory computer readable storage medium containing instructions to configure a processor to perform a method for differentiating signals of interest for each of two target nucleic acid sequences comprising a first target nucleic acid sequence (T1) and a second target nucleic acid sequence (T2) in a sample, which are not differentiable by a single type of detector, the method comprising:
   (a) receiving signals detected at a first detection temperature (D1) and a second detection temperature (D2); wherein the first target nucleic acid sequence (T1) in the sample is detected by a first signal-generating means and the second target nucleic acid sequence (T2) in the sample is detected by a second signal-generating means; wherein the signals of interest to be generated by the two signal-generating means are not differentiated by a single type of detector;
   (b) providing the following two equations each of which comprises variables representing the signals of interest generated at each detection temperature for the two target nucleic acid sequences;

$$S_{T1D1} + S_{T2D1} = S_{D1} \tag{I}$$

$$S_{T1D2} + S_{T2D2} = S_{D2} \tag{II}$$

wherein ($S_{D1}$) is a signal detected at the first detection temperature, ($S_{D2}$) is a signal detected at the second detection temperature; ($S_{T1D1}$) is a variable representing a signal of interest generated by the first signal-generating means at the first detection temperature, ($S_{T2D1}$) is a variable representing a signal of interest generated by the second signal-generating means at the first detection temperature, ($S_{T1D2}$) is a variable representing a signal of interest generated by the first signal-generating means at the second detection temperature, ($S_{T2D2}$) is a variable representing a signal of interest generated by the second signal-generating means at the second detection temperature; and the total number of variables is four;
   (c) providing two additional equations selected from the group consisting of the following equations:

$$f(S_{T1D1}, S_{T1D2}) = RV_{T1(D1D2)} \tag{III},$$

$$f(S_{T2D1}, S_{T2D2}) = RV_{T2(D1D2)} \tag{IV, and}$$

$$S_{T1D2} = 0 \tag{V}$$

wherein, $RV_{T1(D1D2)}$ is a reference value (RV) of the first target nucleic acid sequence (T1) representing a relationship of change in signals provided by the first signal-generating means at the first detection temperature and the second detection temperature, $RV_{T2(D1D2)}$ is a reference value (RV) of the second target nucleic acid sequence (T2) representing a relationship of change in signals provided by the second signal-generating means at the first detection temperature and the second detection temperature; $f(S_{T1D1}, S_{T1D2})$ represents a function of $S_{T1D1}$ and $S_{T1D2}$; $f(S_{T2D1}, S_{T2D2})$ represents a function of $S_{T2D1}$ and $S_{T2D2}$;
   wherein $S_{T1D2}=0$ in the equation (V) may be selected with a proviso that the first signal-generating means is prepared to generate no signal in the presence of the first target nucleic acid sequence at the second detection temperature
   wherein $f(S_{T1D1}, S_{T1D2}) = RV_{T1(D1D2)}$ is $S_{T1D1}/S_{T1D2} = RV_{T1D1/D2}$ (VI) or $S_{T1D2}/S_{T1D1} = RV_{T1D2/D1}$ (VII); $f(S_{T2D1}, S_{T2D2}) = RV_{T2(D1D2)}$ is $S_{T2D1}/S_{T2D2} = RV_{T2D1/D2}$ or $S_{T2D2}/S_{T2D1} = RV_{T2D2/D1}$ (IX); and
   (d) obtaining solutions to at least one of the variables by the four equations provided in the steps (b) and (c) for differentiating at least one of the signals of interest to be assigned to at least one of the two target nucleic acid sequences.

24. A non-transitory computer readable storage medium containing instructions to configure a processor to perform a method for differentiating signals of interest for each of target nucleic acid sequences in the number of N in a sample, which are not differentiable by a single type of detector, the method comprising:
   (a) receiving signals detected at detection temperatures in the number of N; wherein each of the target nucleic acid sequences in the sample is detected by a corresponding signal-generating means; wherein the signals of interest to be generated by the signal-generating means in the number of N are not differentiated for each target nucleic acid sequence by a single type of detector; wherein N is an integer not less than 2;
   (b) providing the following equations in the number of N each of which comprises variables representing the signals of interest generated at each detection temperature for the target nucleic acid sequences;

$$S_{T1D1} + S_{T2D1} + \ldots + S_{TND1} = S_{D1} \tag{1}$$

$$S_{T1D2} + S_{T2D2} + \ldots + S_{TND2} = S_{D2} \tag{2}$$

$$\vdots$$

$$S_{T1DN} + S_{T2DN} + \ldots + S_{TNDN} = S_{DN} \tag{N}$$

wherein each of($S_{D1}$) to ($S_{DN}$) is a signal detected at each detection temperature; each of($S_{T1D1}$) to ($S_{TNDN}$) is a variable representing a signal of interest generated by each signal-generating means at each detection temperature; and the total number of the variables is $N^2$;
   (c) providing additional equations in the number of ($N^2-N$) selected from the group consisting of the following equations:

$$f(S_{TjD\alpha}, S_{TjD\beta}) = RV_{Tj(D\alpha D\beta)} \tag{X, and}$$

$$S_{TjDK} = 0 \tag{XI}$$

wherein, j in Tj represents all integers starting from 1 to a $N^{th}$ integer; for each $j^{th}$ target nucleic acid, $\alpha$ and $\beta$ jointly represent a combination of two integers selected from 1 to N; wherein the number of the combination is represented by $_NC_2$; for each $j^{th}$ target nucleic acid, K is at least one of integers selected from 1 to N; $RV_{Tj(D\alpha D\beta)}$ is a reference value (RV) of the $j^{th}$ target nucleic acid sequence (Tj) representing relationship reflecting change in signals provided by the $j^{th}$ signal-generating means at the $\alpha^{th}$ detection temperature and the $\beta^{th}$ detection temperature; $f(S_{TjD\alpha}, S_{TjD\beta})$ represents a function of $S_{TjD\alpha}$ and $S_{TjD\beta}$;
   wherein $S_{TjDK}=0$ in the equation (XI) may be selected with a proviso that the $j^{th}$ signal-generating means is prepared to generate no signal in the presence of the $j^{th}$ target nucleic acid sequence at the $K^{th}$ detection temperature
   wherein $f(S_{TjD\alpha}, S_{TjD\beta}) = RV_{Tj(D\alpha D\beta)}$ is $S_{TjD\alpha}/S_{TjD\beta} = RV_{TjD\alpha/D\beta}$ (XII) or $S_{TjD\beta}/S_{TjD\alpha} = RV_{TjD\beta/D\alpha}$ (XIII); and
   (d) obtaining solutions to at least one of the variables by the equations in the number of $N^2$ provided in the steps (b) and (c) for differentiating at least one of the signals of interest to be assigned to at least one of the target nucleic acid sequences in the number of N.

25. A device for differentiating signals of interest for each of two target nucleic acid sequences comprising a first target nucleic acid sequence (T1) and a second target nucleic acid sequence (T2) in a sample, which are not differentiable by a single type of detector, comprising (a) a computer processor and (b) the computer readable storage medium of claim 23 coupled to the computer processor.

26. A device for differentiating signals of interest for each of target nucleic acid sequences in the number of N in a sample, which are not differentiable by a single type of detector, comprising (a) a computer processor and (b) the computer readable storage medium of claim 24 coupled to the computer processor.

\* \* \* \* \*